(12) United States Patent
Jackson et al.

(10) Patent No.: US 11,497,532 B2
(45) Date of Patent: Nov. 15, 2022

(54) PIVOTAL BONE ANCHOR SYSTEM WITH UNIVERSAL SHANK HEAD

(71) Applicant: Roger P. Jackson, Prairie Village, KS (US)

(72) Inventors: Roger P. Jackson, Prairie Village, KS (US); James L. Surber, Kansas City, KS (US)

(*) Notice: Subject to any disclaimer, the term of this patent is extended or adjusted under 35 U.S.C. 154(b) by 0 days.

(21) Appl. No.: 17/467,721

(22) Filed: Sep. 7, 2021

(65) Prior Publication Data

US 2021/0401467 A1  Dec. 30, 2021

Related U.S. Application Data

(63) Continuation of application No. 16/522,426, filed on Jul. 25, 2019, now Pat. No. 11,109,896, which is a
(Continued)

(51) Int. Cl.
*A61B 17/70* (2006.01)
*A61B 17/86* (2006.01)
(Continued)

(52) U.S. Cl.
CPC ........ *A61B 17/7037* (2013.01); *A61B 17/702* (2013.01); *A61B 17/7005* (2013.01);
(Continued)

(58) Field of Classification Search
CPC ............ A61B 17/7037; A61B 17/7005; A61B 17/7008; A61B 17/702; A61B 17/7038; A61B 17/7082; A61B 17/7091; A61B 17/864; A61B 2017/681; A61B 2017/567; A61B 2090/0808; Y10T 29/49826
(Continued)

(56) References Cited

U.S. PATENT DOCUMENTS 5,501,684 A  3/1996  Schlapfer
5,584,834 A  12/1996  Errico et al.
(Continued)

*Primary Examiner* — Nicholas J Plionis
(74) *Attorney, Agent, or Firm* — Polsinelli PC

(57) ABSTRACT

A pivotal spinal fixation system includes bone anchors comprising capture portions having a partial spherical shape with flat side surfaces, multi-planar receivers with continuous interior circumferential engagement surfaces proximate their bottom openings, and uni-planar receivers with non-continuous interior circumferential engagement surface proximate their bottom openings. The system also includes circular retainers, each having a non-continuous outer circumferential surface configured for non-pivotal engagement with the interior circumferential engagement surfaces of both the multi-planar receivers and the uni-planar receivers, and an inner surface configured to expand and contract around the capture portion and flat side surfaces of a bone anchor so as to capture the bone anchor within a multi-planar or uni-planar receiver. The system provides for pivotal motion of the bone anchors in any of a plurality of angular directions relative to the vertical centerline axes of the multi-planar receivers while limiting pivotal motion to a single pivot plane relative to the vertical centerline axes of the uni-planar receivers.

37 Claims, 32 Drawing Sheets

Related U.S. Application Data continuation of application No. 16/040,258, filed on Jul. 19, 2018, now Pat. No. 10,398,475, which is a continuation-in-part of application No. 15/878,542, filed on Jan. 24, 2018, now Pat. No. 10,172,649, which is a continuation-in-part of application No. 15/338,817, filed on Oct. 31, 2016, now Pat. No. 9,883,892, which is a continuation of application No. 13/573,874, filed on Oct. 10, 2012, now Pat. No. 9,480,517, which is a continuation-in-part of application No. 13/573,516, filed on Sep. 19, 2012, now Pat. No. 9,918,745, and a continuation-in-part of application No. 13/573,303, filed on Sep. 7, 2012, now Pat. No. 9,393,047, and a continuation-in-part of application No. 13/506,365, filed on Apr. 13, 2012, now Pat. No. 8,444,681, and a continuation-in-part of application No. 13/374,439, filed on Dec. 29, 2011, now Pat. No. 9,980,753, and a continuation-in-part of application No. 13/373,289, filed on Nov. 9, 2011, now Pat. No. 9,907,574, and a continuation-in-part of application No. 12/924,802, filed on Oct. 5, 2010, now Pat. No. 8,556,938, and a continuation-in-part of application No. 12/802,849, filed on Jun. 15, 2010, now abandoned.

(60) Provisional application No. 61/627,374, filed on Oct. 11, 2011, provisional application No. 61/626,250, filed on Sep. 23, 2011, provisional application No. 61/573,508, filed on Sep. 7, 2011, provisional application No. 61/517,088, filed on Apr. 13, 2011, provisional application No. 61/463,037, filed on Feb. 11, 2011, provisional application No. 61/460,267, filed on Dec. 29, 2010, provisional application No. 61/460,234, filed on Dec. 29, 2010, provisional application No. 61/456,649, filed on Nov. 10, 2010, provisional application No. 61/403,915, filed on Sep. 23, 2010, provisional application No. 61/403,696, filed on Sep. 20, 2010, provisional application No. 61/402,959, filed on Sep. 8, 2010, provisional application No. 61/400,504, filed on Jul. 29, 2010, provisional application No. 61/398,807, filed on Jul. 1, 2010, provisional application No. 61/395,564, filed on May 14, 2010, provisional application No. 61/343,737, filed on May 3, 2010, provisional application No. 61/278,240, filed on Oct. 5, 2009, provisional application No. 61/396,390, filed on May 26, 2010, provisional application No. 61/395,752, filed on May 17, 2010, provisional application No. 61/395,564, filed on May 14, 2010, provisional application No. 61/336,911, filed on Jan. 28, 2010, provisional application No. 61/270,754, filed on Jul. 13, 2009, provisional application No. 61/268,708, filed on Jun. 15, 2009.

(51) Int. Cl.
*A61B 17/56* (2006.01)
*A61B 90/00* (2016.01)
*A61B 17/68* (2006.01)

(52) U.S. Cl.
CPC ...... *A61B 17/7008* (2013.01); *A61B 17/7038* (2013.01); *A61B 17/7082* (2013.01); *A61B 17/7091* (2013.01); *A61B 17/864* (2013.01); *A61B 2017/567* (2013.01); *A61B 2017/681* (2013.01); *A61B 2090/0808* (2016.02); *Y10T 29/49826* (2015.01)

(58) Field of Classification Search
USPC .................................. 606/246–289, 300–328
See application file for complete search history.

(56) References Cited

U.S. PATENT DOCUMENTS

| | | |
|---|---|---|
| 5,672,176 A | 9/1997 | Biedermann et al. |
| 5,735,853 A | 4/1998 | Olerud |
| 5,891,145 A | 4/1999 | Morrison et al. |
| 6,063,090 A | 5/2000 | Schlapfer |
| 6,146,383 A | 11/2000 | Studer et al. |
| 6,241,731 B1 | 6/2001 | Fiz |
| 6,280,442 B1 | 8/2001 | Barker et al. |
| 6,626,908 B2 | 9/2003 | Cooper et al. |
| 6,648,888 B1 | 11/2003 | Shluzas |
| 6,660,004 B2 | 12/2003 | Barker et al. |
| 6,716,214 B1 | 4/2004 | Jackson |
| 6,740,086 B2 | 5/2004 | Richelsoph |
| 6,837,889 B2 | 1/2005 | Shluzas |
| 7,001,389 B1 | 2/2006 | Navarro et al. |
| 7,066,937 B2 | 6/2006 | Shluzas |
| 7,087,057 B2 | 8/2006 | Konieczynski et al. |
| 7,160,300 B2 | 1/2007 | Jackson |
| 7,179,261 B2 | 2/2007 | Sicvol et al. |
| 7,186,255 B2 | 3/2007 | Baynham |
| 7,306,606 B2 | 12/2007 | Sasing |
| 7,322,981 B2 | 1/2008 | Jackson |
| 7,377,923 B2 | 5/2008 | Purcell et al. |
| 7,491,218 B2 | 2/2009 | Landry et al. |
| 7,530,992 B2 | 5/2009 | Biedermann et al. |
| 7,618,444 B2 | 11/2009 | Shluzas |
| 7,625,396 B2 | 12/2009 | Jackson |
| 7,686,835 B2 | 3/2010 | Warnick |
| 7,749,258 B2 | 7/2010 | Biedermann et al. |
| 7,766,945 B2 | 8/2010 | Nilsson et al. |
| 7,776,067 B2 | 8/2010 | Jackson |
| 7,833,251 B1 | 11/2010 | Ahlgren et al. |
| 7,857,834 B2 | 12/2010 | Boschert |
| 7,875,065 B2 | 1/2011 | Jackson |
| 7,922,748 B2 | 4/2011 | Hoffman |
| 7,947,065 B2 | 5/2011 | Hammill et al. |
| 8,021,397 B2 | 9/2011 | Farris et al. |
| 8,034,089 B2 | 10/2011 | Matthis et al. |
| 8,048,112 B2 | 11/2011 | Suziki et al. |
| 8,048,126 B2 | 11/2011 | Altarac et al. |
| 8,066,744 B2 | 11/2011 | Justis et al. |
| 8,075,599 B2 | 12/2011 | Johnson |
| 8,100,946 B2 | 1/2012 | Strasbaugh et al. |
| 8,133,262 B2 | 3/2012 | Whipple |
| 8,137,386 B2 | 3/2012 | Jackson |
| 8,206,422 B2 | 6/2012 | Hestad et al. |
| 8,277,485 B2 | 10/2012 | Krishna et al. |
| 8,361,129 B2 | 1/2013 | Chao |
| 8,377,102 B2 | 2/2013 | Jackson |
| 8,382,805 B2 | 2/2013 | Wang et al. |
| 8,385,205 B2 | 2/2013 | Wang |
| 8,430,914 B2 | 4/2013 | Spratt et al. |
| 8,444,681 B2 | 5/2013 | Jackson et al. |
| 8,449,578 B2 | 5/2013 | Keiser et al. |
| 8,506,609 B2 | 8/2013 | Biedermann et al. |
| 8,591,558 B2 | 11/2013 | Matthis et al. |
| 8,771,324 B2 | 7/2014 | Black |
| 8,814,913 B2 | 8/2014 | Jackson |
| 8,876,869 B1 | 11/2014 | Schafer et al. |
| 8,888,827 B2 | 11/2014 | Harper et al. |
| 8,926,671 B2 | 1/2015 | Biedermann |
| 8,986,349 B1 * | 3/2015 | German ............ A61B 17/7068 606/279 |
| 9,044,272 B2 | 6/2015 | Shaffrey et al. |
| 9,155,567 B2 | 10/2015 | Auerbach et al. |
| 9,168,069 B2 | 10/2015 | Jackson |
| 9,198,694 B2 | 12/2015 | Mishra et al. |
| 9,254,150 B2 | 2/2016 | Biedermann et al. |
| 9,358,047 B2 | 6/2016 | Mishra et al. |
| 9,393,047 B2 | 7/2016 | Jackson et al. |
| 9,439,681 B2 | 9/2016 | Keyer et al. |

(56) References Cited

U.S. PATENT DOCUMENTS

| | | |
|---|---|---|
| 9,456,853 B2 | 10/2016 | Jackson |
| 9,480,517 B2 | 11/2016 | Jackson et al. |
| 9,504,496 B2 | 11/2016 | Jackson et al. |
| 9,572,599 B1 | 2/2017 | Casey et al. |
| 9,717,534 B2 | 8/2017 | Jackson et al. |
| 9,763,698 B2 | 9/2017 | Biedermann et al. |
| 9,883,892 B2 | 2/2018 | Jackson et al. |
| 9,895,172 B2 | 2/2018 | Biedermann et al. |
| 9,907,574 B2 | 3/2018 | Jackson et al. |
| 9,918,745 B2 | 3/2018 | Jackson |
| 9,956,006 B2 | 5/2018 | Jackson |
| 9,980,753 B2 | 5/2018 | Jackson |
| 10,028,770 B2 | 7/2018 | Rezach et al. |
| 10,039,572 B2 | 8/2018 | Harris et al. |
| 10,172,649 B2 | 1/2019 | Jackson et al. |
| 10,179,010 B2 | 1/2019 | Jackson et al. |
| 10,238,431 B2 | 3/2019 | Jackson et al. |
| 10,251,677 B2 * | 4/2019 | Heuer ............... A61B 17/7032 |
| 10,278,738 B2 | 5/2019 | Jackson et al. |
| 10,363,070 B2 | 7/2019 | Jackson et al. |
| 10,398,475 B2 | 9/2019 | Jackson et al. |
| 10,441,319 B2 | 10/2019 | Jackson |
| 10,456,173 B1 | 10/2019 | Casey et al. |
| 10,478,225 B2 | 11/2019 | Jackson et al. |
| 10,765,455 B2 | 9/2020 | Jackson et al. |
| 10,765,456 B2 | 9/2020 | Jackson et al. |
| 10,813,671 B2 | 10/2020 | Jackson et al. |
| 10,813,672 B2 | 10/2020 | Jackson et al. |
| 2002/0022842 A1 | 2/2002 | Horvath et al. |
| 2002/0026193 A1 | 2/2002 | Barker et al. |
| 2002/0133159 A1 | 9/2002 | Jackson |
| 2002/0143341 A1 | 10/2002 | Biedermann et al. |
| 2002/0193794 A1 | 12/2002 | Taylor |
| 2004/0039383 A1 | 2/2004 | Jackson |
| 2004/0049196 A1 | 3/2004 | Jackson |
| 2004/0167526 A1 | 8/2004 | Jackson |
| 2004/0267264 A1 | 12/2004 | Konieczynski et al. |
| 2005/0080415 A1 | 4/2005 | Keyer et al. |
| 2005/0187548 A1 | 8/2005 | Butler et al. |
| 2005/0228379 A1 | 10/2005 | Jackson |
| 2005/0240180 A1 | 10/2005 | Vienney |
| 2005/0261687 A1 | 11/2005 | Garamszegi |
| 2006/0025771 A1 | 2/2006 | Jackson |
| 2006/0036252 A1 | 2/2006 | Baynham et al. |
| 2006/0058788 A1 | 3/2006 | Hammer |
| 2006/0155277 A1 | 7/2006 | Metz-Stavenhagen |
| 2006/0173454 A1 | 8/2006 | Spitler et al. |
| 2006/0200131 A1 | 9/2006 | Chao et al. |
| 2006/0217716 A1 | 9/2006 | Baker |
| 2006/0293664 A1 | 12/2006 | Schumacher |
| 2007/0088357 A1 | 4/2007 | Johnson et al. |
| 2007/0090238 A1 | 4/2007 | Justis |
| 2007/0093826 A1 | 4/2007 | Hawkes et al. |
| 2007/0093827 A1 | 4/2007 | Warnick |
| 2007/0118117 A1 | 5/2007 | Altarac et al. |
| 2007/0118123 A1 | 5/2007 | Strausbaugh et al. |
| 2007/0123862 A1 | 5/2007 | Warnick |
| 2007/0161999 A1 | 7/2007 | Biedermann et al. |
| 2007/0233087 A1 | 10/2007 | Schlapfer |
| 2007/0270813 A1 | 11/2007 | Garamszegi |
| 2007/0270831 A1 | 11/2007 | Dewey et al. |
| 2008/0045953 A1 | 2/2008 | Garamszegi |
| 2008/0086132 A1 | 4/2008 | Biedermann et al. |
| 2008/0132957 A1 | 6/2008 | Matthis et al. |
| 2008/0140135 A1 | 6/2008 | Konieczynski et al. |
| 2008/0140136 A1 | 6/2008 | Jackson |
| 2008/0147129 A1 | 6/2008 | Biedermann et al. |
| 2008/0154315 A1 | 6/2008 | Jackson |
| 2008/0161863 A1 | 7/2008 | Arnold et al. |
| 2008/0215100 A1 | 9/2008 | Matthis et al. |
| 2008/0221681 A1 | 9/2008 | Trieu et al. |
| 2008/0234761 A1 | 9/2008 | Jackson |
| 2008/0269809 A1 | 10/2008 | Garamszegi |
| 2008/0294202 A1 | 11/2008 | Peterson et al. |
| 2008/0319490 A1 | 12/2008 | Jackson |
| 2009/0012567 A1 | 1/2009 | Biedermann et al. |
| 2009/0062865 A1 | 3/2009 | Schumacher |
| 2009/0062866 A1 | 3/2009 | Jackson |
| 2009/0062867 A1 | 3/2009 | Schumacher |
| 2009/0069852 A1 | 3/2009 | Farris et al. |
| 2009/0069853 A1 | 3/2009 | Schumacher |
| 2009/0105769 A1 | 4/2009 | Rock et al. |
| 2009/0105770 A1 | 4/2009 | Berrevoets et al. |
| 2009/0204155 A1 | 8/2009 | Aschmann |
| 2009/0240290 A1 | 9/2009 | Choi |
| 2010/0004692 A1 | 1/2010 | Biedermann |
| 2010/0023061 A1 | 1/2010 | Randol et al. |
| 2010/0087865 A1 | 4/2010 | Biedermann et al. |
| 2010/0094343 A1 | 4/2010 | Pham et al. |
| 2010/0094349 A1 | 4/2010 | Hammer et al. |
| 2010/0100137 A1 | 4/2010 | Justis et al. |
| 2010/0114170 A1 | 5/2010 | Barrus et al. |
| 2010/0152787 A1 | 6/2010 | Walsh et al. |
| 2010/0198272 A1 | 8/2010 | Keyer et al. |
| 2010/0234902 A1 | 9/2010 | Biedermann et al. |
| 2010/0256686 A1 | 10/2010 | Fisher |
| 2010/0262195 A1 | 10/2010 | Jackson |
| 2010/0274288 A1 | 10/2010 | Prevost et al. |
| 2010/0298891 A1 | 11/2010 | Jackson |
| 2010/0305621 A1 | 12/2010 | Wang et al. |
| 2011/0040338 A1 | 2/2011 | Jackson |
| 2011/0196430 A1 | 8/2011 | Walsh et al. |
| 2011/0213424 A1 | 9/2011 | Biedermann et al. |
| 2011/0282399 A1 | 11/2011 | Jackson |
| 2012/0010661 A1 | 1/2012 | Farris et al. |
| 2012/0035670 A1 | 2/2012 | Jackson et al. |
| 2012/0041490 A1 | 2/2012 | Jacob et al. |
| 2012/0046699 A1 | 2/2012 | Jones et al. |
| 2012/0046700 A1 | 2/2012 | Jackson et al. |
| 2012/0078307 A1 | 3/2012 | Nihalani |
| 2012/0150239 A1 | 6/2012 | Garamszegi |
| 2012/0165881 A1 | 6/2012 | Biedermann et al. |
| 2012/0165882 A1 | 6/2012 | Biedermann et al. |
| 2012/0179210 A1 | 7/2012 | Garamszegi |
| 2012/0179212 A1 | 7/2012 | Jackson et al. |
| 2012/0265257 A1 | 10/2012 | Jackson |
| 2012/0303070 A1 | 11/2012 | Jackson |
| 2012/0310284 A1 | 12/2012 | Gerchow |
| 2012/0310290 A1 | 12/2012 | Jackson |
| 2013/0018428 A1 | 1/2013 | Harper et al. |
| 2013/0046345 A1 | 2/2013 | Jones et al. |
| 2013/0338721 A1 | 2/2013 | Biedermann et al. |
| 2013/0060292 A1 | 3/2013 | Jackson |
| 2013/0072981 A1 | 3/2013 | Jackson |
| 2013/0079830 A1 | 3/2013 | Garamszegi et al. |
| 2013/0096620 A1 | 4/2013 | Biedermann et al. |
| 2013/0096621 A1 | 4/2013 | Biedermann et al. |
| 2013/0096622 A1 | 4/2013 | Biedermann et al. |
| 2013/0103098 A1 | 4/2013 | Jackson et al. |
| 2013/0123861 A1 | 5/2013 | Biedermann et al. |
| 2013/0131730 A1 | 5/2013 | Jackson et al. |
| 2013/0144346 A1 | 6/2013 | Jackson et al. |
| 2013/0150852 A1 | 6/2013 | Shluzas et al. |
| 2013/0211465 A1 | 8/2013 | Savage |
| 2013/0268006 A1 | 10/2013 | Garamszegi |
| 2013/0345756 A1 | 12/2013 | Berrevoets et al. |
| 2014/0058454 A1 | 2/2014 | Hammer |
| 2014/0081334 A1 | 3/2014 | Jackson |
| 2014/0128927 A1 | 5/2014 | Jackson |
| 2014/0135854 A1 | 5/2014 | Dec et al. |
| 2014/0163619 A1 | 6/2014 | Harvey |
| 2014/0172018 A1 | 6/2014 | Gephart et al. |
| 2014/0172023 A1 | 6/2014 | Garamszegi |
| 2014/0188173 A1 | 7/2014 | Mishra et al. |
| 2014/0188175 A1 | 7/2014 | Mishra et al. |
| 2014/0303675 A1 | 10/2014 | Mishra |
| 2014/0379031 A1 | 12/2014 | Biedermann et al. |
| 2015/0182260 A1 | 7/2015 | Jackson et al. |
| 2015/0223844 A1 | 8/2015 | Left et al. |
| 2015/0374413 A1 | 12/2015 | Spangler et al. |
| 2016/0045228 A1 | 2/2016 | Biedermann et al. |
| 2016/0220280 A1 | 8/2016 | Jackson |
| 2016/0302831 A1 | 10/2016 | Nichols et al. |
| 2016/0367293 A1 | 12/2016 | Keyer et al. |

(56) References Cited

U.S. PATENT DOCUMENTS

| | | |
|---|---|---|
| 2017/0119437 A1 | 5/2017 | Harper et al. |
| 2017/0128104 A1 | 5/2017 | Nichols et al. |
| 2017/0135729 A1 | 5/2017 | Garamszegi |
| 2017/0172627 A1 | 6/2017 | Kruger |
| 2017/0189074 A1 | 7/2017 | Biedermann et al. |
| 2017/0224386 A1 | 8/2017 | Left et al. |
| 2017/0245897 A1 | 8/2017 | Nichols et al. |
| 2017/0265902 A1 | 9/2017 | Jackson |
| 2017/0354443 A1 | 12/2017 | Jackson |
| 2018/0000523 A1 | 1/2018 | Jackson |
| 2018/0014859 A1 | 1/2018 | Biedermann et al. |
| 2018/0098795 A1 | 4/2018 | Jackson |
| 2018/0263665 A1 | 9/2018 | Yacoub et al. |
| 2018/0325558 A1 | 11/2018 | Yacoub et al. |
| 2018/0360499 A9 | 12/2018 | Jackson |
| 2019/0059953 A1 | 2/2019 | Keyer |
| 2019/0117271 A1 | 4/2019 | Jackson et al. |
| 2019/0216511 A1 | 7/2019 | Jackson et al. |
| 2019/0247093 A1 | 8/2019 | Jackson et al. |
| 2019/0247094 A1 | 8/2019 | Yacoub et al. |
| 2019/0282278 A1 | 9/2019 | Schlapfer et al. |
| 2019/0307489 A1 | 10/2019 | Jackson et al. |
| 2019/0365425 A1 | 12/2019 | Casey et al. |
| 2020/0030004 A1 | 1/2020 | Jackson et al. |
| 2020/0069337 A1 | 3/2020 | Jackson et al. |
| 2020/0352608 A1 | 11/2020 | Jackson et al. |
| 2021/0186571 A1 | 3/2021 | Jackson et al. |
| 2021/0106362 A1 | 4/2021 | Jackson et al. |
| 2021/0030446 A1 | 6/2021 | Jackson et al. |
| 2021/0161565 A1 | 6/2021 | Jackson et al. |
| 2021/0186564 A1 | 6/2021 | Jackson et al. |

\* cited by examiner

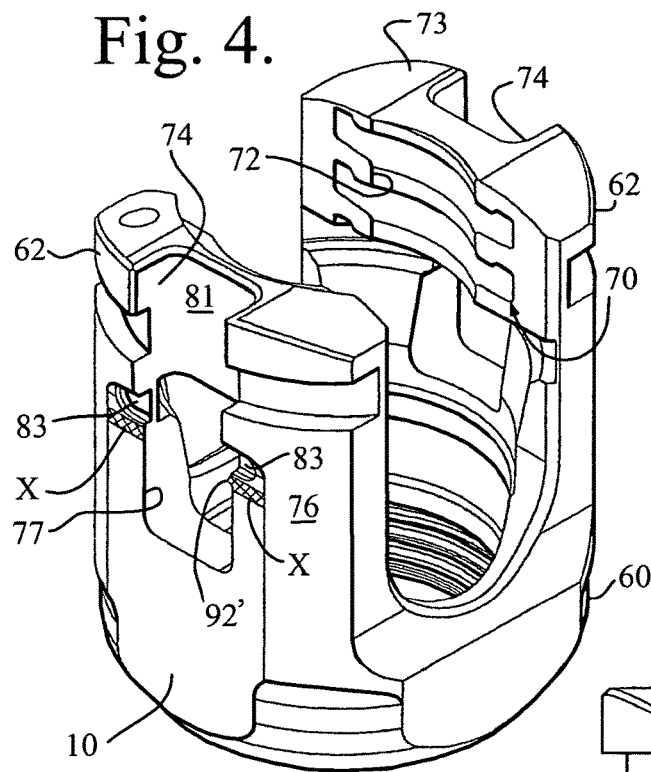
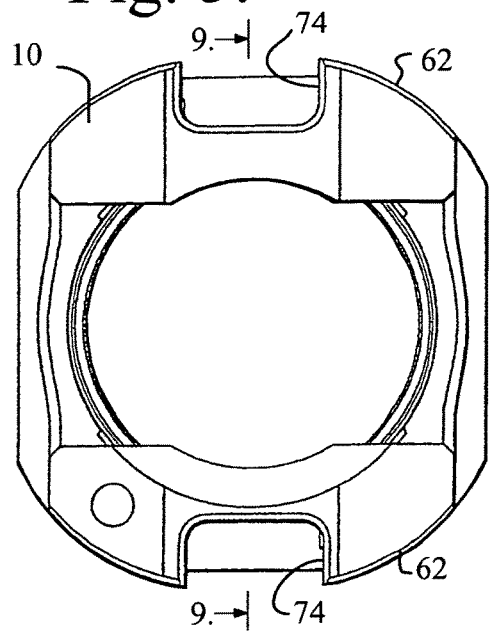
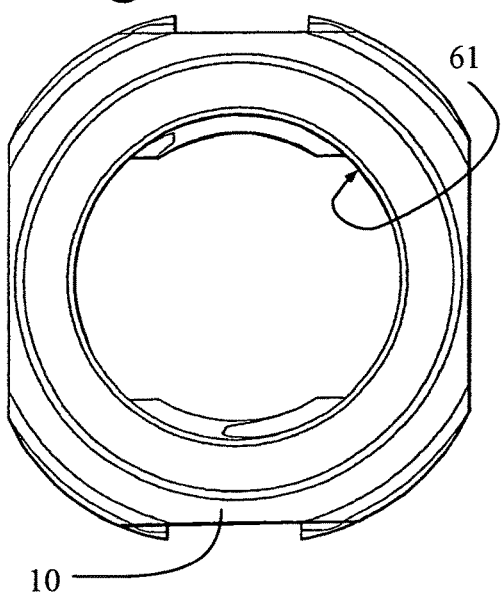
Fig. 4.
Fig. 5.
Fig. 6.
Fig. 7.

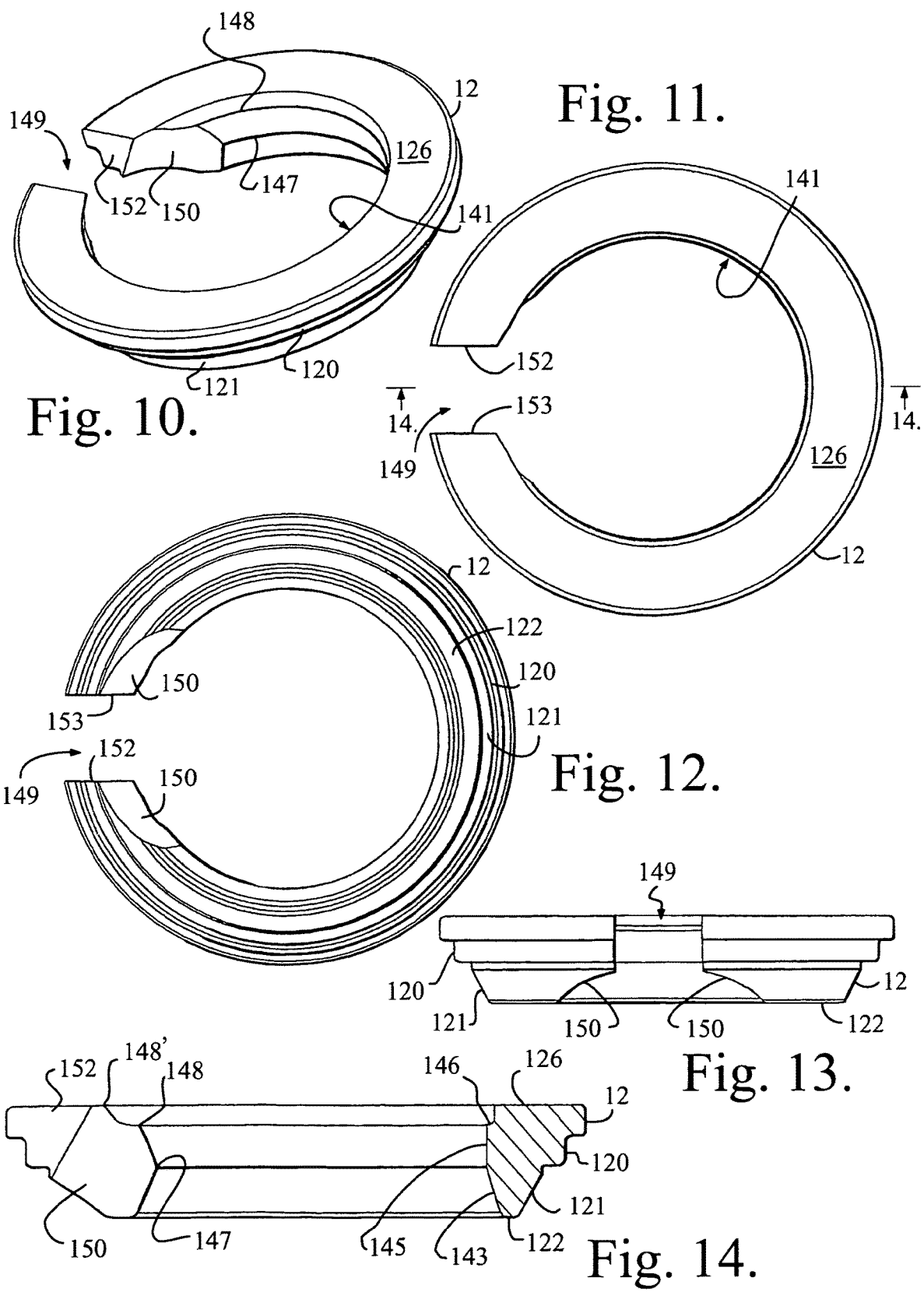

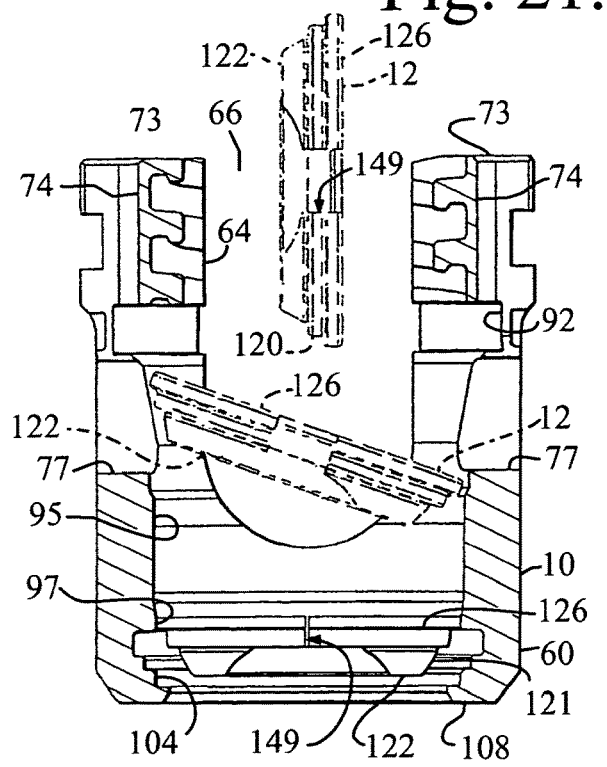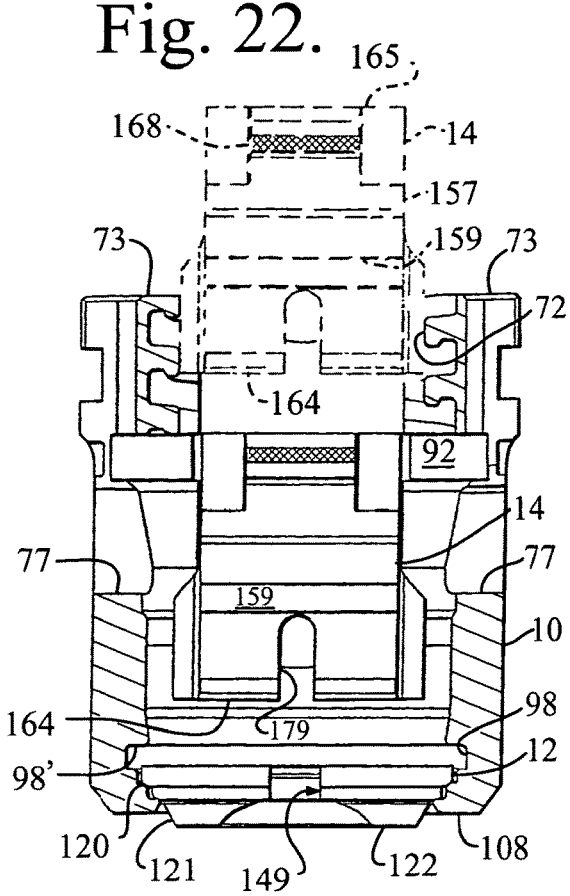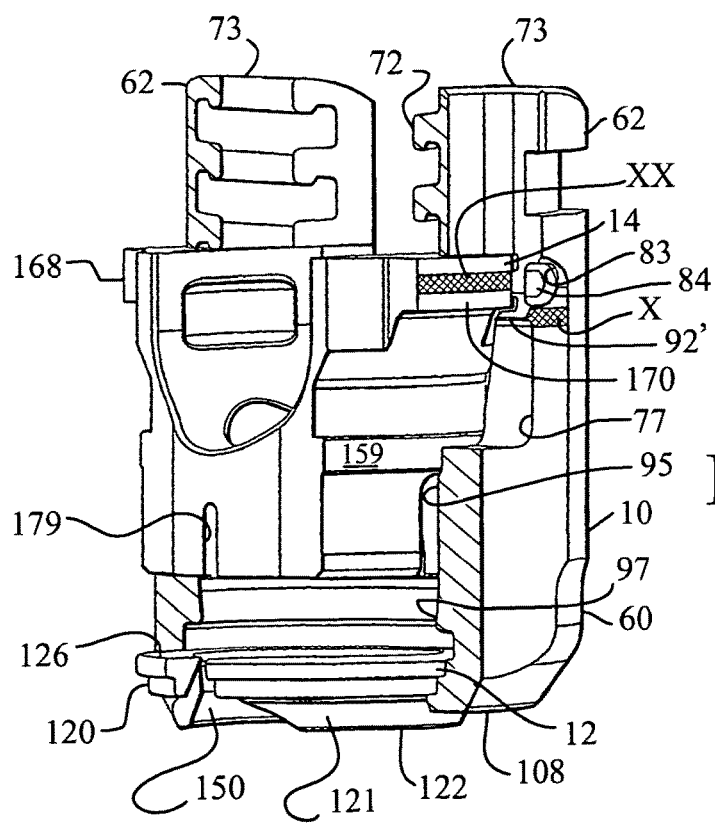

Fig. 24.
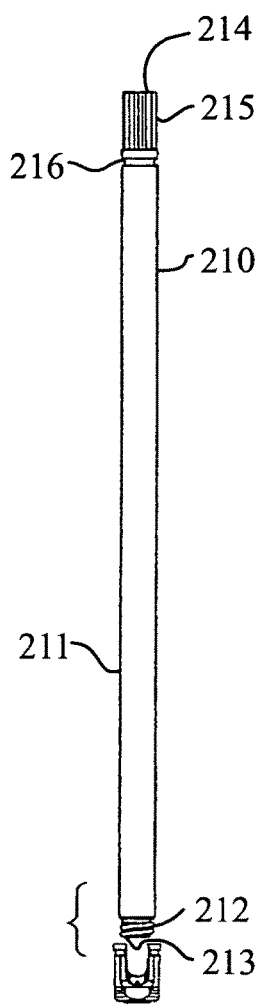
Fig. 25.
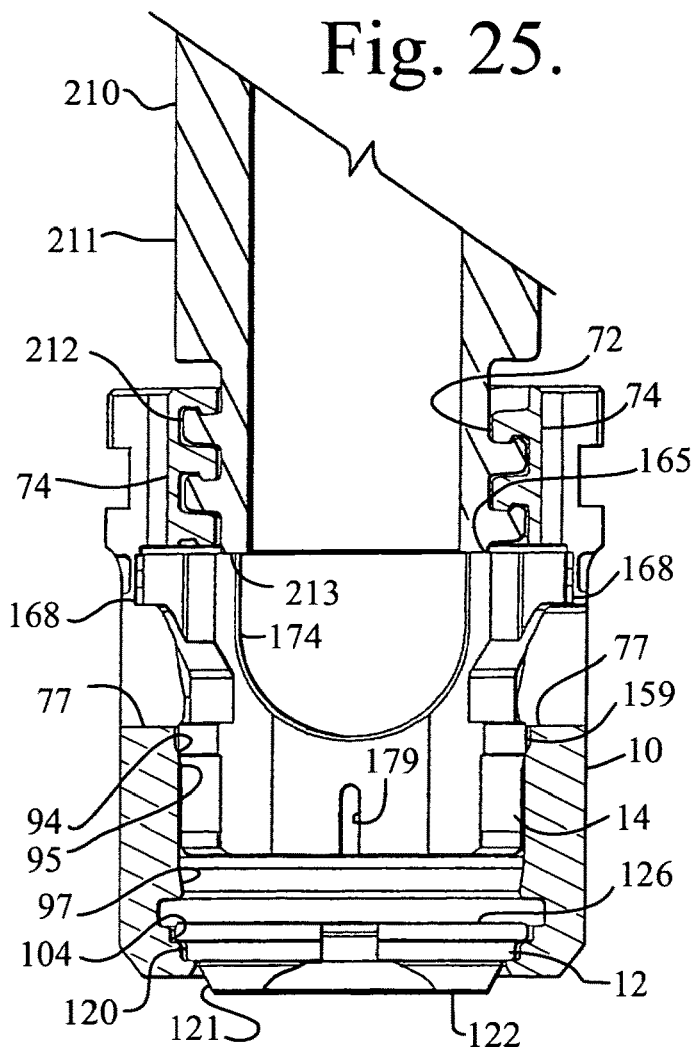
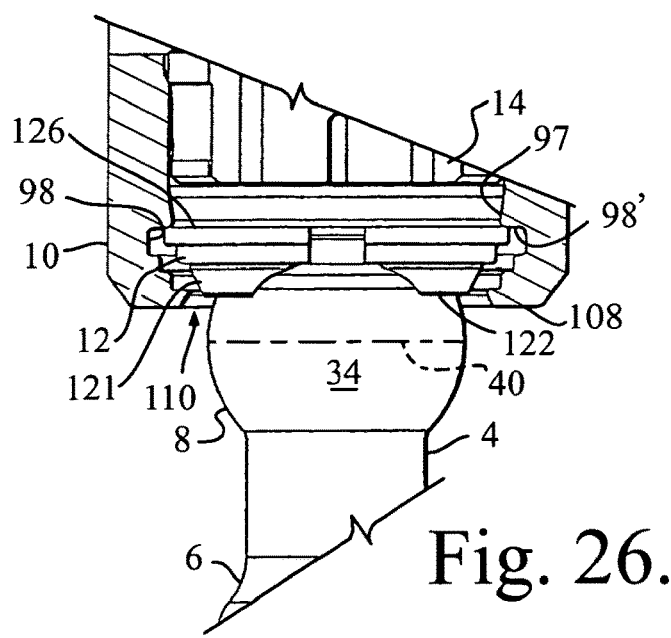
Fig. 26.

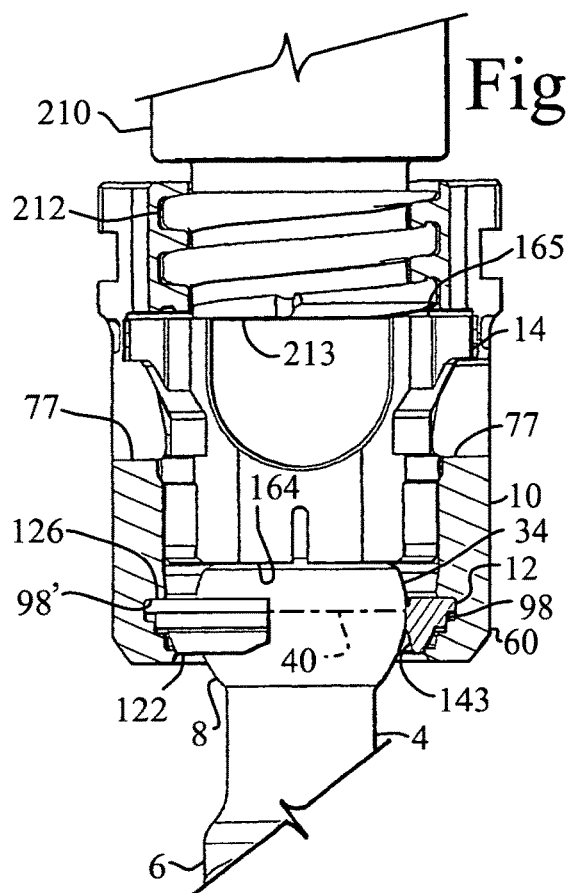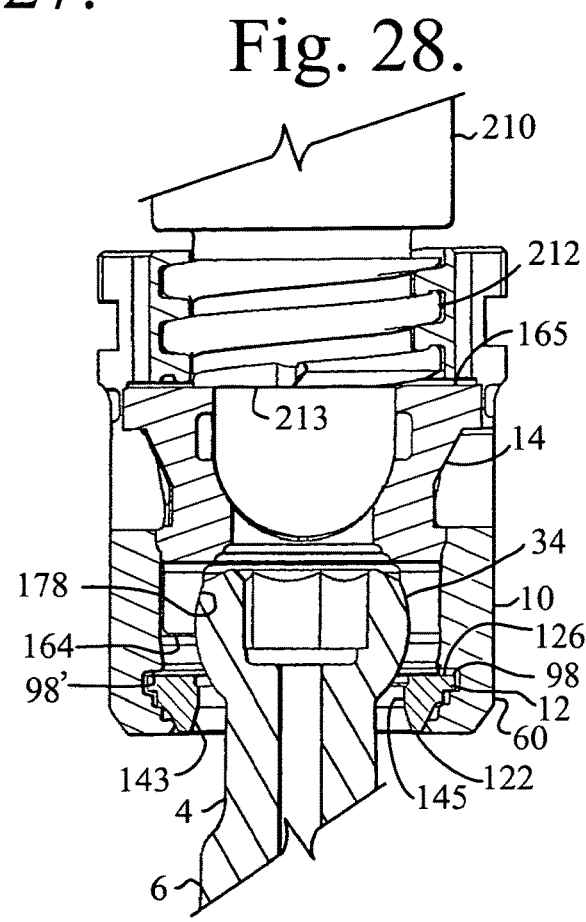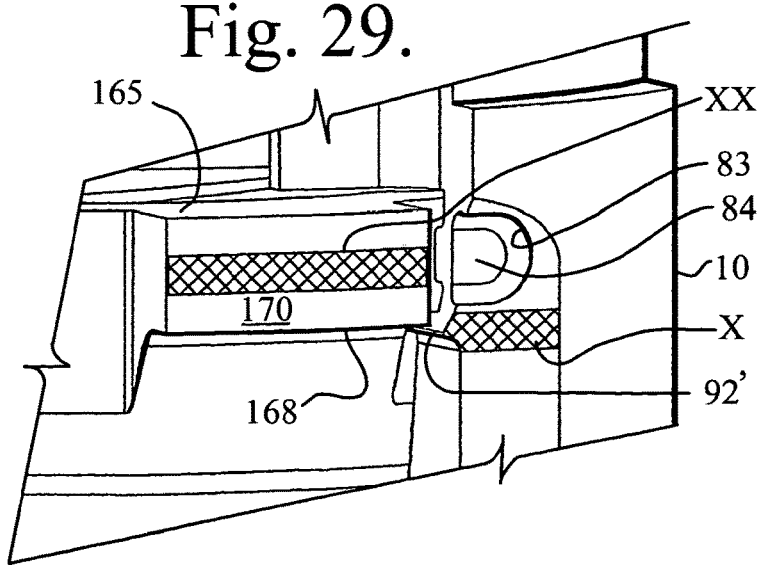

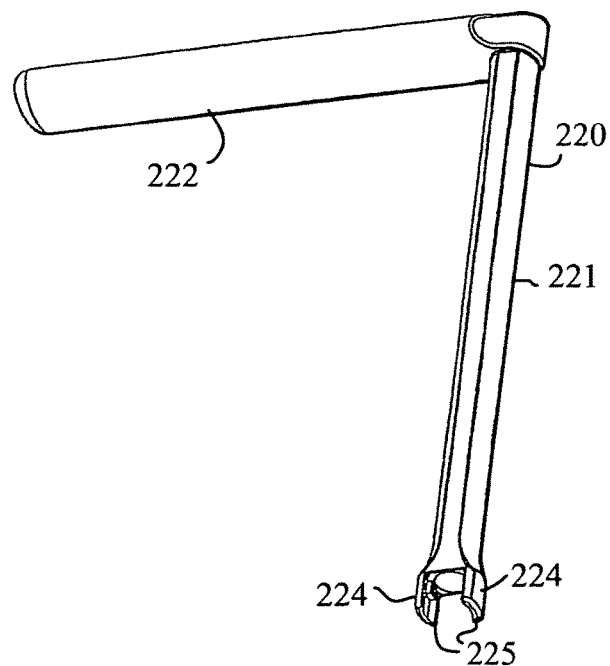
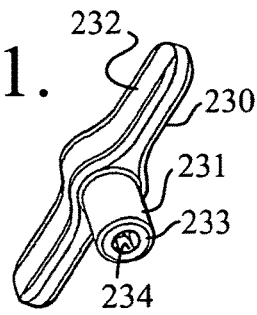
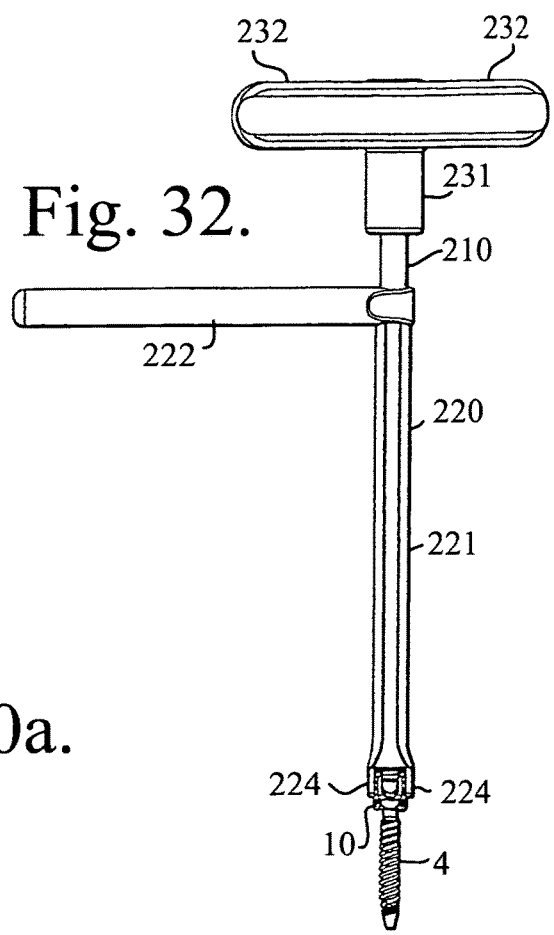
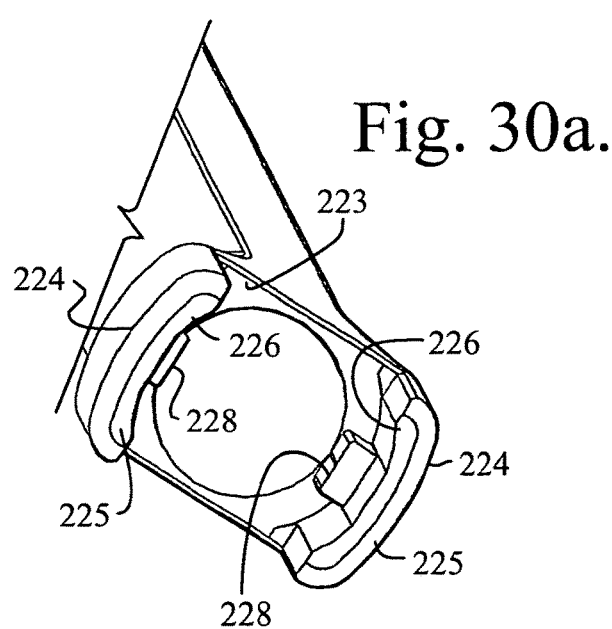
Fig. 30.
Fig. 31.
Fig. 32.
Fig. 30a.

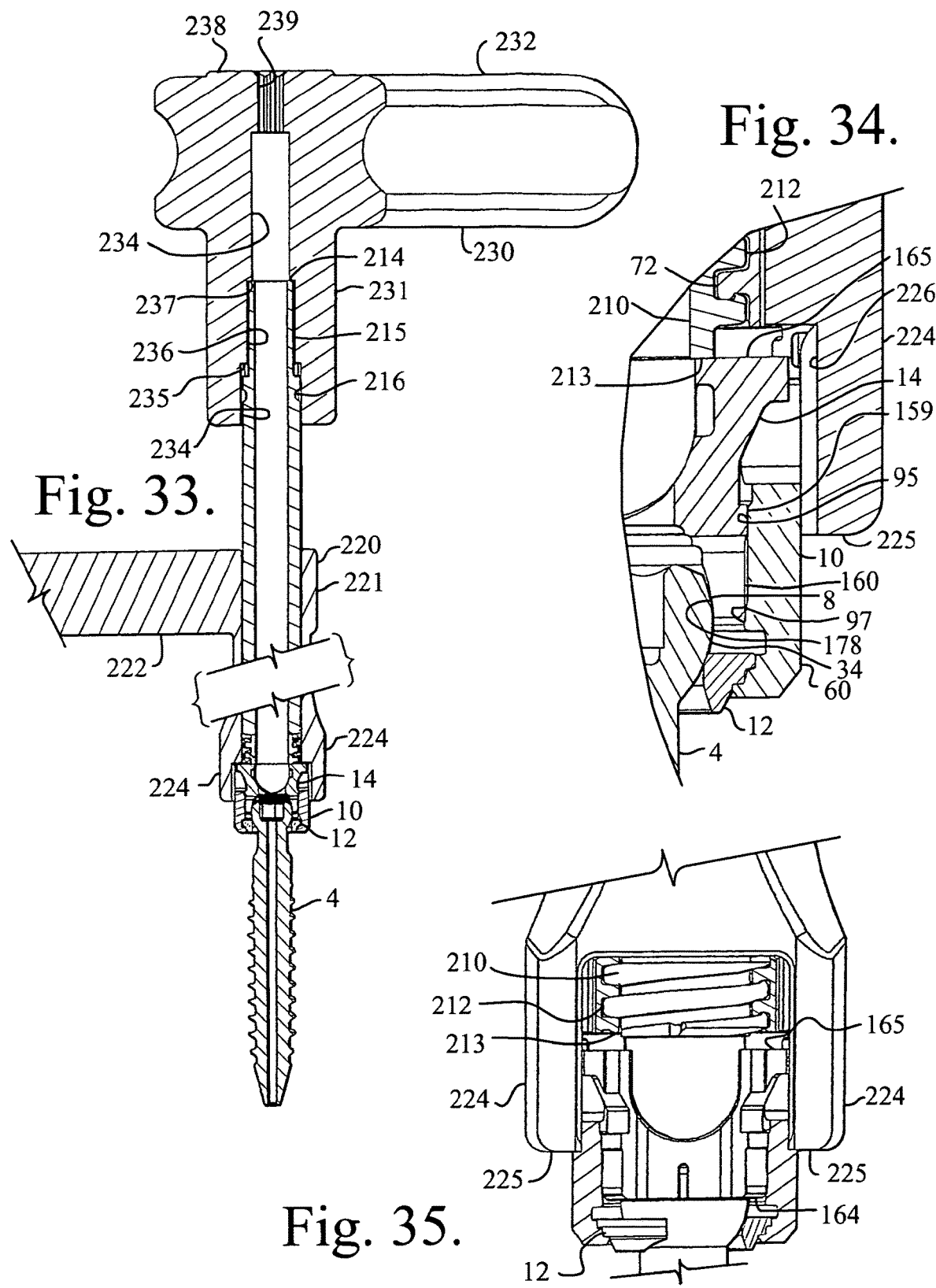

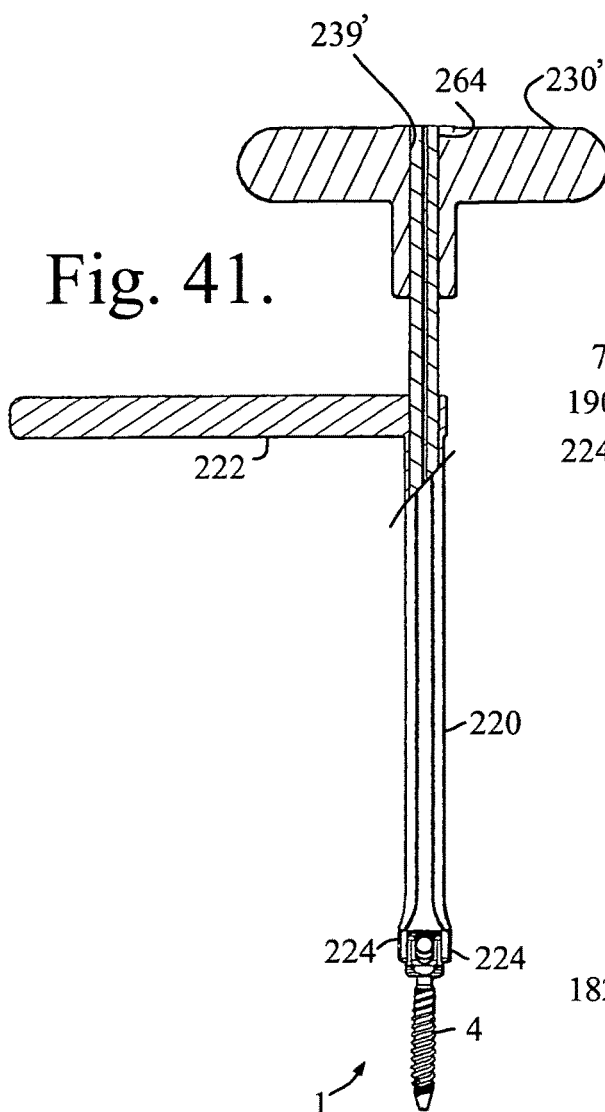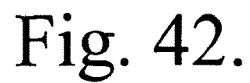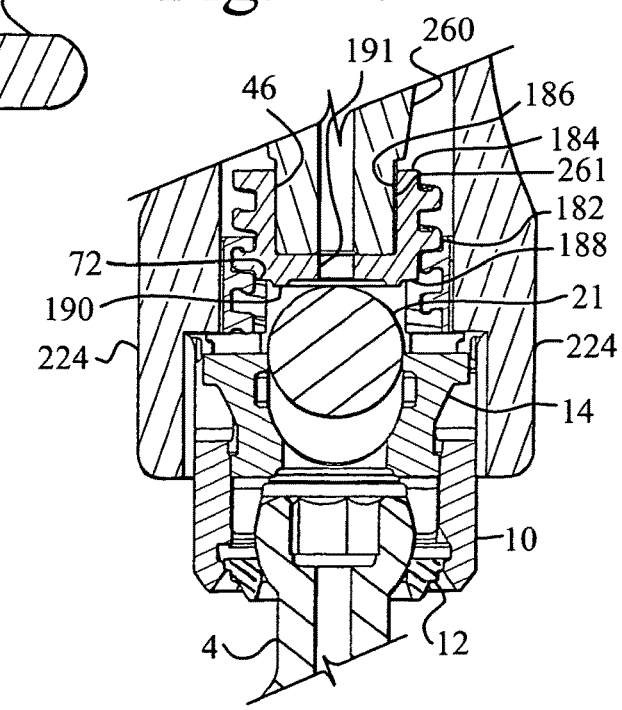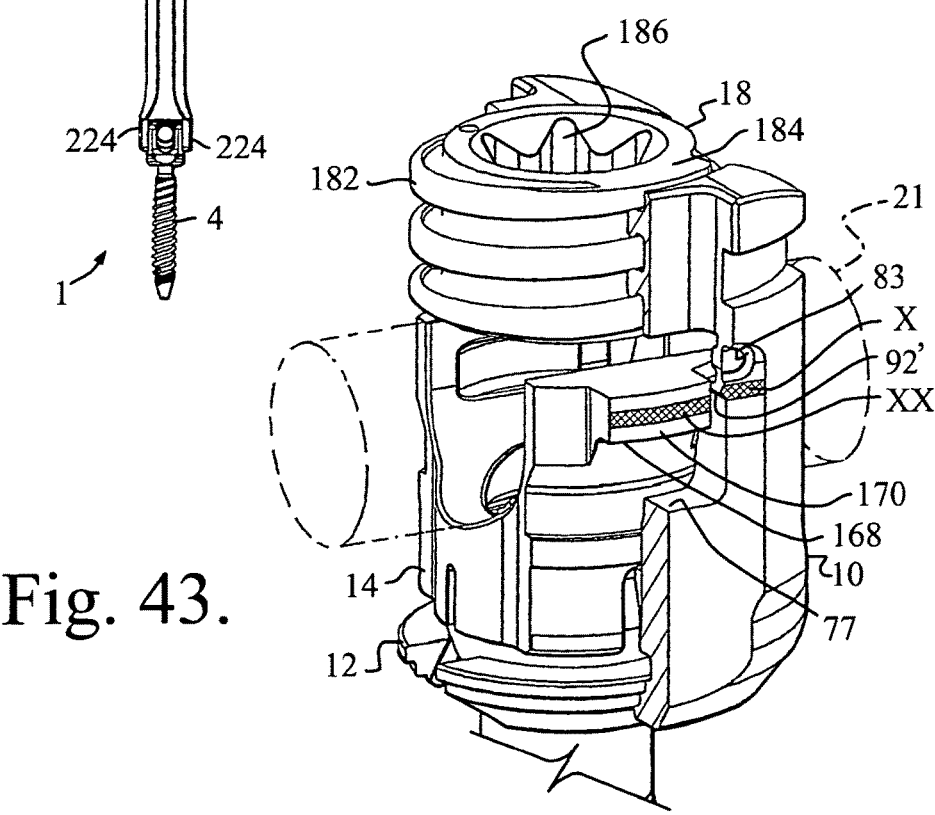

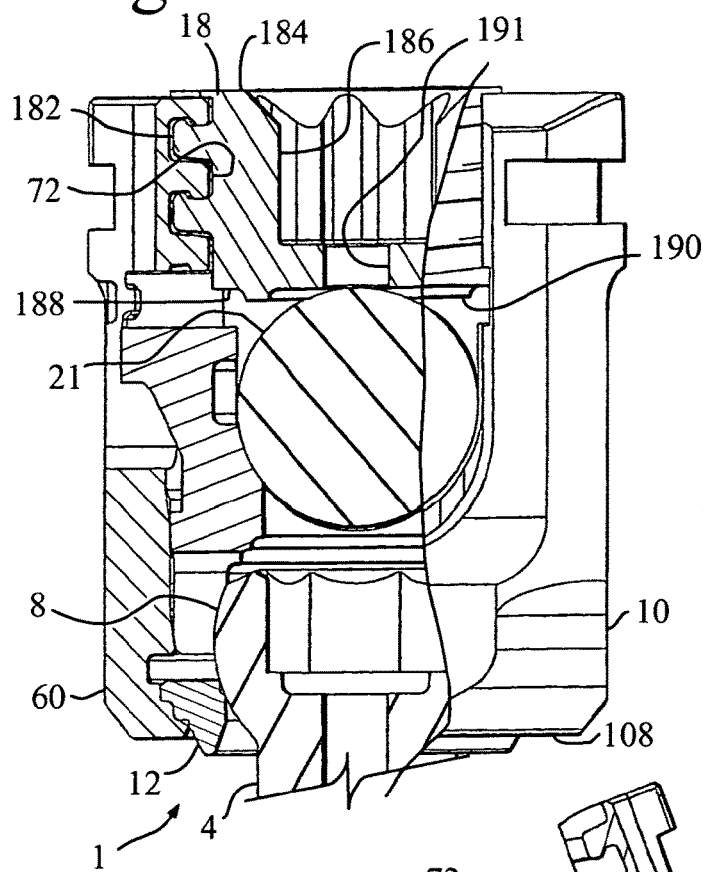
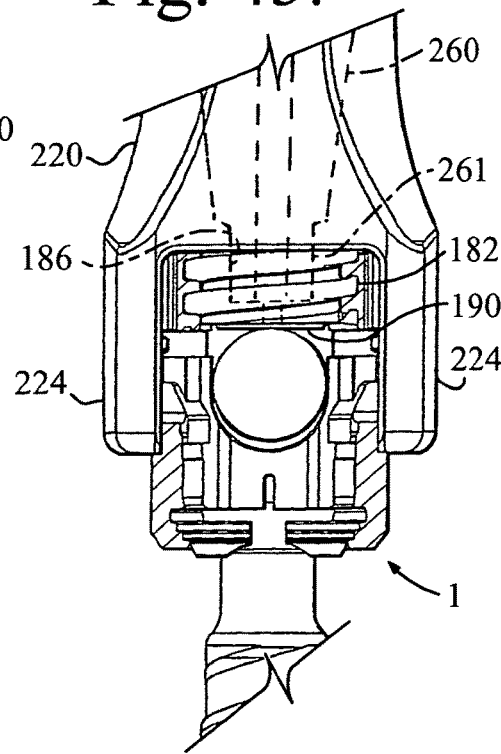
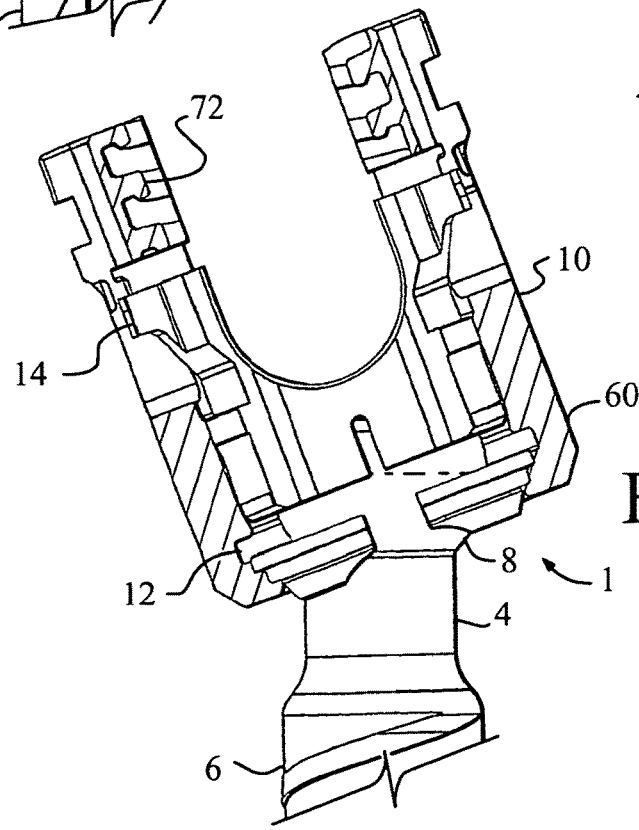
Fig. 44.
Fig. 45.
Fig. 46.

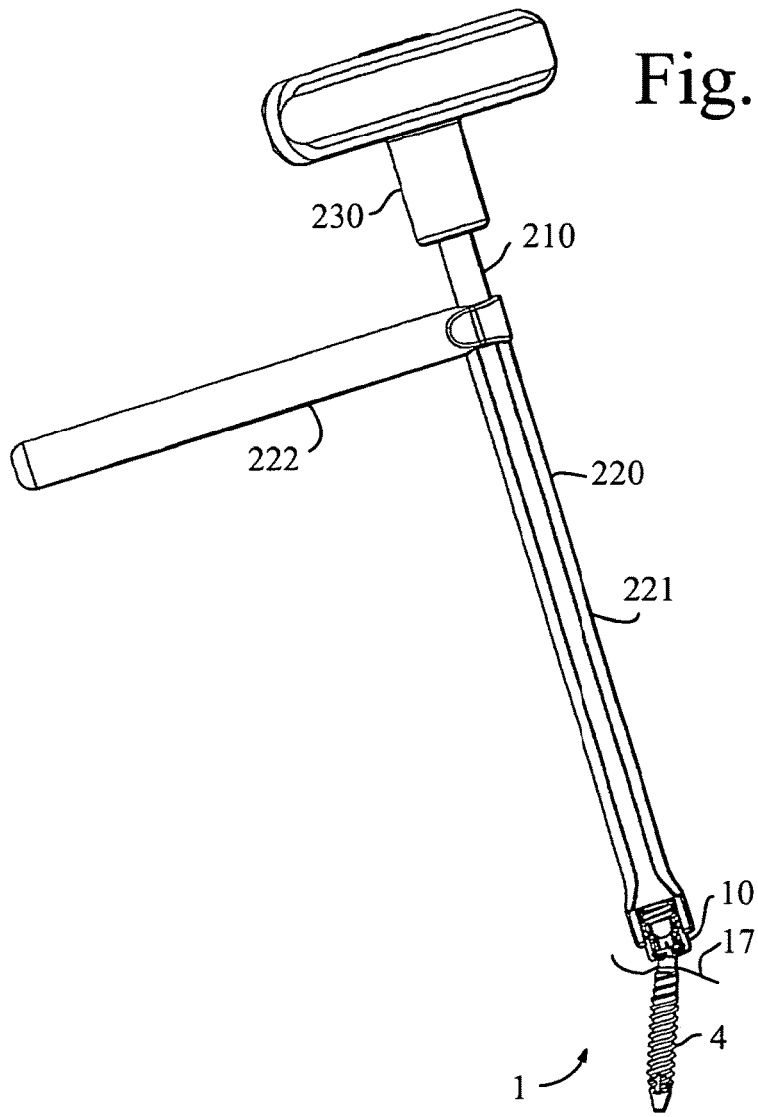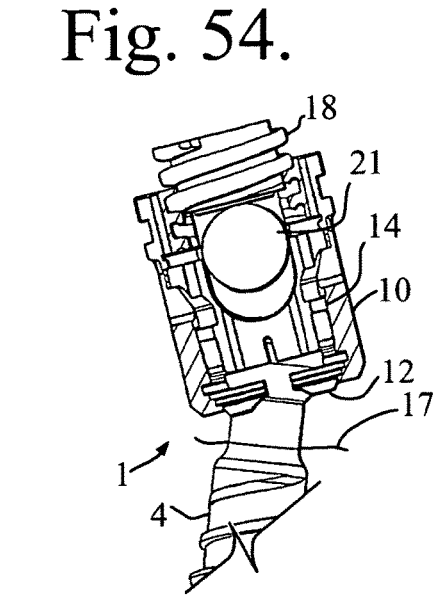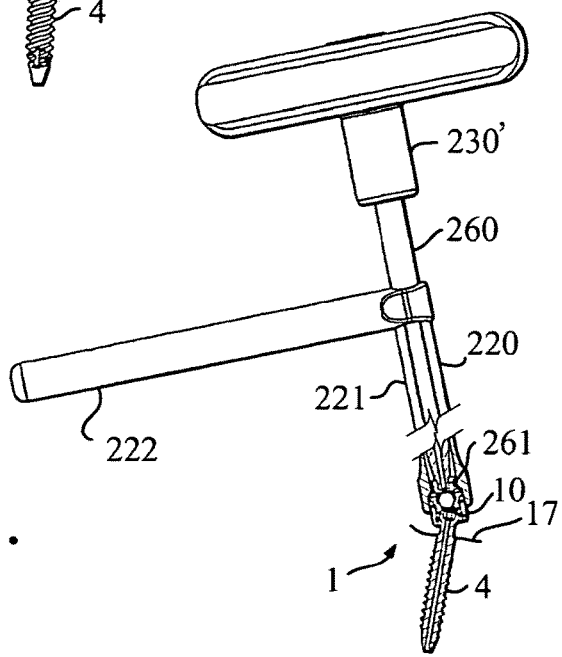
Fig. 53.
Fig. 54.
Fig. 55.

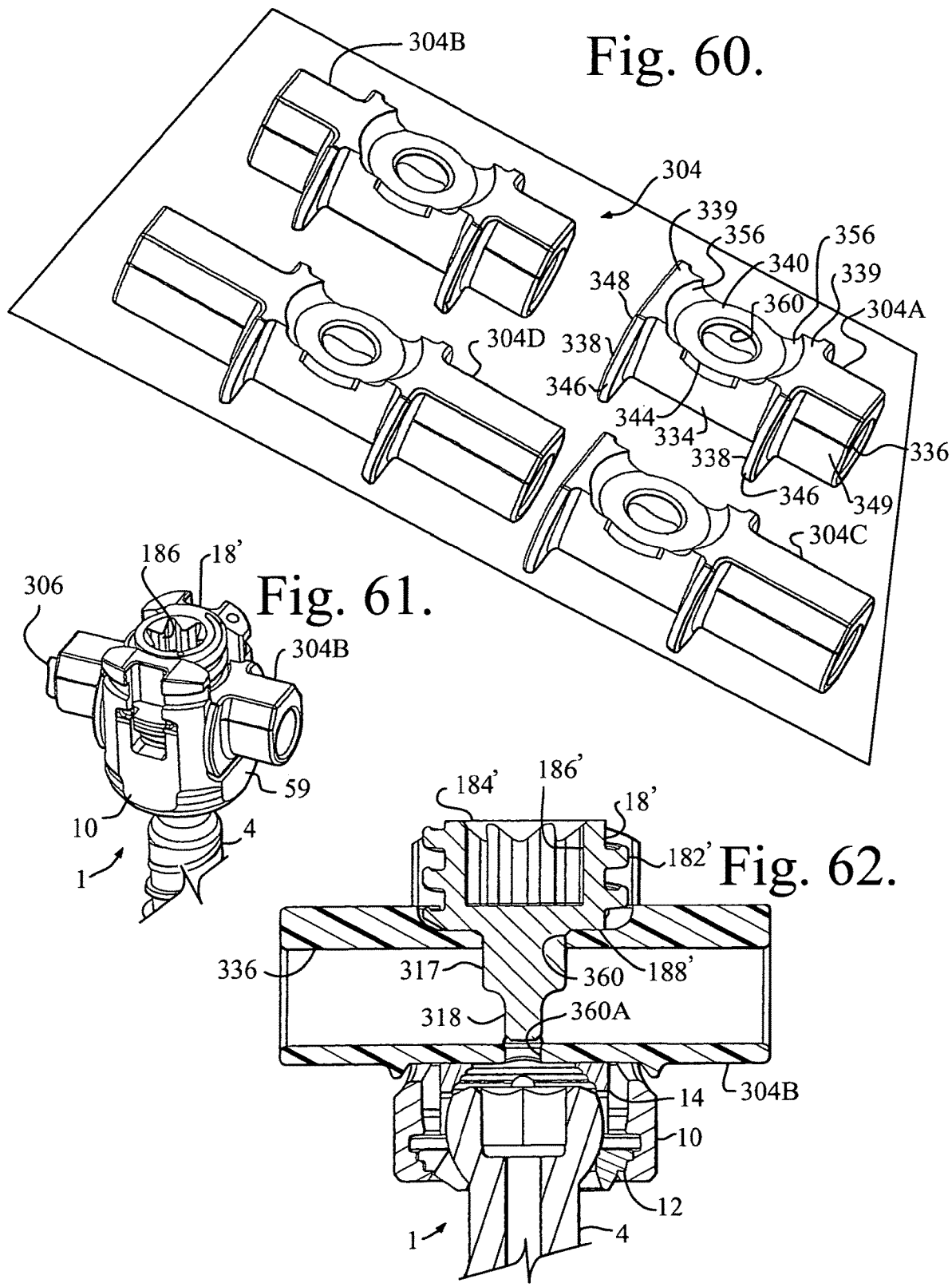

PIVOTAL BONE ANCHOR SYSTEM WITH UNIVERSAL SHANK HEAD

CROSS-REFERENCE TO RELATED APPLICATIONS

This application is a continuation of U.S. application Ser. No. 16/522,426 filed Jul. 25, 2019, which is a continuation of U.S. application Ser. No. 16/040,258 filed Jul. 19, 2018, now U.S. Pat. No. 10,398,475, which is a continuation-in-part of U.S. application Ser. No. 15/878,542 filed Jan. 24, 2018, now U.S. Pat. No. 10,172,649, which is a continuation-in-part of U.S. application Ser. No. 15/338,817 filed Oct. 31, 2016 now U.S. Pat. No. 9,883,892, which is a continuation of U.S. application Ser. No. 13/573,874 filed Oct. 10, 2012 now U.S. Pat. No. 9,480,517, which claims the benefit of U.S. Provisional Application No. 61/627,374 filed Oct. 11, 2011, each of which is incorporated by reference in its entirely herein, and for all purposes.

U.S. application Ser. No. 13/573,874 is also a continuation-in-part of U.S. application Ser. No. 13/573,516 filed Sep. 19, 2012 now U.S. Pat. No. 9,918,745, which claims the benefit of U.S. Provisional Application No. 61/626,250 filed Sep. 23, 2011, each of which is incorporated by reference in its entirely herein, and for all purposes.

U.S. application Ser. No. 13/573,874 is also a continuation-in-part of U.S. application Ser. No. 13/573,303 filed Sep. 7, 2012, now U.S. Pat. No. 9,393,047, which claims the benefit of U.S. Provisional Application No. 61/573,508 filed Sep. 7, 2011, each of which is incorporated by reference in its entirely herein, and for all purposes.

U.S. application Ser. No. 13/573,874 is also a continuation-in-part of U.S. application Ser. No. 13/506,365 filed Apr. 13, 2012 now U.S. Pat. No. 8,444,681, which claims the benefit of U.S. Provisional Application No. 61/517,088 filed Apr. 13, 2011, each of which is incorporated by reference in its entirely herein, and for all purposes.

U.S. application Ser. No. 13/573,874 is also a continuation-in-part of U.S. application Ser. No. 13/374,439 filed Dec. 29, 2011 now U.S. Pat. No. 9,980,753, which claims the benefit of U.S. Provisional Application No. 61/460,267 filed Dec. 29, 2010 and U.S. Provisional Application No. 61/463,037 filed Feb. 11, 2011, each of which is incorporated by reference in its entirely herein, and for all purposes.

U.S. application Ser. No. 13/573,874 is also a continuation-in-part of U.S. application Ser. No. 13/373,289 filed Nov. 9, 2011 now U.S. Pat. No. 9,907,574, which claims the benefit of U.S. Provisional Application No. 61/456,649 filed Nov. 10, 2010 and U.S. Provisional Application No. 61/460,234 filed Dec. 29, 2010, each of which is incorporated by reference in its entirely herein, and for all purposes.

U.S. application Ser. No. 13/573,874 is also a continuation-in-part of U.S. application Ser. No. 12/924,802 filed Oct. 5, 2010, now U.S. Pat. No. 8,556,938, which claims the benefit of U.S. Provisional Application Nos. 61/278,240 filed Oct. 5, 2009; 61/336,911 filed Jan. 28, 2010; 61/343,737 filed May 3, 2010; 61/395,564 filed May 14, 2010; 61/395,752 filed May 17, 2010; 61/396,390 filed May 26, 2010; 61/398,807 filed Jul. 1, 2010; 61/400,504 filed Jul. 29, 2010; 61/402,959 filed Sep. 8, 2010; 61/403,696 filed Sep. 20, 2010; and 61/403,915 filed Sep. 23, 2010, each of which is incorporated by reference in its entirely herein, and for all purposes.

U.S. application Ser. No. 13/573,874 is also a continuation-in-part of U.S. application Ser. No. 12/802,849 filed Jun. 15, 2010, now abandoned, which claims the benefit of U.S. Provisional Application Nos. 61/268,708 filed Jun. 15, 2009; 61/270,754 filed Jul. 13, 2009; 61/336,911 filed Jan. 28, 2010; 61/395,564 filed May 14, 2010; 61/395,752 filed May 17, 2010; and 61/396,390 filed May 26, 2010, each of which is incorporated by reference in its entirely herein, and for all purposes.

BACKGROUND OF THE INVENTION

The present invention is directed to polyaxial bone screws for use in bone surgery, particularly spinal surgery and particularly to such screws with compression or pressure inserts and expansion lock split retainers to snap over, capture and retain the bone screw shank head in the receiver member assembly and later fix the bone screw shank with respect to the receiver assembly.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw. Generally, the screws must be inserted into the bone as an integral unit along with the head, or as a preassembled unit in the form of a shank and pivotal receiver, such as a polyaxial bone screw assembly.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include similar open ends for receiving rods or portions of other fixation and stabilization structure.

A common approach for providing vertebral column support is to implant bone screws into certain bones which then in turn support a longitudinal structure such as a rod, or are supported by such a rod. Bone screws of this type may have a fixed head or receiver relative to a shank thereof, or may be of a polyaxial screw nature. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred. Open-ended polyaxial bone screws typically allow for a loose or floppy rotation of the head or receiver about the shank until a desired rotational position of the receiver is achieved by fixing such position relative to the shank during a final stage of a medical procedure when a rod or other longitudinal connecting member is inserted into the receiver, followed by a locking screw or other closure. This floppy feature can be, in some cases, undesirable, but may not be that detrimental in others. Also, it is often desirable to insert the bone screw shank separate from the receiver or head due to its bulk which can get in the way of what the surgeon needs to do. Such screws that allow for this capability are sometimes referred to as modular polyaxial screws.

SUMMARY OF THE INVENTION

An embodiment of a polyaxial bone screw assembly according to the invention includes a shank having an integral upper portion or integral radiused or spherical head and a body for fixation to a bone; a separate receiver defining an upper open channel, a central bore, a lower cavity and a lower opening; a top drop and turn in place lower compression insert; a resilient, tiered, expansion locking split retainer for capturing the shank head in the receiver lower cavity and a locking insert having a lower compression friction fit collet, the shank head being frictionally engaged with, but still movable in a non-floppy manner, if desired, with respect to the friction fit insert prior to locking of the shank into a desired configuration. The shank is finally locked into a fixed position relative to the receiver by frictional engagement between the shank head and the insert and the shank head and one or more inner edges of the split ring-like retainer due to a downward force placed on the compression insert by a closure top pressing on a rod, or other longitudinal connecting member, captured within the receiver bore and channel. In the illustrated embodiments, retainers and compression inserts are downloaded into the receiver, but uploaded embodiments are also foreseen. The shank head can be positioned into the receiver lower cavity at the lower opening thereof prior to or after insertion of the shank into bone. The illustrated compression insert includes a lock and release feature for independent locking of the polyaxial mechanism so the screw can be used like a fixed monoaxial screw. Also, the shank and other components of the assembly can be cannulated for minimally invasive surgery applications.

The expansion-only retainer ring base portion in an embodiment of the present invention is positioned entirely below the shank head hemisphere in the receiver and can be a stronger, more substantial structure to resist larger pull out forces on the assembly. Outer tiers of the retainer allow for a very low profile within the receiver base. The retainer ring base can also be better supported on a stepped lower portion of the receiver having one or more horizontal loading surfaces located near the lower opening in the bottom of the receiver. This design has been found to be stronger and more secure when compared to that of the prior art which uses some type of contractile locking engagement between the parts. Also, once assembled it cannot be disassembled.

A pre-assembled receiver, compression insert and friction fit split retainer may be "pushed-on", "snapped-on" or "popped-on" to the shank head prior to or after implantation of the shank into a vertebra. Such a "snapping on" procedure includes the steps of uploading the shank head into the receiver lower opening, the shank head pressing against the base portion of the split retainer ring and expanding the resilient lower open retainer out into an expansion portion or chamber of the receiver cavity followed by an elastic return of the retainer back to a nominal or near nominal shape thereof after the hemisphere of the shank head or upper portion passes through the lower ring-like portion of the retainer. With the aid of tooling, the shank head enters into a friction fit engagement with a lower collet portion of the insert, the insert being pressed downwardly into a tapered portion of the receiver as well as against the shank head. In the illustrated embodiments, when the shank is ultimately locked between the compression insert and the lower portion of the retainer, at least one lower retainer edge surface locks against the shank head. The final fixation occurs as a result of a locking expansion-type of contact between the shank head and the lower edge portion of the split retainer and an expansion-type of non-tapered locking engagement between the lower portion of the retainer ring and the locking chamber in the lower portion of the receiver cavity. The retainer can expand more in the upper portion or expansion chamber of the receiver cavity to allow the shank head to pass through, but has restricted expansion to retain the shank head when the retainer lower ring portion is against the locking chamber surfaces in the lower portion of the receiver cavity and the shank head is forced down against the retainer ring during final locking. In some embodiments, when the polyaxial mechanism is locked, the pressure or compression insert is forced or wedged against a surface of the receiver resulting in an interference locking engagement, allowing for adjustment or removal of the rod or other connecting member without loss of a desired angular relationship between the shank and the receiver. This independent locking feature allows the polyaxial screw to function like a fixed monoaxial screw.

The lower pressure insert may also be configured to be independently locked by a tool or instrument, thereby allowing the pop-on polyaxial screw to be distracted, compressed and/or rotated along and around the rod to provide for improved spinal correction techniques. Such a tool engages the receiver from the sides and then engages outwardly extending winged arms of the insert to force or wedge the insert down into a locked position within the receiver. With the tool still in place and the correction maintained, the rod is then locked within the receiver channel by a closure top followed by removal of the tool. This process may involve multiple screws all being manipulated simultaneously with multiple tools to achieve the desired correction.

A pop-on uni-planar bone screw assembly according to an embodiment of the invention includes an open retainer and a shank head having cooperating structure to result in a shank that pivots only along a direction of the rod. The shank head includes opposed planar sides that cooperate with planar surfaces of the retainer, limiting pivot to a single plane.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 4 is an enlarged perspective view of the receiver of FIG. 1.

FIG. 5 is a top plan view of the receiver of FIG. 4.

FIG. 6 is a bottom plan view of the receiver of FIG. 4.

FIG. 7 is a front elevational view of the receiver of FIG. 4.

FIG. 10 is an enlarged perspective view of the retainer of FIG. 1.

FIG. 11 is a top plan view of the retainer of FIG. 10.

FIG. 12 is a bottom plan view of the retainer of FIG. 10.

FIG. 13 is a front elevational view of the retainer of FIG. 10.

FIG. 14 is an enlarged cross-sectional view taken along the line 14-14 of FIG. 11.

FIG. 21 is an enlarged front elevational view of the retainer and receiver of FIG. 1 with portions of the receiver broken away to show the detail thereof, the retainer being shown downloaded into the receiver (in phantom) to a tipped, partially inserted stage of assembly (also in phantom), to a compressed partially inserted stage (maximum state of compression) at a lower portion of the receiver cavity.

FIG. 22 is a front elevational view of the retainer and receiver with portions broken away, similar to what is shown in FIG. 21, showing the retainer positioned lower in the receiver cavity and further showing the insert in position for assembly with the receiver (in phantom) and the insert downloaded into the receiver to a location suitable for rotation within the receiver.

FIG. 23 is a perspective view of the retainer, receiver and insert, similar to what is shown in FIG. 22, further showing the insert being rotated within the receiver and the receiver being crimped against the insert to prohibit any further rotation of the insert with respect to the receiver.

FIG. 24 is a greatly reduced front elevational view of the assembly of FIG. 23 further shown with a torque tool.

FIG. 25 is an enlarged and partial front elevational view, similar to FIG. 24 with portions broken away to show the detail thereof and showing the torque tool threaded onto the receiver.

FIG. 26 is an enlarged and partial front elevational view with portions broken away, similar to FIG. 25 and further showing a first stage of assembly with the shank of FIG. 1, also shown in enlarged and partial front elevation, a hemisphere of the shank head and the vertebra portion are both shown in phantom.

FIG. 27 is a partial front elevational view with portions broken away, similar to FIG. 26, and further showing the shank in a stage of assembly with the receiver and retainer, the retainer being in a fully expanded state about a mid-portion of the shank head.

FIG. 28 is a partial front elevational view with portions broken away, similar to FIG. 27, the spherical shank upper portion or head shown fully captured by the retainer.

FIG. 29 is an enlarged and partial perspective view of the assembly as shown in FIG. 28, illustrating a marking on the insert (shown by a plurality of x's) that is above a marking on the receive (also shown by x's), indicating that the insert is not locked with respect to the receiver.

FIG. 30 is a perspective view of a counter torque tool for use with some assemblies of the invention.

FIG. 30a is an enlarged and partial perspective view of the tool of FIG. 30.

FIG. 31 is a perspective view of a torque handle for use with some assemblies of the invention.

FIG. 32 is a front elevational view of the tools of FIGS. 30 and 31 shown cooperating with the assembly of FIG. 28, shown in reduced front elevation.

FIG. 33 is an enlarged and partial front elevational view of the assembly and tools of FIG. 32 with portions broken away to show the detail thereof, showing the torque tool pressing the insert down into friction fit engagement with the shank head.

FIG. 34 is a further enlarged and partial front elevational view with portions broken away of the assembly and tools as shown in FIG. 33.

FIG. 35 is an enlarged and partial front elevational view, similar to FIG. 34, showing the torque tool being slightly backed up and off of the insert with the insert remaining in frictional fit with the shank head.

FIG. 41 is a front elevational view with portions broken away of the tool and bone screw assembly of FIG. 40.

FIG. 42 is an enlarged and partial front elevational view with portions broken away of the tool and bone screw assembly of FIG. 41.

FIG. 43 is an enlarged and partial perspective view of the assembly of FIG. 42 with tooling removed, showing the insert locked against the shank head and the receiver inner surface, the assembly polyaxial mechanism in a fully locked position.

FIG. 44 is an enlarged and partial front elevational view with portions broken away of the locked assembly of FIG. 44.

FIG. 45 is a reduced and partial front elevational view with portions broken away, similar to FIG. 44, showing the closure top driver (in phantom) and the counter torque tool mounted back on the assembly to loosen the closure top and the rod without loosening the polyaxial mechanism as the insert is locked against the receiver, allowing the assembly to function like a monoaxial screw and allow a surgeon to further manipulate the rod and the screws.

FIG. 46 is an enlarged and partial front elevational view with portions broken away similar to FIG. 36, showing the assembly prior to locking and thus the receiver being pivotable in a non-floppy manner with respect to the shank.

FIG. 53 is a reduced front elevational view of the assembly of FIG. 52 equipped with the tooling shown in FIG. 32 (torque driver, counter torque tool and handle) for pressing the insert into friction fit cooperation with the shank to maintain the desired angle of the shank with respect to the receiver during remaining steps of implantation.

FIG. 54 is an enlarged and partial front elevational view with portions broken away of the friction fit tightened bone screw assembly of FIG. 53 with the tools removed and a rod and closure top inserted into the receiver.

FIG. 55 is a reduced and partial front elevational view with portions broken away of the assembly of FIG. 54 equipped with the tools shown in FIG. 40 (closure top driving tool, handle and counter torque tool) for locking the insert against both the shank head and the receiver inner surface by driving down the closure top into a final fully mated position.

FIG. 60 is a perspective view of a set of four sleeves according to an embodiment of the invention for use with bone screw assembly embodiments of the invention.

FIG. 61 is a reduced and partial perspective view of one of the sleeves of FIG. 60 shown assembled with a bone screw assembly of FIG. 1, with the rod and closure top of FIG. 1 removed and replaced by a cord (not shown) and the sleeve and an alternative cord-gripping closure top.

FIG. 62 is an enlarged side elevational view of the assembly of FIG. 61 with portions broken away to show the detail thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

Figure 1:
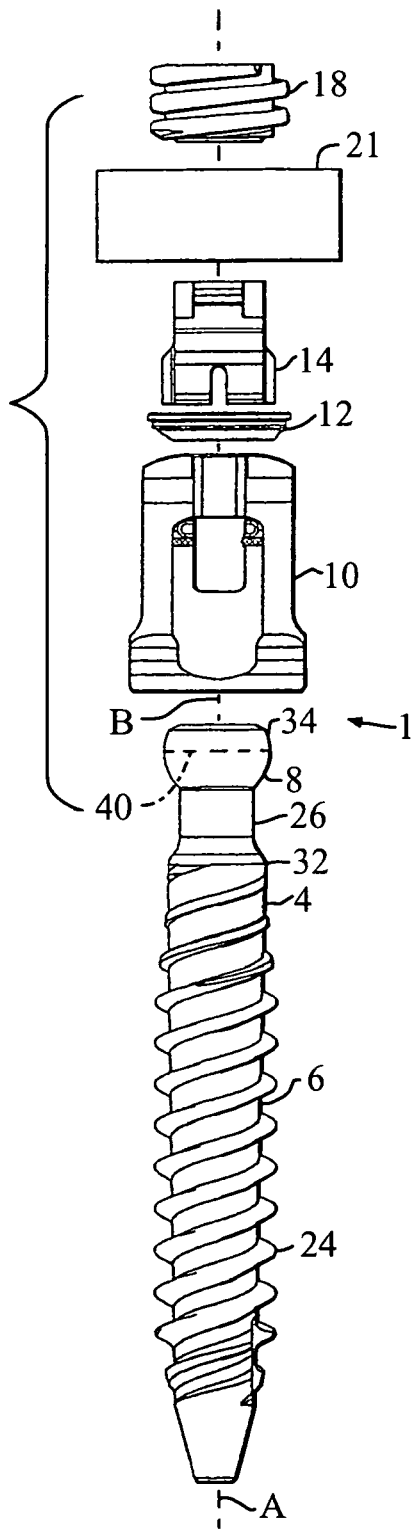
FIG. 1 is an exploded side elevational view of a polyaxial bone screw assembly according to an embodiment of the present invention including a shank, a receiver, an open, tiered, edge lock retainer and a top drop and turn in place lower compression insert having a compressive friction fit lower collet, and further shown with a portion of a longitudinal connecting member in the form of a rod and a closure top.
Figure 59:
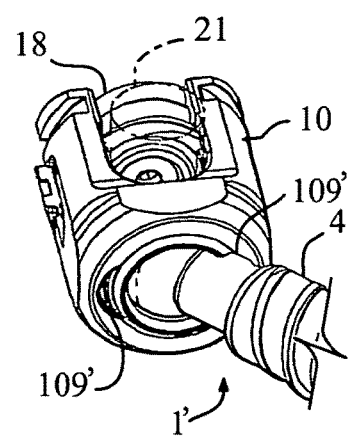
FIG. 59 is a reduced and partial perspective view of the receiver of FIG. 58 shown assembled with the shank, retainer, insert, rod and closure top of FIG. 1 and the shank being at a forty degree angle with respect to the alternative receiver.

With reference to FIGS. 1-59, the reference number 1 generally represents a polyaxial bone screw apparatus or assembly according to the present invention. The assembly 1 includes a shank 4, that further includes a body 6 integral with an upwardly extending upper portion or head 8; a receiver 10; an open dual edge lock retainer 12, and a crown-like compression or pressure insert 14 having a lower friction fit compression collet. The receiver 10, retainer 12 and compression insert 14 are initially assembled and may be further assembled with the shank 4 either prior or subsequent to implantation of the shank body 6 into a vertebra 17, as will be described in greater detail below. FIGS. 1 and 43-44 further show a closure structure 18 for capturing a longitudinal connecting member, for example, a rod 21 which in turn engages the compression insert 14 that presses against the shank head 8 into fixed frictional contact with the retainer 12, so as to capture, and fix the longitudinal connecting member 21 within the receiver 10 and thus fix the member 21 relative to a vertebra 17. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure. The illustrated rod 21 is hard, stiff, non-elastic and cylindrical, having an outer cylindrical surface 22. In some embodiments, the rod 21 may be elastic, deformable and/or of different materials and cross-sectional geometries. It is foreseen that in other embodiments (not shown) the closure top could deform the rod and press directly on the insert 14.

Figure 2:
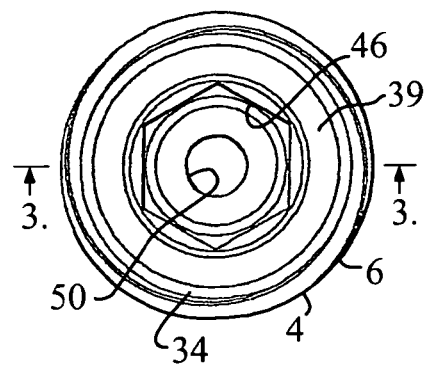
FIG. 2 is an enlarged top plan view of the shank of FIG. 1.
Figure 3:
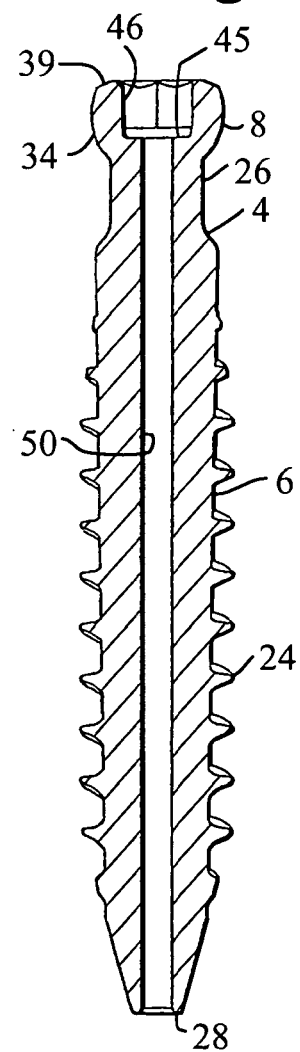
FIG. 3 is a reduced cross-sectional view taken along the line 3-3 of FIG. 2.
Figure 8:
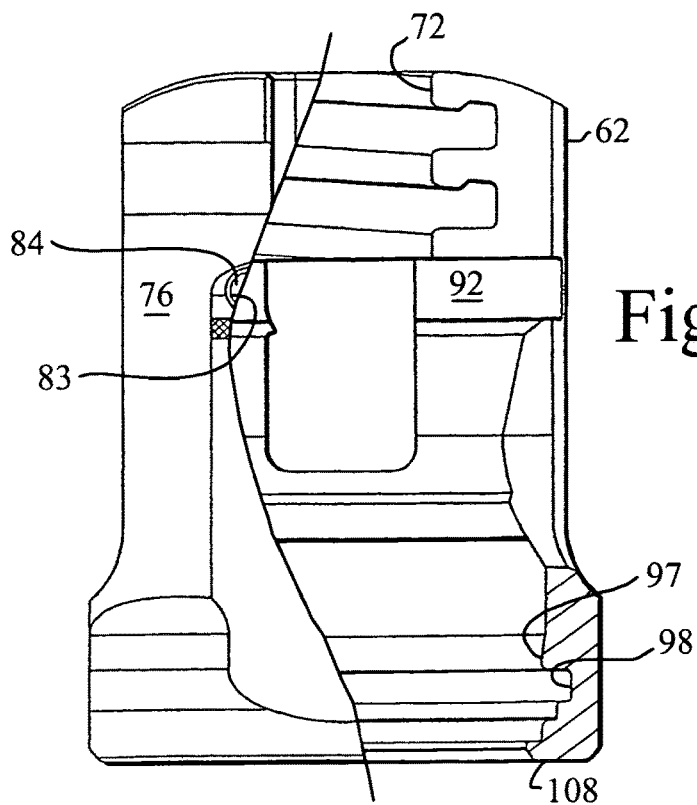
FIG. 8 is a side elevational view of the receiver of FIG. 4 with portions broken away to show the detail thereof.
Figure 9:
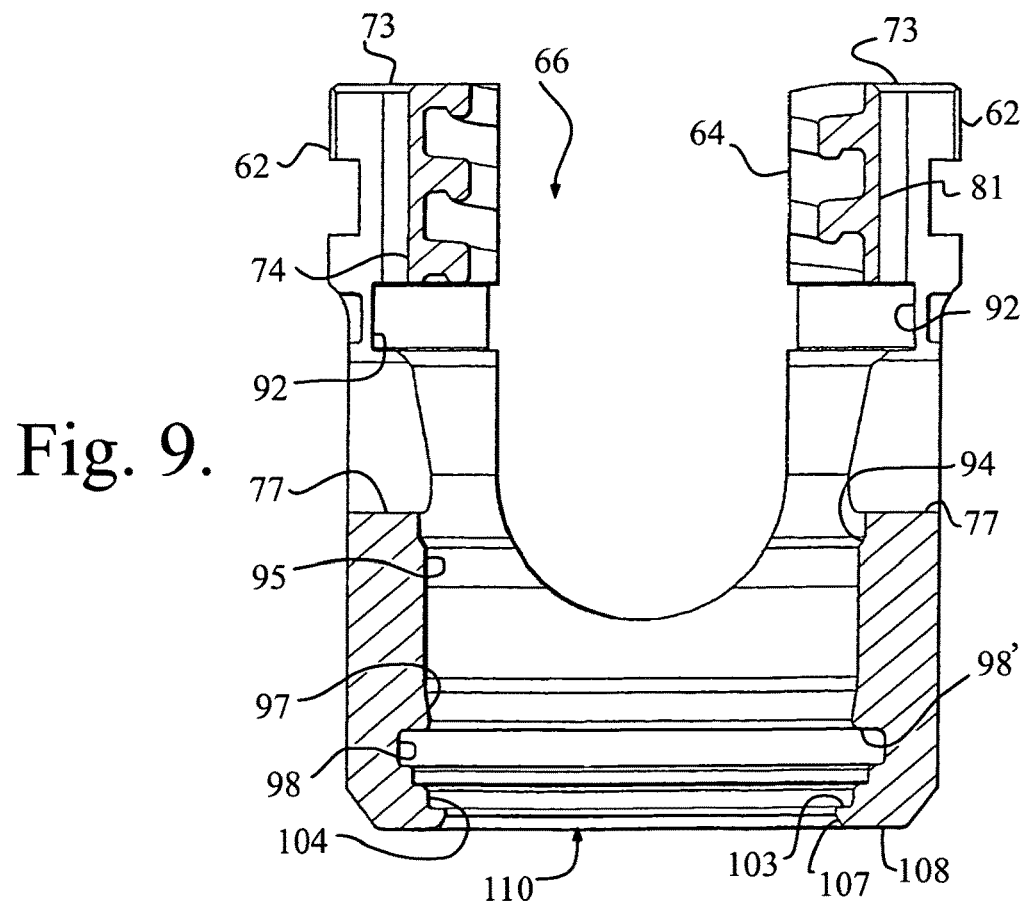
FIG. 9 is a cross-sectional view taken along the line 9-9 of FIG. 5.
Figure 15:
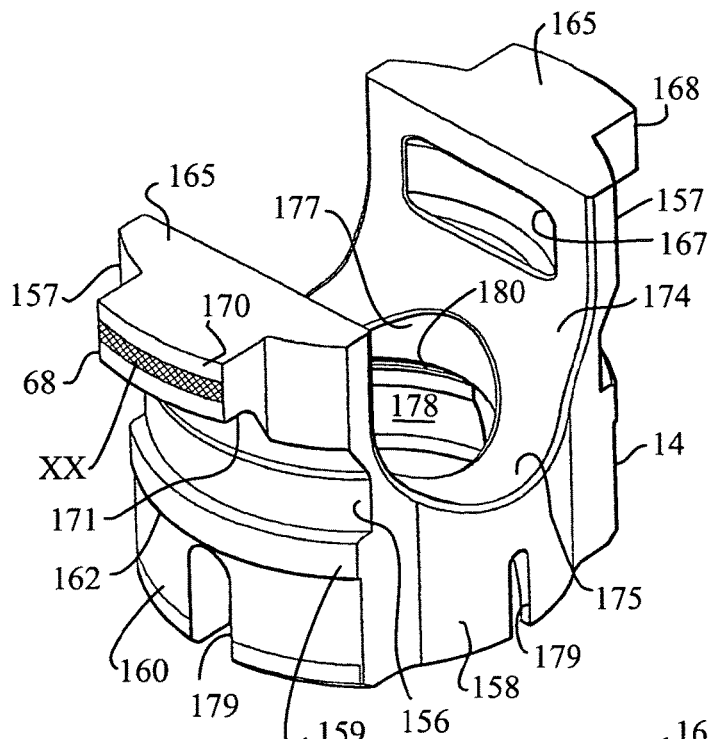
FIG. 15 is an enlarged perspective view of the insert of FIG. 1.
Figure 16:
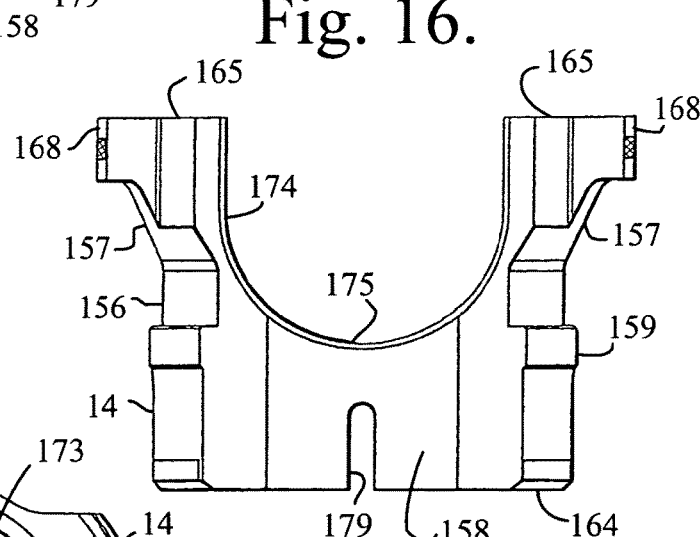
FIG. 16 is a front elevational view of the insert of FIG. 15.
Figure 17:
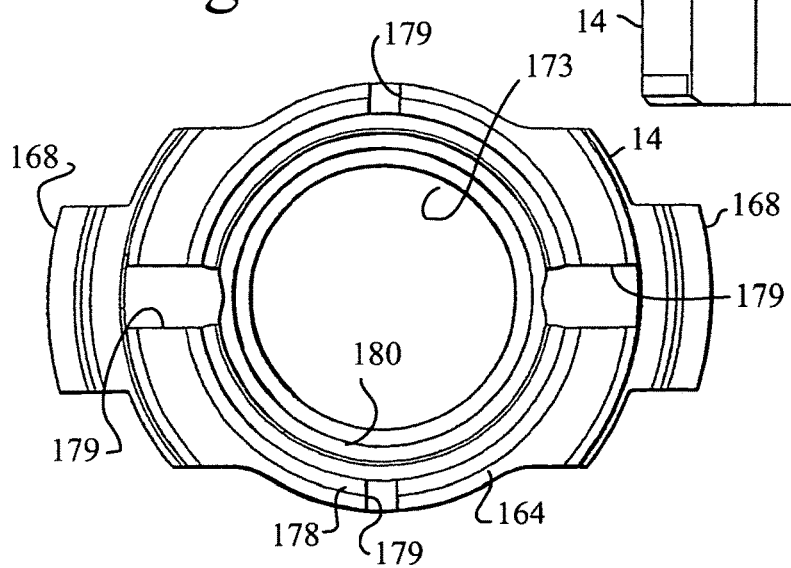
FIG. 17 is a bottom plan view of the insert of FIG. 15.
Figure 18:
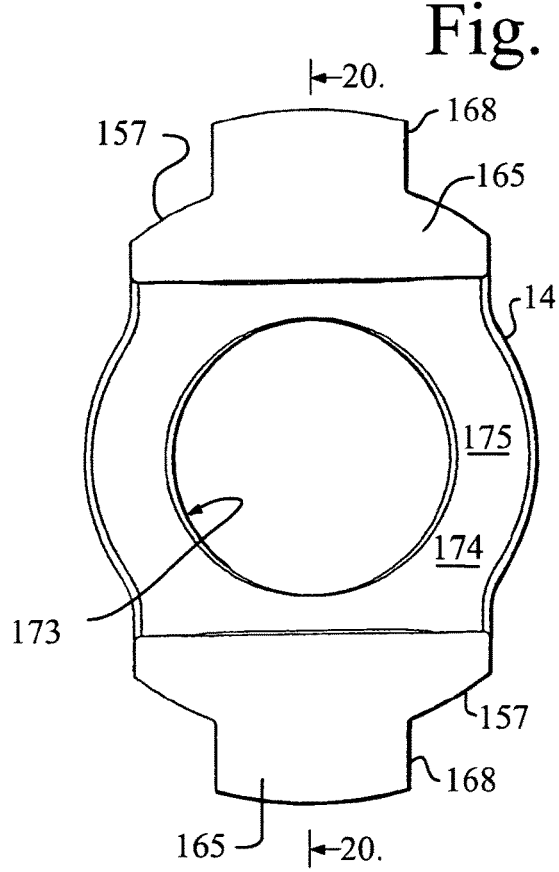
FIG. 18 is a top plan view of the insert of FIG. 15.
Figure 19:
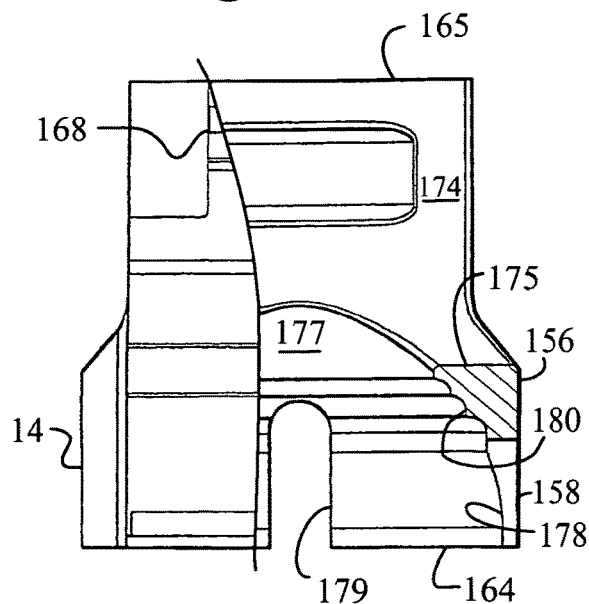
FIG. 19 is a side elevational view of the insert of FIG. 15 with portions broken away to show the detail thereof.

The shank 4, best illustrated in FIGS. 1-3, is elongate, with the shank body 6 having a helically wound bone implantable thread 24 (single or dual lead thread form and different thread types) extending from near a neck 26 located adjacent to the upper portion or head 8, to a tip 28 of the body 6 and extending radially outwardly therefrom. During use, the body 6 utilizing the thread 24 for gripping and advancement is implanted into the vertebra 17 leading with the tip 28 and driven down into the vertebra with an installation or driving tool (not shown), so as to be implanted in the vertebra to a location at or near the neck 26. The shank 4 has an elongate axis of rotation generally identified by the reference letter A.

The neck 26 extends axially upward from the shank body 6. The neck 26 may be of the same or is typically of a slightly reduced radius as compared to an adjacent upper end or top 32 of the body 6 where the thread 24 terminates. Further extending axially and outwardly from the neck 26 is the shank upper portion or head 8 that provides a connective or capture apparatus disposed at a distance from the upper end 32 and thus at a distance from the vertebra 17 when the body 6 is implanted in such vertebra.

The shank upper portion 8 is configured for a pivotable connection between the shank 4 and the retainer 12 and receiver 10 prior to fixing of the shank 4 in a desired position with respect to the receiver 10. The shank upper portion 8 has an outer, convex and substantially spherical surface 34 that extends outwardly and upwardly from the neck 26 to a top surface or rim 38. In the illustrated embodiment, a frusto-conical surface 39 is located between the spherical surface 34 and the rim 38 to provide for greater angulation of the shank with respect to the receiver, providing additional clearance during pivoting of the shank with respect to the receiver 10 and the insert 14. The spherical surface 34 has an outer radius configured for temporary frictional, non-floppy, sliding cooperation with a lower collet portion of the insert as well as ultimate frictional engagement with the retainer 12 at at least one lower inner edge thereof. In FIG. 1 and some of the other figures, a dotted line 40 designates a hemisphere of the spherical surface 34. The spherical surface 34 shown in the present embodiment is substantially smooth, but in some embodiments may include a roughening or other surface treatment and is sized and shaped for cooperation and ultimate frictional engagement with the compression insert 14 as well as ultimate frictional engagement with a lower ring-like edge of the retainer 12. The shank spherical surface 34 is locked into place exclusively by the insert 14 and the retainer 12 lower edge or edges and not by inner surfaces defining the receiver cavity.

A counter sunk and stepped or graduated annular seating surface or base 45 partially defines a portion of an internal drive feature or imprint 46. In some embodiments of the invention, the surface 45 is substantially planar. The illustrated internal drive feature 46 is an aperture formed in the top 38 and has a hex shape designed to receive a tool (not shown) of an Allen wrench type, into the aperture for rotating and driving the bone screw shank 4 into the vertebra 17. It is foreseen that such an internal tool engagement structure may take a variety of tool-engaging forms and may include one or more apertures of various shapes, such as a pair of spaced apart apertures or a multi-lobular or star-shaped aperture. The graduated seat or base surfaces 45 of the drive feature 46 are disposed substantially perpendicular to the axis A with the drive feature 46 otherwise being coaxial with the axis A. As illustrated in FIGS. 2 and 3, the drive seat 45 having beveled or stepped surfaces advantageously further enhances gripping with the driving tool. In operation, a driving tool is received in the internal drive feature 46, being seated at the base 45 and engaging the faces of the drive feature 46 for both driving and rotating the shank body 6 into the vertebra 17, either before or after the shank 4 is connected to the receiver 10 via the retainer 12, the driving tool extending into the receiver 10 when the shank 4, retainer 12 and receiver 10 combination is driven into the vertebra 17.

The shank 4 shown in the drawings is cannulated, having a small central bore 50 extending an entire length of the shank 4 along the axis A. The bore 50 is defined by an inner cylindrical wall of the shank 4 and has a circular opening at the shank tip 28 and an upper circular opening communicating with the external drive 46 at the driving seat 45. The bore 50 is coaxial with the threaded body 6 and the upper portion or head 8. The bore 50 provides a passage through the shank 4 interior for a length of wire (not shown) inserted into the vertebra 17 prior to the insertion of the shank body 6, the wire providing a guide for insertion of the shank body 6 into the vertebra 17. It is foreseen that the shank could be solid and made of different materials, including metal and non-metals.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 4-9, the receiver 10 has a generally U-shaped appearance with partially discontinuous cylindrical inner and outer profiles as well as planar and other curved surfaces. The receiver 10 has an axis of rotation B that is shown in FIG. 1 as being aligned with and the same as the axis of rotation A of the shank 4, such orientation being desirable, but not required during assembly of the receiver 10 with the shank 4. After the receiver 10 is pivotally attached to the shank 4, either before or after the shank 4 is implanted in a vertebra 17, the axis B is typically disposed at an angle with respect to the axis A.

The receiver 10 includes a base 60 forming an inner cavity, generally 61. Two opposed arms 62 extend upwardly from the base 60 and form a U-shaped channel 64 having an opening 66. Other features of the receiver 10 include, but are not limited to inner receiver arms surfaces, generally 70 that include a guide and advancement structure 72 located near arm top surfaces 73. In the illustrated embodiment, the guide and advancement structure 72 is a partial helically wound interlocking flangeform configured to mate under rotation with a similar structure on the closure structure 18. However, it is foreseen that for certain embodiments of the invention, the guide and advancement structure 72 could alternatively be a square-shaped thread, a buttress thread, a reverse angle thread or other thread-like or non-thread-like helically wound discontinuous advancement structures, for operably guiding under rotation and advancing the closure structure 18 downward between the arms 62, as well as eventual torquing when the closure structure 18 abuts against the rod 21 or other longitudinal connecting member. It is foreseen that the arms 62 could have break-off extensions.

An opposed pair of vertically extending outer grooves, generally 74, running substantially parallel to the receiver axis B are centrally formed in outer curved convex surfaces 76 of the arms 62. Each groove 74 runs centrally from the respective arm top surface 73 and terminates at a a through aperture 77. Each aperture 77 extends through the respective arm to the respective inner arm surface 70 and is located spaced from the receiver base 60. The grooves 74 may be slightly dovetailed for easily receiving an elongate tool (not shown) that enters into the groove 74 at the arm top surface 73 and is kept in close sliding contact with a surface 81 by the orientation of the surfaces defining the groove.

At the through aperture 77, the groove 74 terminates and directly there below are a pair of facing generally c-shaped ears 83 that do not extend completely through the respective arm 62, but rather include a thin wall that provides a crimping portion or wall 84. The total of four crimping portions or walls 84 are sized and shaped for pressing or crimping some or all of the wall material into walls or grooves of the insert 14 to prohibit rotation and misalignment of the insert 14 with respect to the receiver 10 as will be described in greater detail below. In other embodiments of the invention, other surfaces at or near the grooves 74 may be inwardly crimped. The illustrated through aperture 77 located below each grooves 74 is substantially the same width as the groove 74 there-above, resulting in the aperture 77 having a substantially rectangular profile.

The receiver 10 is a one-piece or integral structure and is devoid of any spring tabs or collet-like structures. Preferably the insert and/or receiver are configured with structure for blocking rotation of the insert with respect to the receiver, such as the crimp walls 84, but allowing some up and down movement of the insert with respect to the receiver during the assembly and implant procedure.

Returning to the interior surface 70 of the receiver arms 62, located below the guide and advancement structure 72 is a discontinuous cylindrical surface 92 partially defining a run-out feature for the guide and advancement structure 72. The cylindrical surface 92 is sized and shaped to receive an upper winged portion of the insert 14. Therefore, the surface 92 has a diameter greater than a greater diameter of the guide and advancement structure 72. The receiver arms may further includes sloped, stepped or chamfered surfaces above and below the surface 92. Directly below the surface 92 at or near the crimping walls 84 is at least one lip 92' that extends inwardly towards the aperture 77 and functions as a slight stop for the insert 14. Adjacent the lip 92' is an indicator strip "X" that functions in cooperation with an indicator strip "XX" of the insert for allowing a user to know if the polyaxial bone screw is in a loose or floppy state, a movable, non-floppy friction fit state, or a locked up state. Moving downwardly into the receiver cavity 61, features include a ledge 94 adjacent to a discontinuous cylindrical surface 95 providing a locking, interference fit surface for the insert 14, a continuous tapered or frusto-conical surface 97 providing a friction fit surface for the collet portion of the insert, a retainer expansion chamber portion defined in greater part by a cylindrical surface 98 adjacent an annular expansion chamber ceiling surface 98', a lower stepped or tiered retainer seating surface, generally 104 having a bottom annular surface 103, a lower flared or tapered surface 107 opening to a bottom exterior surface 108 at a bottom opening, generally 110 of the receiver.

With particular reference to FIGS. 1 and 10-14, the lower open or split friction fit retainer 12, that operates to capture the shank upper portion 8 within the receiver 10 is shown. The retainer 12 has a central axis that is operationally the same as the axis B associated with the receiver 10 when the shank upper portion 8 and the retainer 12 are installed within the receiver 10. The retainer 12 is essentially an open ring having an outer stepped or tiered surface 120 followed by an outer tapered or frusto-conical surface 121, a bottom surface 122, and a top planar surface 126. The retainer ring 12 is made from a resilient material, such as a stainless steel or titanium alloy, so that the retainer 12 may be contracted during assembly with the receiver and expanded about the shank head 8. The retainer 12 has a central channel or hollow through bore, generally 141, that passes entirely through the retainer 12 from the top surfaces 126 to the bottom surface 122 of the retainer body. Surfaces that define the channel or bore 141 include a discontinuous inner lower frusto-conical surface 143 adjacent to the retainer body bottom surface 122, a discontinuous, substantially cylindrical surface 145 adjacent the frusto-conical surface 143 and a discontinuous annular step 146 located adjacent the cylindrical surface 145, the surface 146 being substantially parallel to the bottom surface 122. Shank gripping edges created by the retainer surfaces include a lower edge or edge surface 148 and an upper edge surface 148' located at the retainer top 126. It is foreseen that there may be more or less than two shank gripping edge surfaces. A slit, generally 149 runs through the retainer 14, creating an opening generally perpendicular to the top and bottom surfaces. In some embodiments, such a slit may run obtuse to the bottom surface 122. In the illustrated embodiment, the slit 149 runs substantially perpendicular to the surfaces 122. The slit 149 is primarily for expansion of the retainer 12 during pop-on or snap-on assembly with the shank head 8. However, the slit 149 also compresses during assembly with the receiver 10 as will be described in greater detail below. At the location of the slit 149, a curved concave, cut-out surface 150 is formed in the bottom surface 122, the frusto-conical surface 143 and the cylindrical surface 145, as well as into the stepped portion 146. The surface 150 is radiused or otherwise curved for engagement with the shank head 8 at the surface 34. In the illustrated embodiment, the cut-out surface 150 is located substantially equally on either side of the slit 149 to provide for a desirable increased angle of orientation between the shank 8 and the retainer 12 and thus a desirable increased angle of articulation between the shank 8 and the receiver 10. The rotatability of the retainer 12 with respect to the receiver 10 allows for manipulation and placement of such an increased angle of articulation to a location desired by a surgeon. The through slit 149 of the resilient retainer 12 is defined by first and second end surfaces, 152 and 153 disposed in substantially parallel spaced relation to one another when the retainer is in a neutral or nominal state. Both end surfaces 152 and 153 are disposed perpendicular to the bottom surface 122, but in some embodiments may be disposed at an obtuse angle thereto. A width between the surfaces 152 and 153 is narrow to provide stability to the retainer 12 during operation, but wide enough to allow for some compression of the retainer during assembly as will be described in greater detail below. Because the retainer 12 is top loadable in a substantially neutral state and ultimately expands during locking of the polyaxial mechanism, the width of the slit 149 may be much smaller than might be required for a bottom loaded compressible retainer ring. It has been found that once the retainer 12 is expanded about the shank head 8, the retainer 12 may return to a new nominal or neutral orientation in which a gap between the surfaces 152 and 153 is slightly greater than the gap shown in the nominal state of FIG. 11, for example.

With particular reference to FIGS. 1 and 15-20, the locking compression insert 14 with a lower friction fit compressive collet is illustrated that is sized and shaped to be received by and down-loaded into the receiver 10 at the upper opening 66. The compression insert 14 has an operational central axis that is the same as the central axis B of the receiver 10. In operation, the insert advantageously frictionally engages the bone screw shank upper portion 8 as well as engaging the receiver 10 in an interference fit engagement, locking the shank 4 in a desired angular position with respect to the receiver 10 that remains in such locked position even if, for example, a rod and closure top are later removed and the rod is replaced with another rod or other longitudinal connecting member or member component, such as one of the sleeves shown in FIGS. 60-71. Such locked position may also be released by the surgeon if desired with insert engaging tools (not shown). The insert 14 actually includes two outer locking surfaces, one for interference fit as described above and a second lower collet surface that engages the receiver frusto-conical surface 97 and the shank head 8 to provide an interim, non-floppy friction fit, if desired, during certain times as required by the surgeon. The insert 14 is preferably made from a solid resilient material, such as a stainless steel or titanium alloy, so that portions of the insert may be grasped, pinched or pressed, if necessary, and un-wedged from the receiver 10 with a release tool.

Features of the locking and friction fit insert 14 include a substantially upper body 156 integral with a pair of upstanding arms 157. A lower body or collet body 158 is also substantially cylindrical. Located beneath each upstanding arm 157 is a discontinuous, cylindrical, interference fit surface 159 that extends outwardly from an arm and lower collet body outer substantially cylindrical surface 160, a diameter of the surface 159 being larger than a diameter of the surface 160. A lower ledge surface 162 partially defines the interference fit surface.

The insert 14 further includes substantially planar arm top surfaces 165 located opposite the bottom surface 164. Adjacent the top surfaces 165 of the arms 157 are outwardly extending wings 168. The wings 168 are partially defined by outer partially cylindrical surfaces 170 and by lower surfaces 171, the upper surfaces 169 and the lower surfaces 171 being substantially parallel to on another. Opposed side surfaces 172 span between top and bottom surfaces 169 and 171 respectively, of each wing 168, the side surfaces 172 being substantially perpendicular to adjacent top and bottom surfaces 169 and 171. The cylindrical surfaces 170 are sized and shaped for sliding rotation within the receiver arm cylindrical surfaces 92 during assembly of the insert 14 with the receiver 10.

Returning to the inner surfaces of the insert 14, a through bore, generally 173, is disposed primarily within and through the insert 14 and communicates with a generally U-shaped through channel formed by a saddle surface 174 that is substantially defined by the upstanding arms 157. Near the top surfaces 165, the saddle surface 174 is substantially planar, with apertures 167 extending thereinto. The saddle 174 has a lower seat 175 sized and shaped to closely, snugly engage the rod 21 or other longitudinal connecting member. It is foreseen that an alternative embodiment may be configured to include planar holding surfaces that closely hold a square or rectangular bar as well as hold a cylindrical rod-shaped, cord, or sleeved cord longitudinal connecting member The bore, generally 173, is further defined by an inner cylindrical surface 177 that communicates with the seat 175 and a lower concave, radiused inner collet surface 178 having a radius or surface for closely mating with the surface 34 of the shank upper portion 8. The inner collet surface 178 is discontinuous, being broken up by at least four spaced grooves 170 that run from the bottom surface 164 upwardly toward the insert upper body 158, terminating at or near a shank gripping surface portion, generally 180. The surface 178 terminates at the base surface 164. The gripping surface 180 is located between the cylindrical surface 177 and the lower radiused surface 178. The gripping surface portion 180 includes one or more stepped surfaces or ridges sized and shaped to grip and penetrate into the shank head 8 when the insert 14 is finally locked against the head surface 34. It is foreseen that the shank gripping surface portion 180 and also the surface 178 may additionally or alternatively include a roughened or textured surface or surface finish, or may be scored, knurled, or the like, for enhancing frictional engagement with the shank upper portion 8.

The compression insert 14 through bore 173 is sized and shaped to receive a driving tool therethrough that engages the shank drive feature 46 when the shank body 6 is driven into bone with the receiver 10 attached. Also, in some locking embodiments of the invention, the bore receives a manipulation tool used for releasing the insert from a locked position with the receiver, the tool pressing down on the shank and also gripping the insert at the apertures 167, or with other tool engaging features. Each of the arms 157 and the insert body 156 may include more surface features, such as cut-outs notches, bevels, etc. to provide adequate clearance for inserting the insert 14 into the receiver and cooperating with the retainer 12 during the different assembly steps.

The insert body has a diameter slightly smaller than a diameter between crests of the guide and advancement structure 72 of the receiver 10, allowing for top loading of the compression insert 14 into the receiver opening 66, with the arms 157 of the insert 14 being located between the receiver arms 62 during insertion of the insert 14 into the receiver 10. Once the arms 157 of the insert 14 are generally located beneath the guide and advancement structure 72, the insert 14 is rotated into place about the receiver axis B with the wings 168 entering the receiver groove formed by the cylindrical surface 92 until the wings are located in the apertures 77.

With reference to FIGS. 1 and 42-45, for example, the illustrated elongate rod or longitudinal connecting member 21 (of which only a portion has been shown) can be any of a variety of implants utilized in reconstructive spinal surgery, but is typically a cylindrical, elongate structure having an outer substantially smooth, cylindrical surface 22 of uniform diameter. The rod 21 may be made from a variety of metals, metal alloys, non-metals and deformable and less compressible plastics, including, but not limited to rods made of elastomeric, polyetheretherketone (PEEK) and other types of materials, such as polycarbonate urethanes (PCU) and polyethelenes.

Longitudinal connecting members for use with the assembly 1 may take a variety of shapes, including but not limited to rods or bars of oval, rectangular or other curved or polygonal cross-section. The shape of the insert 14 may be modified so as to closely hold the particular longitudinal connecting member used in the assembly 1. Some embodiments of the assembly 1 may also be used with a tensioned cord as will be described in greater detail with reference to FIGS. 60-71. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application. Thus, bars and rods may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 39-45, for example, the closure structure or closure top 18 shown with the assembly 1 is rotatably received between the spaced arms 62 of the receiver 10. It is noted that the closure 18 top could be a twist-in or slide-in closure structure. The illustrated closure structure 18 is substantially cylindrical and includes a an outer helically wound guide and advancement structure 182 in the form of a flange that operably joins with the guide and advancement structure 72 disposed on the arms 62 of the receiver 10. The flange form utilized in accordance with certain embodiments of the invention may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 18 downward between the arms 62 and having such a nature as to resist splaying of the arms 62 when the closure structure 18 is advanced into the channel 64, the flange form illustrated herein as described more fully in Applicant's U.S. Pat. No. 6,726,689 is preferred as the added strength provided by such flange form beneficially cooperates with and counters any reduction in strength caused by the any reduced profile of the receiver 10 that may more advantageously engage longitudinal connecting member components. The illustrated closure structure 18 also includes a top surface 184 with an internal drive 186 in the form of an aperture that is illustrated as a star-shape, such as that sold under the trademark TORX, or may be, for example, a hex drive or other internal drives such as slotted, tri-wing, spanner, two or more apertures of various shapes, and the like. A driving tool 260 (discussed below) sized and shaped for engagement with the internal drive 186 is used for both rotatable engagement and, if needed, disengagement of the closure 18 from the receiver arms 62. It is also foreseen that in some embodiments the closure structure 18 may alternatively include a break-off head designed to allow such a head to break from a base of the closure at a preselected torque, for example, 70 to 140 inch pounds. Such a closure structure would also include a base having an internal drive to be used for closure removal. A base or bottom surface 188 of the closure is planar and further includes an optional point (not shown) and a rim 190 for engagement and penetration into the surface 22 of the rod 21 in certain embodiments of the invention. It is noted that in some embodiments, the closure top bottom surface 188 does not include the point and/or the rim. The closure top 18 further includes a cannulation through bore 191 extending along a central axis thereof, opening at the drive feature 186 and extending through the bottom surfaces thereof. Such a through bore provides a passage through the closure 18 interior for a length of wire (not shown) inserted therein to provide a guide for insertion of the closure top into the receiver arms 62. Alternative closure tops may also be used with the bone anchors, such as screws for use with deformable rods that may include semi-spherical or domed bottom surfaces in lieu of the planar bottom and rim of the closure top 18.

The assembly 1 receiver 10, retainer 12 and compression insert 14 are typically assembled at a factory setting that includes tooling for holding and alignment of the component pieces and manipulating the retainer 12 and the insert 14 with respect to the receiver 10. In some circumstances, the shank 4 is also assembled with the receiver 10, the retainer 12 and the compression insert 14 at the factory. In other instances, it is desirable to first implant the shank 4, followed by addition of the pre-assembled receiver, retainer and compression insert at the insertion point. In this way, the surgeon may advantageously and more easily implant and manipulate the shanks 4, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 8 and/or hydroxyapatite on the shank 6), with the receiver, retainer and compression insert. Allowing the surgeon to choose the appropriately sized or treated shank 4 advantageously reduces inventory requirements, thus reducing overall cost and improving logistics and distribution.

Pre-assembly of the receiver 10, retainer 12 and compression insert 14 is shown in FIGS. 21-23. With particular reference to FIG. 21, first the retainer 12 is inserted into the upper receiver opening 66, leading with the outer tiered surface 120 with the top surface 126 facing one arm 62 and the retainer bottom surface 122 facing the opposing arm 62 (shown in phantom). The retainer 12 is then lowered in such sideways manner into the channel 64 and partially into the receiver cavity 61, followed by tilting the retainer 12 as also shown in phantom. Then, the retainer 12 is tilted into a position wherein the central axis of the retainer 12 is generally aligned with the receiver central axis B as shown in solid lines in FIG. 21, with the retainer being compressed at the slit 149 to clear the receiver inner surface 97. The retainer is then lowered further into the receiver as shown in FIG. 22, with the tiered surfaces 120 resting on the receiver stepped seating surfaces 104. At this time, the resilient retainer returns to a neutral state (possibly slightly more contracted than an original nominal state thereof, but such is not a concern as the retainer will be expanded about the shank head 8 in a later step). FIG. 23 nicely illustrates how the retainer 12 lower frusto-conical surface 121 sits below the receiver bottom surface 108, later providing a strong low-profile support for the shank head 8, allowing for desirable greater angulation between the shank 4 and the receiver 10 than if the retainer 12 were completely held above the receiver bottom surface 108. At this time, the retainer 12 is captured in the lower portion of the receiver 10 and cannot be moved upwardly past the receiver expansion chamber upper ceiling 98' unless a user forces the retainer into a compressed state again. The retainer 12 is free to rotate with respect to the receiver about the axis B.

With further reference to FIGS. 22 and 23, the compression insert 14 is then downloaded into the receiver 10 through the upper opening 66 with the bottom surface 164 facing the receiver arm top surfaces 73 and the insert arm wings 168 located between the opposed receiver arms 62. The insert 14 is then lowered toward the receiver base 60 until the insert 14 arm upper surfaces 165 are adjacent the run-out area below the guide and advancement structure 72 defined in part by the cylindrical surface 92. Thereafter, the insert 14 is rotated about the receiver axis B until the upper arm surfaces 165 are directly below the guide and advancement structure 72 with the wings 168 located in the apertures 77. In some embodiments, the insert arms may need to be compressed slightly during rotation to clear some of the inner surfaces 70 of the receiver arms 62. With particular reference to FIG. 23, after the insert 14 is rotated about the axis B to a desired aligned position with respect to the receiver, the four crimping walls 84 now located on either side of the insert wings 168 are pressed inwardly toward the insert, prohibiting further rotation of the insert about the axis B with respect to the receiver. It is noted that the insert wings are marked with a color strip or other indication illustrated by X's and identified by "xx" in the drawings. The receiver also has markings, identified in the drawings as "x". When the insert indicator "xx" is above the receiver indicator "x" as shown in FIG. 23, the user knows that the insert 14 is captured within the receiver 10 because of the wings being prohibited from upward movement by the guide and advancement structure 72, but that the insert 14 is otherwise has limited mobility along the axis B. As will be described more fully below, in later stages of assembly, these "xx" and "x" indicators will inform a user whether the insert 14 is in a relatively loose or floppy relationship with the shank 4, a friction fit relationship with the shank 4 wherein the shank is movable with respect to the receiver with some force, or a fully locked position in which the angle of the shank 4 with respect to the receiver 10 is fully locked in place and the bone anchor 1 may be manipulated like a monoaxial screw (but advantageously at an angle of inclination desired by the surgeon).

With further reference to FIG. 23, the retainer 12 and the insert 14 are now in a desired position for shipping as an assembly along with the separate shank 4. The insert 14 is also fully captured within the receiver 10 by the guide and advancement structure 72 prohibiting movement of the insert 14 up and out through the receiver opening 66 as well as by retainer 12 located below the insert. The receiver 10, retainer 12 and insert 14 combination is now pre-assembled and ready for assembly with the shank 4 either at the factory, by surgery staff prior to implantation, or directly upon an implanted shank 4 as will be described herein.

The bone screw shank 4 or an entire assembly 1 made up of the assembled shank 4, receiver 10, retainer 12 and compression insert 14, is screwed into a bone, such as the vertebra 17, by rotation of the shank 4 using a suitable driving tool that operably drives and rotates the shank body 6 by engagement thereof at the internal drive 46. Specifically, the vertebra 17 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw shank 4 or the entire assembly 1 is threaded onto the guide wire utilizing the cannulation bore 50 by first threading the wire into the opening at the bottom 28 and then out of the top opening at the drive feature 46. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires and attachable tower tools mating with the receiver. When the shank 4 is driven into the vertebra 17 without the remainder of the assembly 1, the shank 4 may either be driven to a desired final location or may be driven to a location slightly above or proud to provide for ease in assembly with the pre-assembled receiver, compression insert and retainer.

Figure 20:
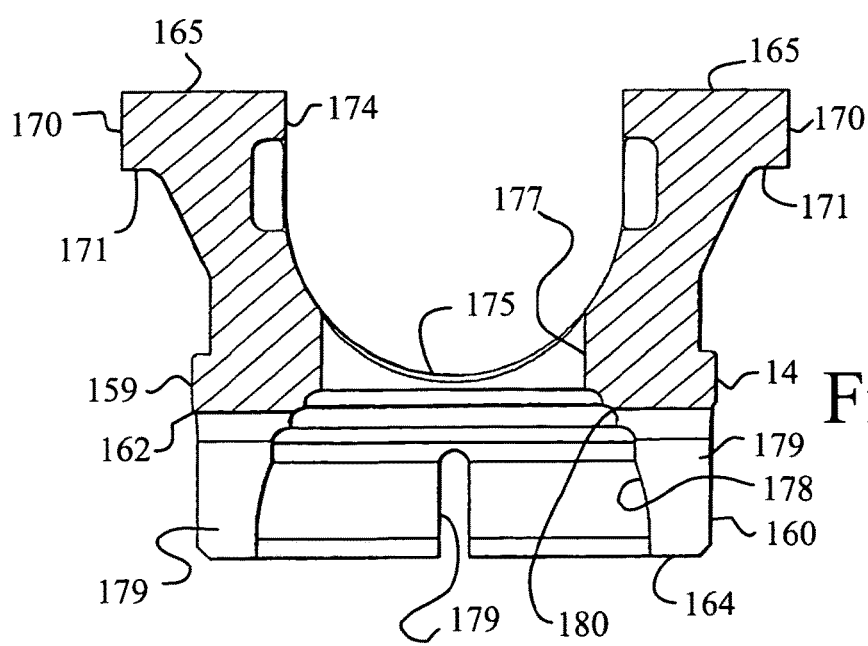
FIG. 20 is a cross-sectional view taken along the line 20-20 of FIG. 18.

With reference to FIGS. 24-47, when it is desired for the shank 4 to be "popped" on to the assembly shown in FIG. 23 by the surgical staff, the following procedure and tooling may be used: First, with respect to FIG. 24, a torque tube 210 is inserted by hand onto the receiver 10. The torque tube 210 includes a tubular body 211, a receiver mating guide and advancement structure 212 located adjacent a planar annular bottom surface 213, a handle mating surface 215 located near a planar annular top surface 214, and an annular groove 216 located beneath the mating surface 215. In the illustrated embodiment, the mating surface or drive 215 has a star-shape profile that not only mates with a handle 230 described below, but also good for finger tightening the torque tube 210 to the receiver 213 at the guide and advancement structure 72. After the torque tube guide and advancement structure 212 is mated to the receiver guide and advancement structure 72 by rotation of the torque tube 210 into the receiver arms, as shown in FIG. 25, the user then chooses a shank 4 and inserts the shank 4 head 8; into the receiver bottom opening 110 as shown in FIG. 26, all the while holding the torque tube 210 at the shaft 211. With reference to FIGS. 27 and 28, the shank is then "popped" into the receiver by pushing the shank head 8 through the retainer 12 through bore 141. FIG. 27 shows maximum expansion of the retainer 12 with upward movement of the retainer being blocked by the receiver surface 98'. FIG. 28 illustrated full capture of the shank head 8 by the retainer 12. With reference to FIG. 20, it is noted that the insert indicator strip "xx" is still located above the receiver indicator strip "x", letting the user know that the shank 4 is in an easily movable or floppy relationship with the receiver 10 at this time. It is foreseen that in an embodiment of the invention wherein the insert 14 is modified to remove the interference fit surface 159, a user could finger press such an insert down past the small lip 92' creating a mild friction fit between the insert 14 and the shank head 8, reducing some of the floppiness between the parts.

With reference to FIGS. 30-36, a member of the surgical staff may now place the insert 14 into a friction fit relationship with the shank head 8 at this time, to result in a non-floppy but movable relationship between the shank 4 and the receiver 10. To do this, the following tools may be used: the torque tube 210, a counter-torque tool 220 and a handle 230. It is noted that other tools may be used to place the insert 14 into an initial friction fit relationship and ultimate locking relationship with the shank head 8 and the receiver 10. For example, a dedicated jig for holding the shank 8 during "pop-on" and later tightening steps may be used. Furthermore, powered drive tools may be provided in lieu of the hand tightening tools illustrated and described herein.

The torque tube 210 has been described above. With reference to FIGS. 30 and 30a, the counter-torque tool 220 includes a tubular shaft 221 and a handle or holder arm 222 disposed perpendicular to the shaft 220. The tubular shaft 220 terminates at a bottom surface 223 and extending from the bottom surface 223 are a pair of opposed prongs 224 having bottom surfaces 225. The prongs each include curved inner surfaces 226 for sliding mating engagement with outer surfaces of the receiver arms 62. Inwardly facing projections or alignment stops 228 are located on each curved surface 226. The stops 228 are sized, shaped and positioned for being slidingly received into the grooves 74 of the receiver 10, but do not press against the insert 14. With reference to FIGS. 31, 32 and 33, the handle 230 includes a tubular shaft body 231 and an integral upper winged holding portion 232. Formed in a bottom surface 233 of the shank opposite the winged holder 232 is an internal drive aperture or through bore 234 that is also defined by a stop or ledge 235 that in turn is adjacent to an internal drive feature 236 having a star-shape profile that mates with the drive feature 215 of the torque tool 210. Adjacent a top surface 238 but still along the bore 234 is another drive feature 239 that is also star-shaped in profile, but smaller than the drive feature 236. The drive feature 239 is sized and shaped to cooperate with a shank driver 250.

Figure 36:
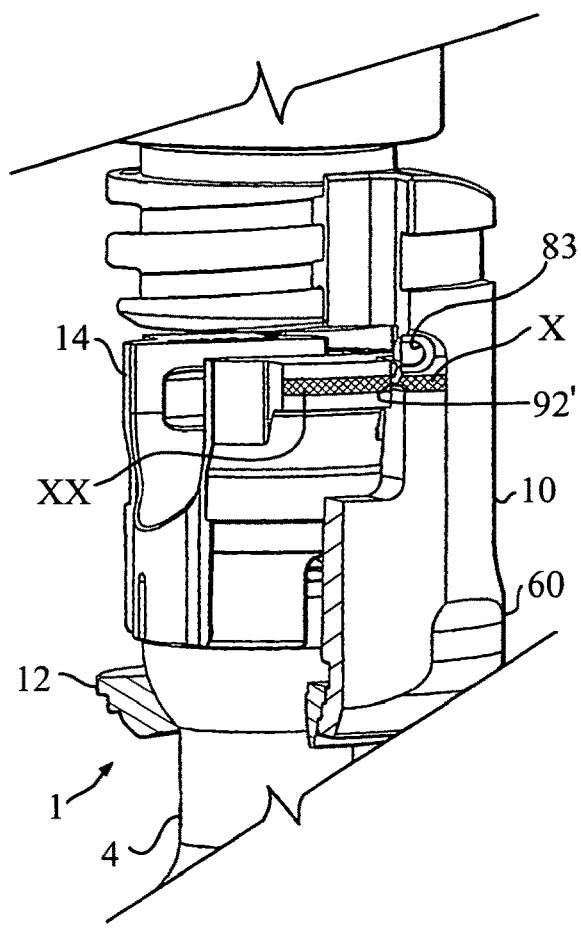
FIG. 36 is a partial perspective view of the assembly of FIG. 35 showing markings on the insert and the receiver in alignment indicating that the insert is in friction fit engagement with the shank, providing for non-floppy, but still movable pivoting of the shank with respect to the receiver.

As illustrated in FIGS. 32-35, the surgical staff mounts the counter torque tool 220 over the torque tube 210 with the projections 228 inserted into the grooves 74 until the surface 223 abuts against the receiver top surfaces 73, followed by mating the handle 230 to the torque tube 210, the star profile drive feature 236 sliding down over the torque tube outer feature 215 and the torque tube top surface 214 abutting against the inner ledge 237. Holding the counter torque handle 222, the user twists the torque handle 232, driving the torque tube bottom surface 213 down onto the insert 14 top surfaces 165 as best shown in FIG. 34. The torque tube can only go a limited distance, with the tube body 211 abutting the receiver top arm surfaces 73 when the insert is moved downwardly to a desired position to result in a friction fit, non floppy relationship between the insert 14 and the shank head 8. Specifically, downward movement of the insert 14 this desired amount creates a press fit between the insert outer surfaces 159 and the receiver inner cylindrical surfaces 95, locking the insert 14 against the receiver 10 at the surfaces 159 and 95. Such downward movement of the insert 14 also causes the frusto-conical surface 97 to press against the insert lower collet outer surface 160 located near the insert bottom surface 164, which in turn causes the insert collet inner surface 178 to frictionally engage the shank head spherical surface 34. With respect to FIG. 35, the user then reverses the drive and moves the torque tube 210 up slightly away from the insert 14. At this time, the insert will not move back up unless forced upwardly by tooling (not shown) that engages the insert wings 168 and forces the insert 14 out of the press fit with the receiver 10 at the surfaces 95 and 159. As illustrated in FIG. 36, when the tools are removed, a user knows that the insert 14 is locked to the receiver 10, but is in non-floppy, movable friction fit relationship with the shank as shown by the indicator strip "xx" being aligned with the receiver indicator strip "x". At this time, the retainer 12 is also still rotatable about the axis B of the receiver, allowing a user to position the slit 149 and concave surfaces 150 at a desired location for future shank articulation with respect to the receiver 10.

Figure 37:
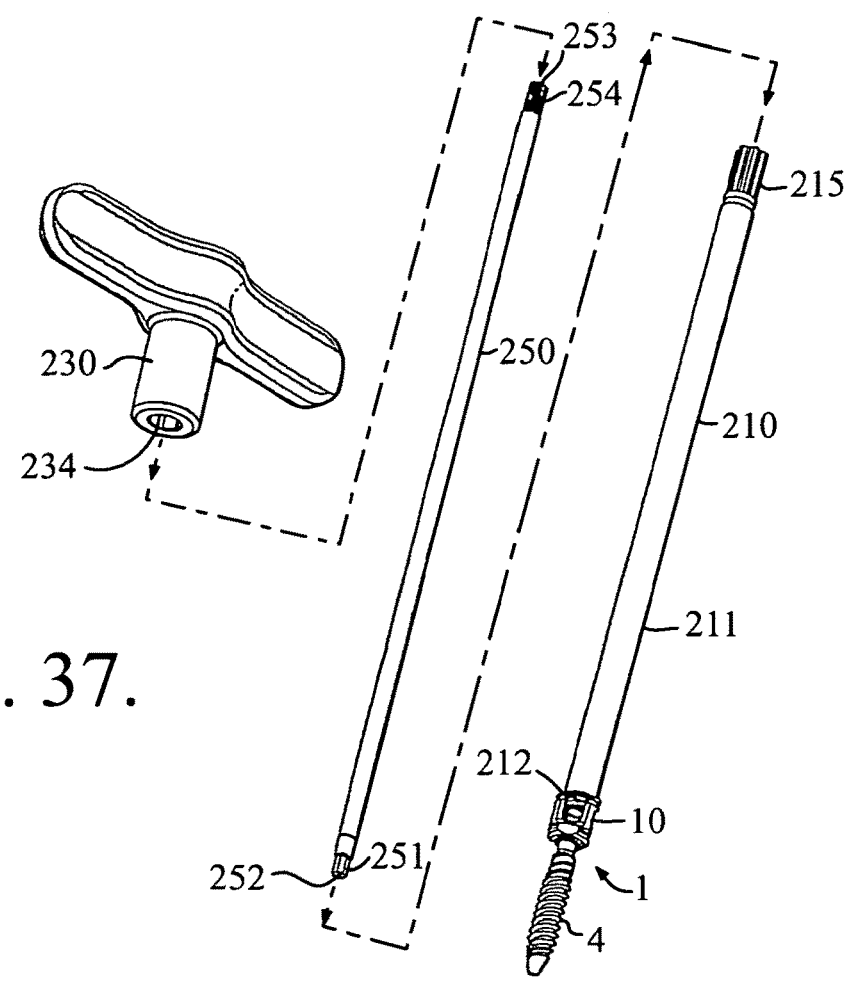
FIG. 37 is a reduced and exploded perspective view of a driver handle and bone screw driver for use with the torque tool and bone screw assembly of FIG. 36.
Figure 38:
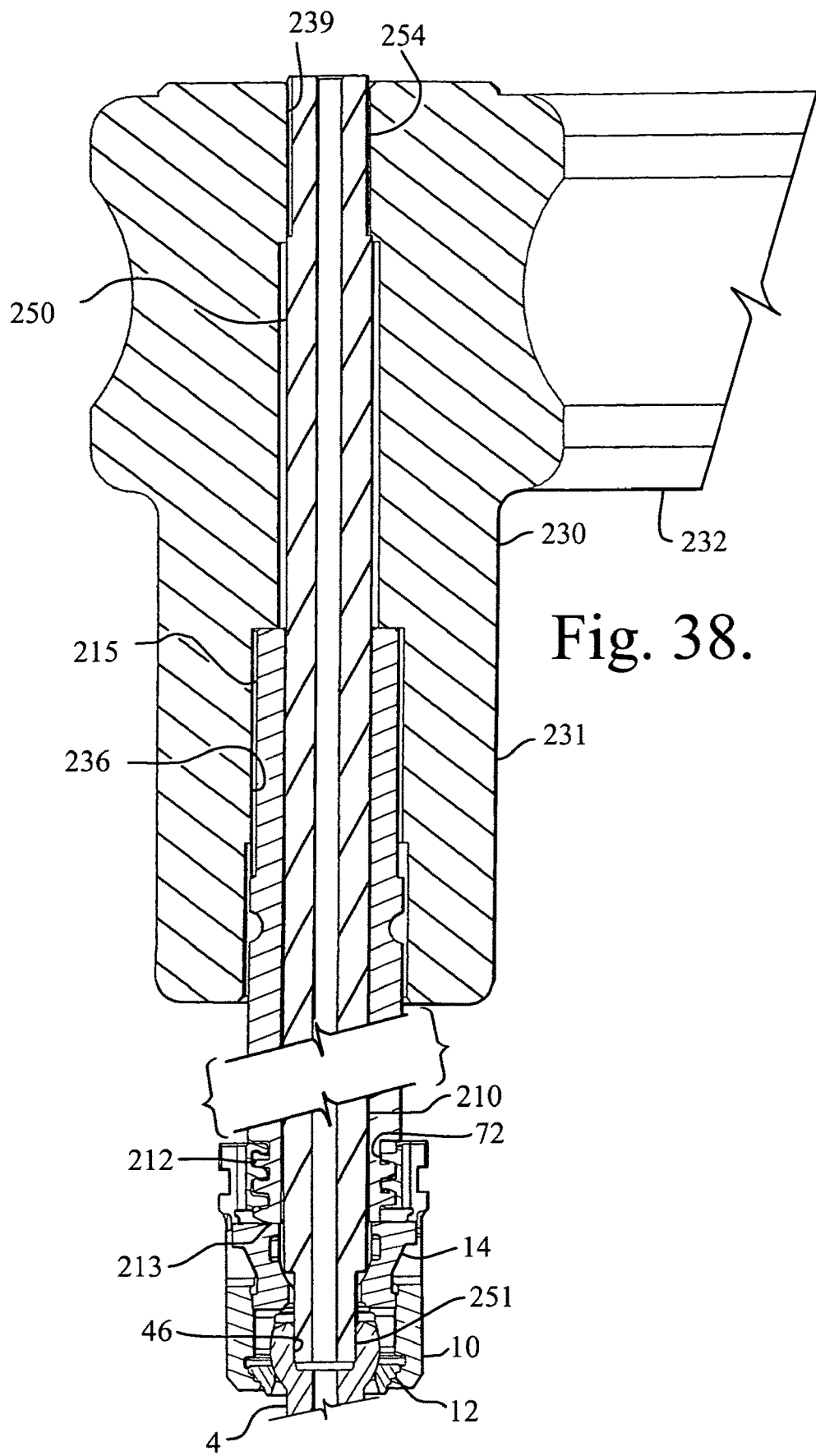
FIG. 38 is an enlarged and partial front elevational view of the tools and bone screw assembly of FIG. 37, shown assembled and ready for driving the shank into a vertebra.
Figure 39:
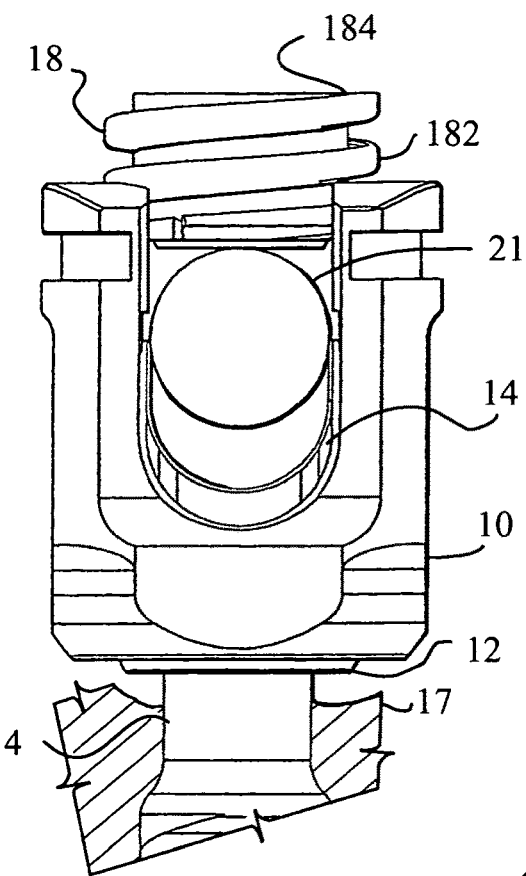
FIG. 39 is an enlarged and partial view of the bone screw assembly of FIG. 38 with bone screw driving and torque tools removed and also with the rod and closure top of FIG. 1, also shown in front elevation.

With reference to FIG. 37-38, the bone screw assembly 1 may now be driven into a vertebra 17. Now, the torque tube 210 is assembled with a driver 250 and the handle 230 as illustrated in FIG. 37. The driver 250 includes a drive feature 251 adjacent a bottom surface 252. The drive feature 251 is sized and shaped to mate with the drive feature 46 of the shank 4. Adjacent a top surface 253 is a star-shaped profile drive feature 254 sized and shaped to mate with the feature 239 of the handle 230. As shown in FIG. 38, the handle 230 mates with both the torque tube 210 and the driver 250 for driving the shank body 6 into a vertebra 17. Tooling is then removed and eventually a rod 21 and closure top 18 are inserted into the assembly 1 as shown in FIG. 39.

Figure 40:
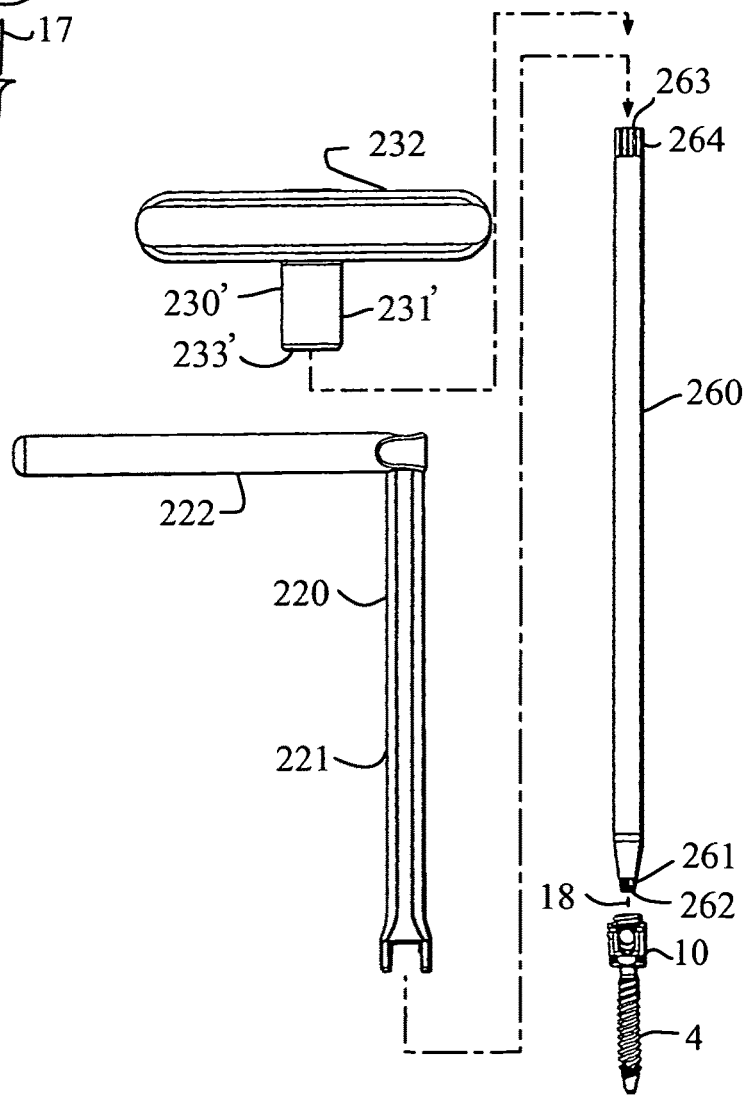
FIG. 40 is a reduced and exploded front elevational view of a closure top driver and handle and the counter torque tool of FIG. 30 and shown with the bone screw assembly of FIG. 39.

The closure top 18 is driven into the receiver guide and advancement structure 72 using a driver 260 having a drive feature 261 near a bottom surface 262 thereof and having a star-shaped profile drive 264 near a top surface 263. With reference to FIGS. 40 and 41, the counter-torque tool 220 is again mounted onto the receiver 10. This time, the closure top driver 260 is inserted into the counter-torque tube 221 and a drive handle 230' is mounted on the closure top driver 260. The drive handle 230' is substantially similar to the handle 230 previously described herein, having a drive feature 239' for mating with the closure top driver upper drive feature 264. With reference to FIGS. 42 and 43, as the closure top drive 260 is rotated, the closure top 18 guide and advancement structure 182 is fully mated with the receiver guide and advancement structure 72 causing downward movement of the closure top 18 onto the rod 21, the rod in turn pressing downwardly on the insert 14, pressing the insert deeper into the receiver 10, locking the insert 14 against the shank head 8 which is no longer pivotable with respect to the receiver 10. As shown in FIG. 43, a user knows that the entire polyaxial mechanism of the assembly 1 is fully locked because the indicator strip "xx" is now located below the receiver indicator strip "x".

FIG. 44 is another illustration of a fully locked up bone screw assembly 1 according to an embodiment of the invention. When the insert 14 compresses against the shank head 8, the head 8 presses against the retainer 12, pressing the retainer 12 outwardly against the receiver 10, with the tiered surfaces 120 pressing against and also fully seated downwardly against the receiver stepped surfaces 104. Edges 148 and 148' dig into the shank spherical surface 34. It is foreseen that the retainer 12 may be formed to create additional edge surfaces for frictionally engaging the shank head 8.

If the surgeon wishes to further manipulate the rod for distraction, compression, or other reasons, the closure top 18 may be loosened as shown in FIG. 45. However, at this time, the receiver cannot be tilted or otherwise angularly manipulated with respect to the shank 4. The assembly 1 advantageously performs like a strong, monoaxial screw, regardless of the orientation of the shank 4 with respect to the receiver 10.

Figure 47:
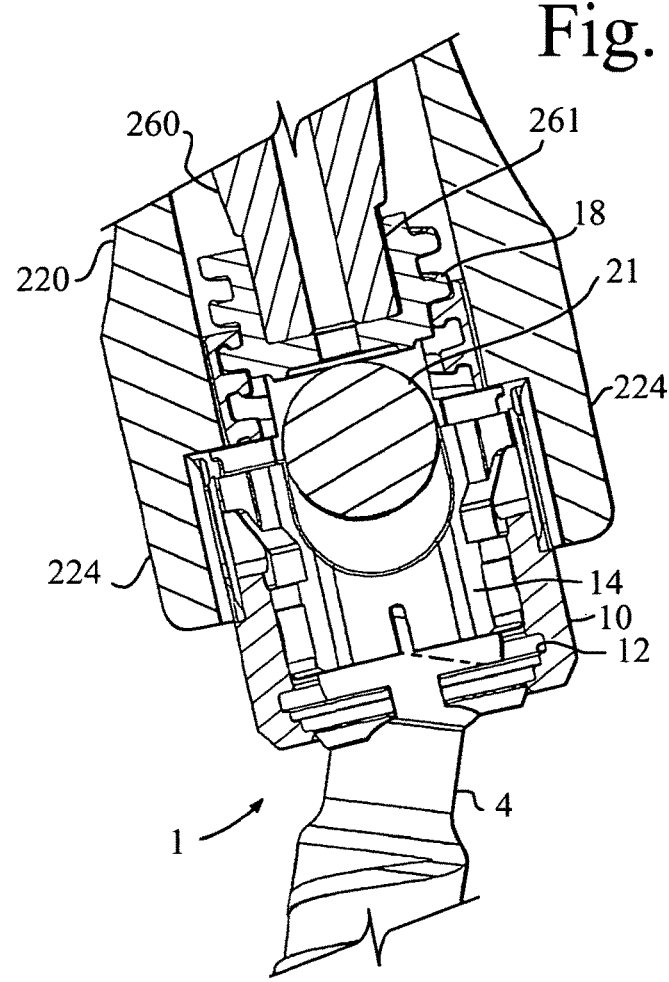
FIG. 47 is an enlarged and partial front elevational view with portions broken away, similar to FIG. 47, showing a rod and closure top being locked down by the driver and counter torque tool of FIG. 42, but with the receiver disposed at an angle with respect to the shank.

With reference to FIG. 46, the assembly 1 is illustrated in a friction, fit, but unlocked position in which the shank 4 is disposed at an angle with respect to the receiver 10. FIG. 47 illustrates using the same tooling as shown in FIGS. 40-42 to lock up the assembly of FIG. 46 in this desired angular orientation.

Figure 48:
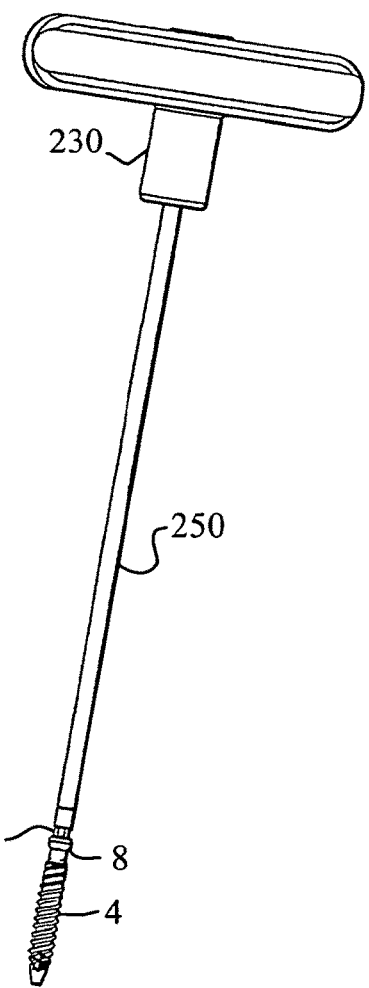
FIG. 48 is a reduced front elevational view of the shank of FIG. 1 shown with a shank driver and handle.
Figure 49:
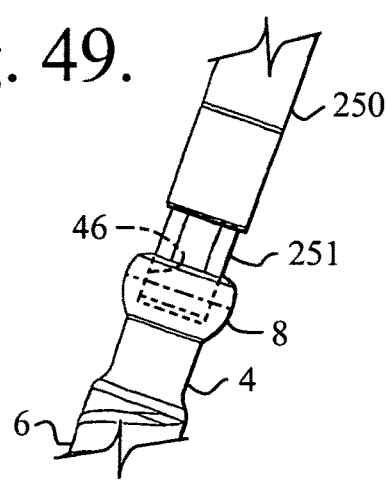
FIG. 49 is an enlarged and partial front elevational view of the shank and driver of FIG. 48.
Figure 50:
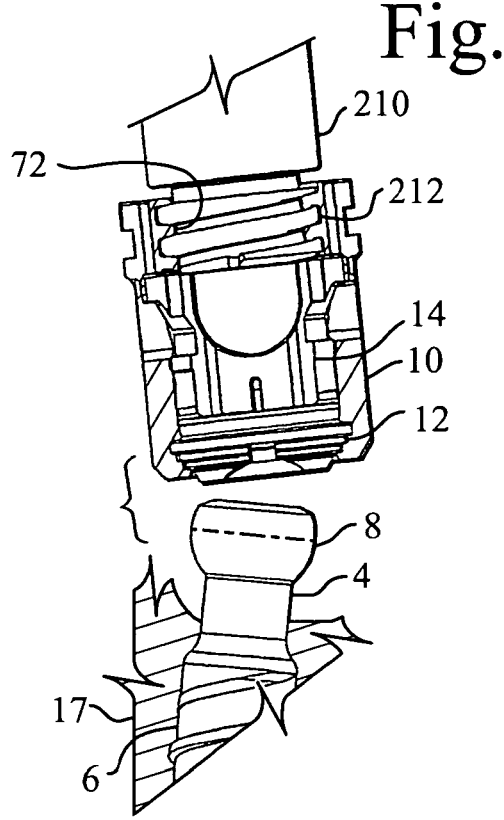
FIG. 50 is another partial front elevational view of the shank of FIG. 49 shown with the driver removed after driving the shank into a vertebra, and further showing the assembly and tooling of FIG. 25 in front elevation with portions broken away at an assembly stage of being placed into position above the implanted shank head.
Figure 51:
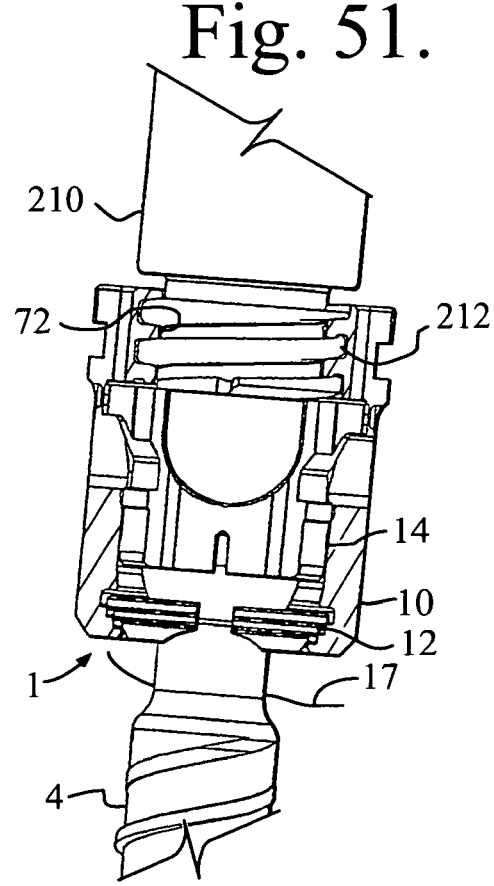
FIG. 51 is a partial front elevational view with portions broken away of the assembly of FIG. 50 showing the receiver popped into place over the shank.
Figure 52:
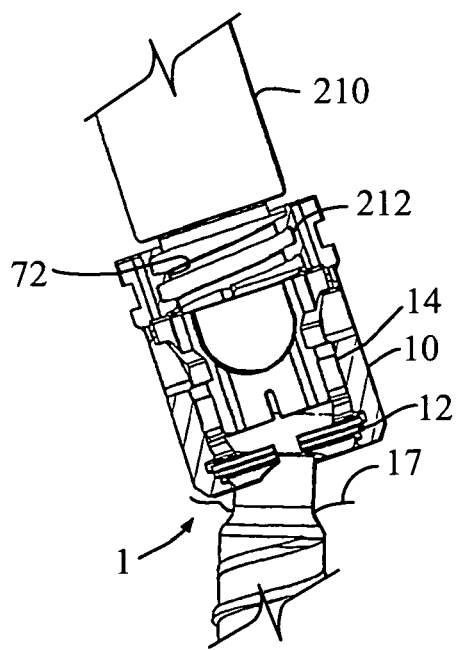
FIG. 52 is a partial front elevational view with portions broken away of the assembly of FIG. 51 showing the receiver being pivoted at an angle with respect to the implanted shank.
Figure 56:
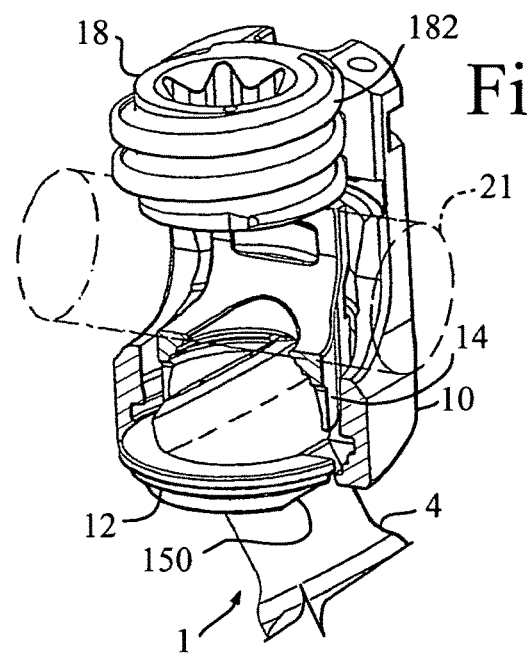
FIG. 56 is an enlarged and partial perspective view with portions broken away of the assembly of FIG. 55 with the tools removed after fixing the closure top and thus the rod and insert into place, locking the polyaxial mechanism, the shank shown at an eighteen degree angle (cephalad) with the rod shown in phantom.
Figure 57:
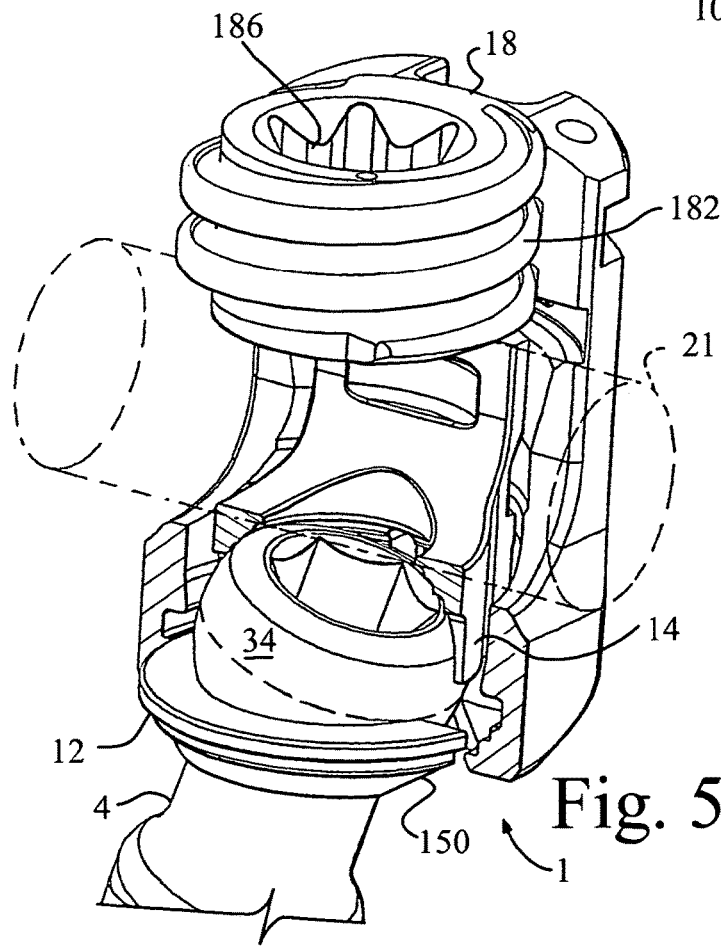
FIG. 57 is another enlarged and partial perspective view with portions broken away of the assembly of FIG. 55 with the tools removed, but wherein the degree of the angle between the shank and receiver was set to thirty degrees (caudad) prior to locking.

FIGS. 49-55 illustrated an "in vivo" method of driving a bone screw shank 4 into a vertebra 17, followed by "popping" on a receiver, retainer, insert assembly, followed by locking the resulting assembly 1 into a desired position with a rod 21 and closure top 18. Specifically, FIGS. 48 and 49 show using a driver 250 and cooperating handle 230 to drive the shank 6 into a vertebra 17. With respect to FIGS. 50 and 51, a receiver 10, retainer 12, insert 14 and torque tube 210 assembled as previously described herein with respect to FIGS. 21-36 are mounted on the already implanted shank head 8. With reference to FIGS. 52 and 53, the insert 14 may be placed into a non-floppy friction fit with the shank head 8 either before or after any desired articulation or pivoting of the shank 4 with respect to the receiver 10, the same tools: torque tube 210, counter-torque tube 220 and handle 230 being used as previously described herein. Then, a rod and closure top 18 may be inserted as shown in FIG. 54, followed by lock up using the driver 260 and other tools shown in FIG. 55. A resulting assembly shown in FIG. 56 shows an increased angle of articulation of about thirty degrees possible when the shank 4 is pivoted into the cut-out portion 150 of the retainer 12. FIG. 57 illustrates a shank to receiver angle of about eighteen degrees when the shank 4 is pivoted in a direction away from the cut-out 150.

Figure 58:
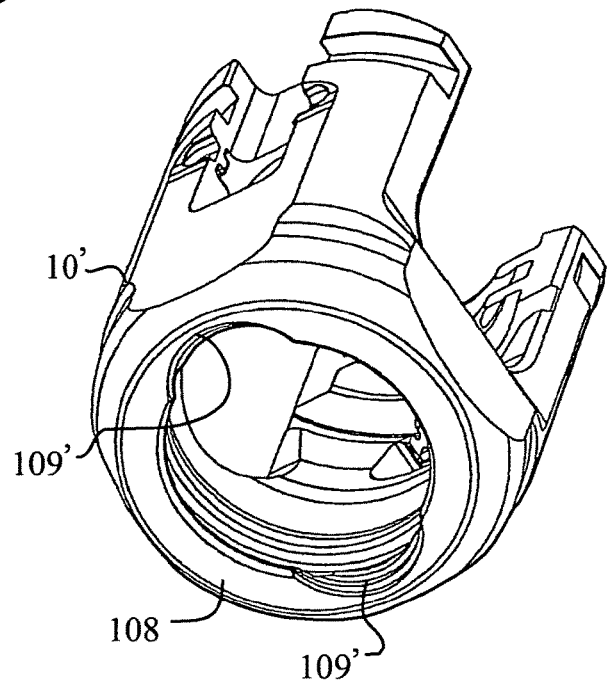
FIG. 58 is a perspective view of an alternative favored angle receiver according to an embodiment of the invention.

FIGS. 58 and 59 illustrate the use of an alternative favored angle receiver 10' with the other components of the assembly 1 shown in FIG. 1, resulting in a bone screw assembly 1'. The receiver 10' is identical to the receiver 10 with the exception that the receiver 10' further includes opposed cut-outs at the bottom surface 108, providing concave surfaces 109' for receiving some of the shank 4, resulting in angles of inclination between the shank 4 and receiver 10' of up to about forty degrees.

With reference to FIGS. 60-71, polyaxial bone screw assemblies 1 and 1' according to embodiments of the invention may be used with longitudinal connecting member assemblies that are sometimes called "soft" or "dynamic" connectors that may include one or more sleeves, generally 304, shown in FIG. 60, having varied lengths of tubular extensions on one or both sides thereof and further cooperating with an inner tensioned cord 306, one or more bumpers 314, one or more spacers 316, and in connectors that may include one or more end blockers 310 or fixers for fixing the cord to the connector assembly without fixing the cord directly to a bone anchor. A variety of such connector components are described in Applicants' U.S. patent application Ser. No. 12/802,849 filed Jun. 15, 2010 (U.S. Publication No. 2010/0331887) and incorporated by reference herein. With reference to FIG. 60, the four difference sleeves, generally 304 are shown, each sleeve differing only with respect to tubular extension lengths at one or both ends thereof. For example, a sleeve 304A includes one short tubular extension at one end thereof; a sleeve 304B includes opposed short tubular extensions; a sleeve 304C includes one longer tubular extension at one end thereof; and a sleeve 304D includes opposed longer tubular extensions at both ends thereof. The sleeve 304A is also illustrated in greater detail in FIGS. 66-70, for example. The sleeve 304B is shown assembled with the bone screw assembly 1 in FIGS. 61 and 62, for example. The cord 306, is shown, for example, in FIGS. 61 and 69 and in phantom in FIGS. 66 and 68, for example. The bumper 314 is shown, for example in FIGS. 66, 68 and 69. The spacer 316 is shown in FIGS. 63-66, 68, 69 and 71.

Specifically, the hard sleeve 304A is being described herein, noting that all of the sleeves 304 have the same or similar features and only differ with respect to the tubular extensions. The sleeve 304A includes a body portion 334 generally sized and shaped for being received within the polyaxial bone screw 1 receiver 10 and about a cord 306. A through bore 336 extends centrally through the body portion 334, the bore 336 being sized and shaped to slidingly receive the cord 306. At either side of the body portion 334 are a pair of opposed spaced partially radially extending flanges 338. The flanges 338 having upper and lower planar surfaces. The upper planar surfaces 339 may be in contact with a lip of the spacer 316 as will be described in more detail below. The body portion 334 further includes an annular planar top surface 340, a substantially cylindrical bottom surface, and opposed planar surfaces adjacent the bottom surface, as well as opposed partially cylindrical or otherwise protruding portions 344 located adjacent the planar surface 340 and extending centrally outwardly therefrom for cooperating and engaging both the bone screw insert 14 and a closure top, such as the closure top 18 shown in FIG. 67, for example, as will be described in more detail below. Thus, the top annular surface 340 partially defines each of the protruding portions 344. The body 334 is sized and shaped to closely fit within inner arm surfaces of the insert 14 and the bone screw receiver 10. The portions 344 function to center the sleeve 304 within the insert 14 and thus within the bone screw receiver 10 and also advantageously strengthen the sleeve, resulting in better load transfer. It is foreseen that in some embodiments, the flanges 338 may be reduced or eliminated as the centering of the sleeve with respect to the bone screw receiver 10 may be performed by the portion or portions 344.

Figure 69:
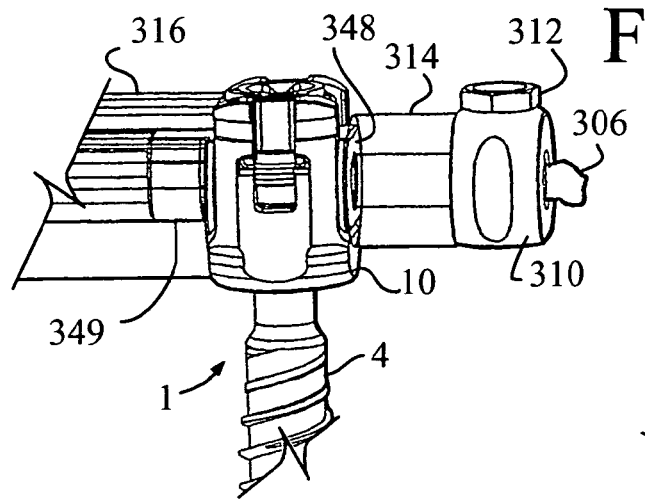
FIG. 69 is a reduced and partial front elevational view of the assembly of FIG. 68 shown with the set screw break off head removed.
Figure 70:
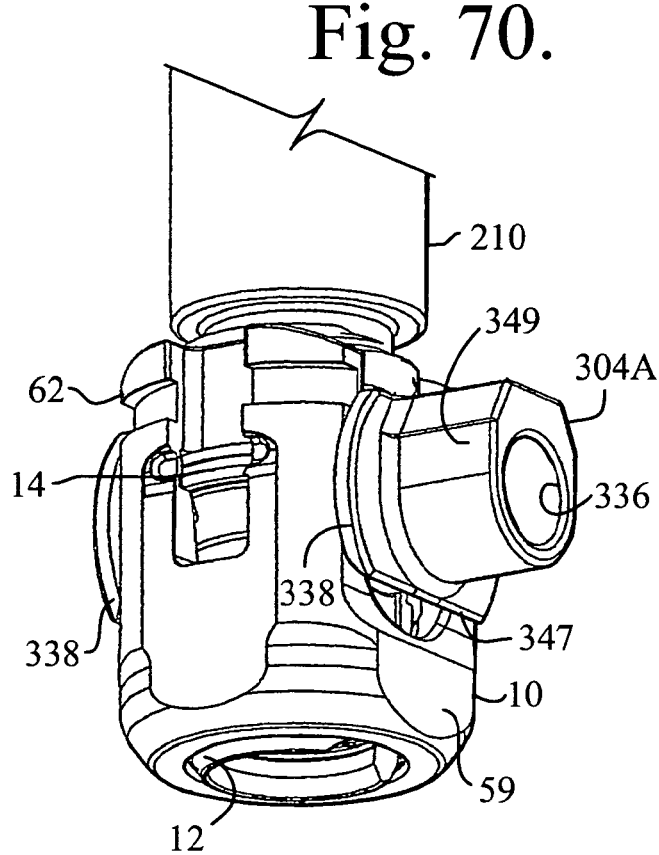
FIG. 70 is an enlarged and partial perspective view showing one of the sleeves of FIG. 60 assembled with a receiver, retainer and insert of FIG. 1 and further shown with a torque tool, the assembly ready to be popped onto a shank.

In the illustrated embodiment of FIGS. 60 and 70, each flange 338 has a pair of opposed cylindrical outer surface portions 346, the planar top surfaces 339 and planar bottom surfaces 347. The sleeve 304A further includes one outer planar annular surface 348 that is sized and shaped for directly abutting against a bumper or a spacer, as shown in FIG. 69, for example. The bore 336 extends through the planar surface 348. At an opposite end thereof, the sleeve 304A includes a tubular extension 349. Variously curved transition surfaces may be included that curve towards the flanges. The top planar surface 339 of one of the flanges also extends along the tubular extension 349 with the bore 336 extending all the way through the extension 349.

The body 334 substantially cylindrical lower surface is sized and shaped to be closely received by the insert saddle surface 174 when the insert is seated in the receiver 10. Near the top body surface 340 and also adjacent each of the flanges 338 are inwardly facing curved or radiused surfaces 356, sized and shaped to provide clearance for receiving the closure top 18 or an alternative closure top 18' shown in FIG. 62. It is noted that the body portion 334 as well as the inner surfaces of the flanges may be sized and shaped to be receivable by and frictionally fixed to a variety of monoaxial or polyaxial screw heads or receivers, including, but not limited to, the receiver 10.

Figure 68:
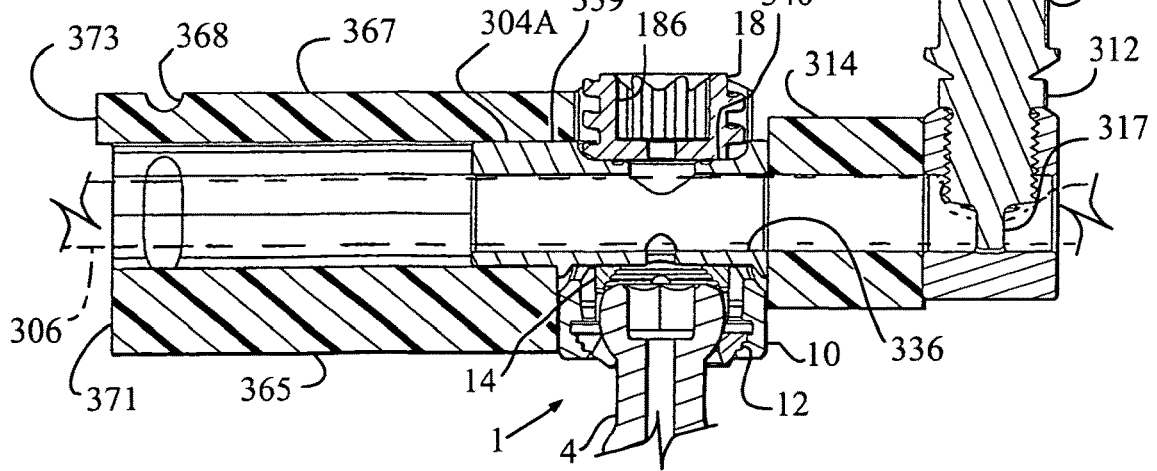
FIG. 68 is a reduced and partial side elevational view of the entire assembly of FIG. 66 with portions broken away to show the detail thereof.

With particular reference to FIGS. 60 and 68, a bore 360 is formed in the body 334 at the top surface 340 and located centrally between the flanges 338. The bore 360 is transverse to and communicates with the through bore 336. The bore 360 is sized and shaped to receive a cord penetrating extension 317 of the closure top 18' therein as best shown in FIG. 62. In FIG. 68, the sleeve 304 is shown with the closure top 18, for example, showing that the top 18 does not extend down into the through bore 360, allowing for the cord 306 to slide freely within the bore 336.

Figure 63:
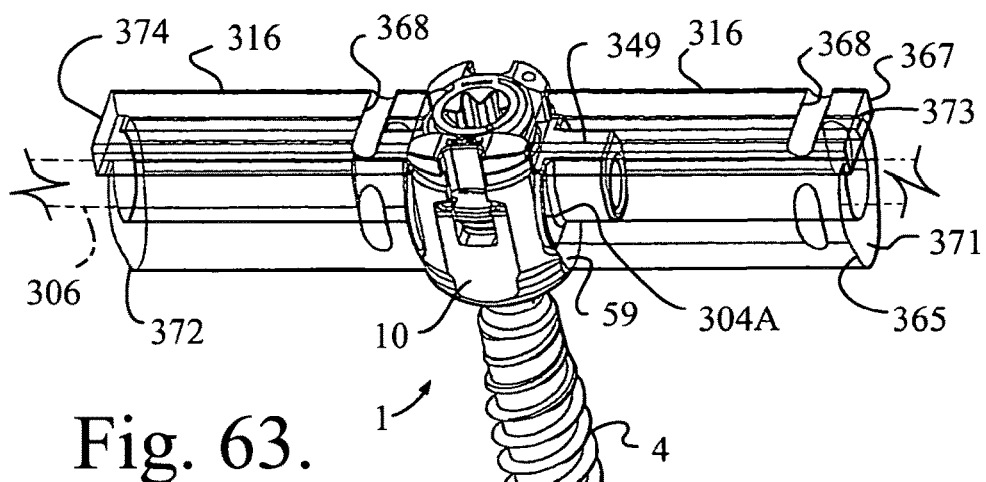
FIG. 63 is another perspective view of the sleeve of FIG. 61 shown assembled with the bone screw of FIG. 1 in a manner similar to that shown in FIG. 61, but with the "slipping" closure top of FIG. 1 in lieu of the cord gripping closure top of FIG. 61 and further shown with a cord (in phantom) and a pair of transparent compressible spacers located about the cord and at either side of the sleeve.
Figure 65:
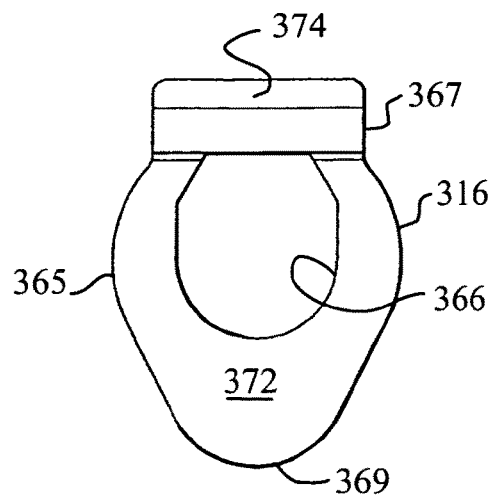
FIG. 65 is a front elevational view of the sleeve of FIG. 64.
Figure 66:
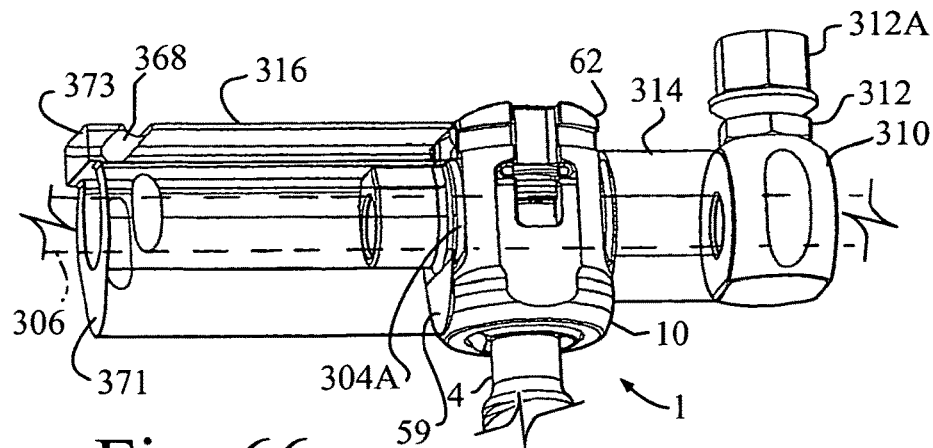
FIG. 66 is a partial perspective view of the bone screw assembly similar to that shown in FIG. 63, but with a different sleeve shown in FIG. 60, the cord shown in phantom, one of the spacers being replaced with a bumper (shown transparent) and blocker/set screw combination, the set screw having a break off head.

With reference to FIGS. 63-69, the sleeve 304A is shown assembled with the bone screw 1 and with the extension 349 being received in through a bore of the tubular spacer 316. FIG. 63 shows a spacer 316 located on either side of the bone screw 1, while FIGS. 66, 68 and 69 show the sleeve 304A cooperating with the sleeve 316 at one side thereof and a bumper 314 at an opposed side thereof. Both the sleeve and spacers surround a cord 306.

Figure 64:
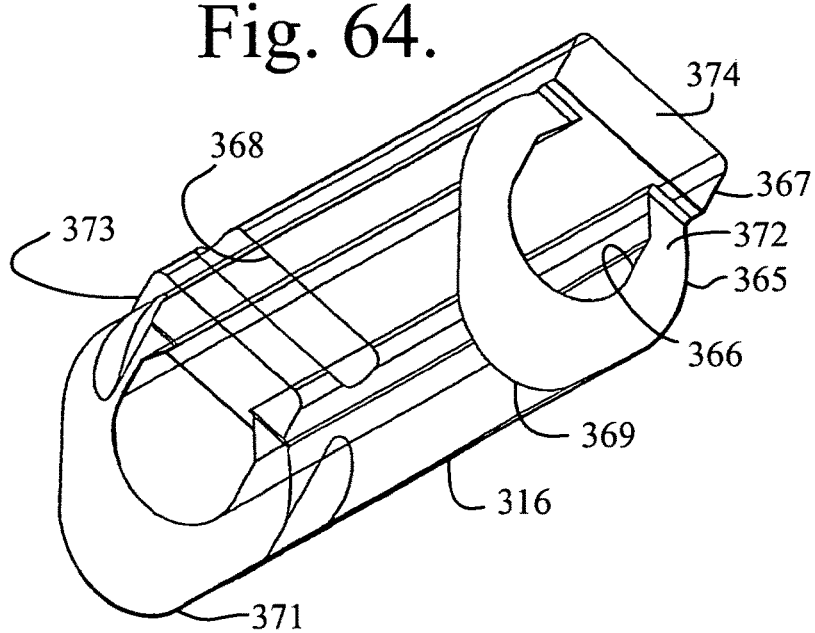
FIG. 64 is an enlarged perspective view of one of the sleeves of FIG. 63.

The spacer 316, also shown in FIGS. 64 and 65, includes a tubular body portion 365 that is somewhat ovoid in profile, having a through bore 366 located near an upper portion of the body 365, with a portion of the bore 366 being defined by an upper strip or box-like portion 367 defined by planar surfaces and having a top groove 368. The illustrated lower body 365 also includes one or more grooves. The upper polygonal portion 367 is sized and shaped to abut up against front or rear planar outer surfaces of the arms 62 of the receiver 10 located near top surfaces of the receiver 10, while the lower body portion 365 abuts against the receiver base 60 planar surface 59. The bore 366 is centrally located between curved sides of the body portion 365 that are adjacent the upper portion 367. A bottom curved surface 369, however, is spaced further from the bore 366 than are the side surfaces, resulting in a thicker spacer portion or wall near the bottom surface 369 than at the side surfaces located near the upper portion 367. The body portion 365 further includes opposed, planar, parallel front 371 and rear 372 outer surfaces. The top portion 367 also includes opposed planar, parallel front 373 and rear 374 outer surfaces that hang or project over the respective surfaces 371 and 372. In the illustrated embodiment, a jig is required to aid in cutting the spacer 316 to result in the overhanging feature of the top portion 367 that is illustrated on both ends of the spacer 316. For example, after measurements are made, a user would cut the spacer 316 to a desired length using such a jig to cut the surfaces 372 and 374 located opposite the groove 368, to result in the surface 374 extending out over the surface 372 as shown in the drawing figures.

Returning to FIG. 61, the bone screw 1 is illustrated assembled with the hard, inelastic, flanged sleeve 304B, sized and shaped for receiving the tensioned cord 306, the sleeve and the cord may be a part of such a longitudinal connector assembly or system as described in U.S. patent application Ser. No. 12/802,849. There is further illustrated at FIGS. 62-69 the cooperating end cord blocker or fixer 310 with the cord fixing set screw 312, shown with a break-off head 312A, the elastic end bumper 314 and spacers 316 that may be elastic or inelastic. As stated above, the spacers 316 may be cut to a desired length on the end opposite the groove 368. The cord blocker 310, the bumper 314 and spacer 316 are each located about the cord 306, typically with spacers 316 being disposed between each pair of bone anchors 1 of an overall assembly (not shown) that includes at least two bone anchors, such as the anchors 1, but may include any number of bone anchors with the cord 306 at least fixed at either end, either at a terminal or end bone anchor or at an end blocker 310 or other fixing member that may be, for example, a cord to hard rod coupler. The tubular bumper 314 and spacers 316 shown in the figures are transparent, allowing for viewing of the sleeves 304. However, it is foreseen that in other embodiments, the bumper and spacers may be made of materials that may not be transparent or translucent.

Figure 67:
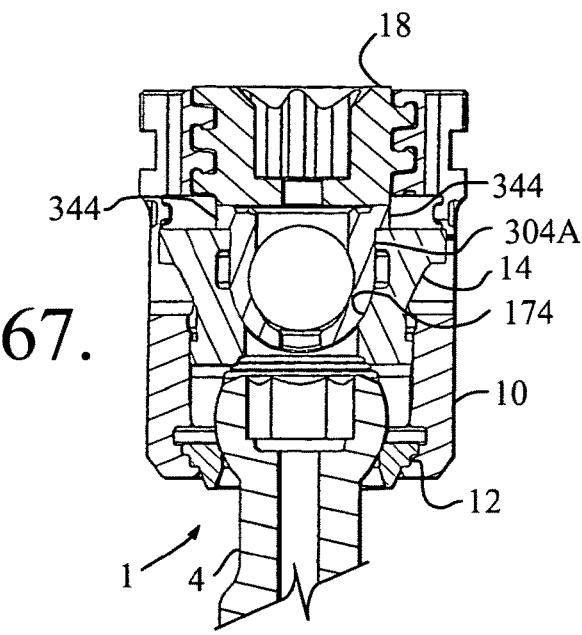
FIG. 67 is an enlarged and partial front elevational view of the bone screw assembly of FIG. 66 with portions broken away to show the detail thereof.

Also as shown in FIGS. 62 and 67, for example, at least two types of bone screw closures are utilized, either a slide or slipping closure top 18 previously described herein with respect to the assembly 1 or a cord gripping closure top 18'. The closure top 18 only differs from the top 18 in that the top 18' does not include a bottom rim or bottom point, but rather a cord fixing or penetrating extension 317 illustrated in FIG. 62 as having a bottom point or pin 318 for piercing into the cord 306. The slide or slip closure top 18 engages a respective sleeve 304 but not the cord 306, allowing the cord to slip or slide within the polyaxial screw 1. The grip closure top 18' extends through the sleeve 304 at the bore 360 and the portions 317, and in some embodiments 318, fix the cord 306 against an inner surface defining the bore 336 of the sleeve 304 and thus fixes the cord 306 in relation to the polyaxial screw 1 that is mated with the closure top 18'.

As shown in the drawings, the sleeve 304 (as well as the cord blocker 310) may include tubular extensions at one or either side thereof that may be sized and shaped to extend into the inner lumen or bore of the spacers 316 or the bumper 314. Such spacer overlap with respect to the sleeves is desired to provide additional anti-shear support for a connecting member. The illustrated sleeves also include cannulation bores 360A, useful for a variety of non-invasive surgical techniques. The bumper 314 also extends about the cord 306 and is typically made from an elastomer while the outer spacers 316, although typically elastomeric, may be made from a material with a different durometer, typically (but not always) being tougher and less compressible than the material of the bumper 314. The sleeves 304 and in some embodiments the spacers 316 are typically made from a hard, non-elastic material, such as a metal or metal alloy, like cobalt chromium. Flanged portions of the sleeves 304 are located on either side of the bone screw receivers 10, the flanges abutting directly against the spacers 316 or the bumper 314, the flanges extending radially outwardly to an extent to fully engage ends of adjacent spacers or the bumper, resulting in a stable, secure, substantially full contact between the individual elements of a connector assembly. Furthermore, in some embodiments, the flanges allow for assembly and dynamic setting of a longitudinal connector prior to implantation of the connector, if desired, with the cord 306 being placed in tension and at least the bumper 314 being placed in compression. In some embodiments of the invention, tensioning of the cord 316 and compression of the bumper 314 and optionally the spacers 316 may be performed after the longitudinal connector assembly sleeves 304 are attached to the bone screws 1.

The sleeves 304, as well as the cord blocker 310 with set screw 312 may be made from a variety of inelastic materials, including, but not limited to metals, metal alloys, including cobalt chromium, and inelastic plastics including, but not limited to plastic polymers such as polyetheretherketone (PEEK), ultra-high-molecular weight-polyethylene (UHMWP), polyurethanes and composites, including composites containing carbon fiber and layers of different materials.

Longitudinal connecting member embodiments of the invention may be assembled in a manner described in greater detail in U.S. patent application Ser. No. 12/802,849 incorporated by reference herein. It is noted that the cord 306 is typically much longer than shown in the drawing figures and then cut to length near an end thereof after being fully assembled with the remaining elements of the connector assembly, tensioned and fixed to the blocker 310. In some embodiments of the invention, single blockers, bumper/blocker combinations or rod/cord couplers (or various different combinations thereof) may be placed on either end of the assembly and the cord pre-tensioned before the assembly is implanted in and between the already implanted bone screws 1. In other embodiments, a loosely assembled connector may be placed in contact with and between the implanted bone screws 1, with the set screw 312 engaged with the cord 306 enough to prevent the elements from slipping off one end of the cord 306. However, in such an assembly, the cord 306 would not yet be tensioned and thus the individual elements would be spread apart along the cord and the cord would have to be of a length so that the cord could be grasped and tensioned after the assembly is fixed to the bone screws 1. A connector member assembly is then implanted by inserting each sleeve 304 into one of the bone screws 1. The sleeve 304 is top loaded through the receiver top opening with the flanges 338 located outside the receiver channel 64, the sleeve 304 being lowered until the body 334 is seated on the insert 14 with the sleeve protrusions 344 received by and engaging the insert arms.

Closure tops 18 or 18" are then inserted into and advanced between the arms of the bone screw receiver 10 so as to bias or push against the respective sleeves 304. A driving tool (not shown) is inserted into each closure drive to rotate and drive the respective closure top 18 or 18" into the respective receiver 10, the lower surface of the closure top engaging and pressing downwardly upon the top body surface 340 of the sleeve 304. As shown in FIG. 67, when the closure top 18 is used, the bottom rim 190 digs into the top body surface 340 but the closure does not engage the cord 306 located within the sleeve bore 336. As shown in FIGS. 67 and 68, downward movement of the closure top 18 or 18" onto the sleeve 304 in turn presses the sleeve 304 into engagement with the insert 14 that in turn presses downwardly on the shank head 8, locking the head 8 between the insert 14 and the retainer 12, the retainer 12 pressing outwardly against the receiver 10. Because the insert 14 is a lock and release insert, the insert 14 is now wedged against the receiver at the surface 95 and the polyaxial mechanism of the bone screw assembly 1 is now locked, even if the closure top 18 or 18" is loosened and rotated away from the sleeve surface 340.

A tensioning tool (not shown) known in the art may then be used to pull upon and put tension on the cord 306. It is noted that if more than one gripping closure tops 18' are used at either end of a connector, one top would be locked initially and then the other or others would be locked after tensioning, or alternatively, more than one tensioning step is performed. Preferably a bumper 314 and end blocker 310 are used at at least one end, and the cord 306 is preferably tensioned until the bumper 314 compresses and then the set screw 312 is rotated and driven into the blocker 310 and up against the cord 306 using a driving tool (not shown) engaged with the illustrated set screw break-off head 312A that breaks off of the screw 312 when a desired force is reached. Other embodiments of the invention may include screws 312 that do not have a break-off head. With reference to FIG. 66, the blocker 310 advantageously includes opposed grooves (or planar sides in some embodiments) allowing for the placement of a counter-torque tool for holding the blocker during tensioning and fixing of the cord 306 within the blocker. As explained in U.S. patent application Ser. No. 12/802,849, the set screw 312 and blocker 310 combination preferably includes a limited travel feature such that the set screw is locked into place at a location that firmly holds but does not damage the cord 306. The cord 306 is ultimately trimmed to a desired length close to each end of the connector.

The connector assembly is thus substantially dynamically loaded and oriented relative to the cooperating vertebra, providing relief (e.g., shock absorption) and protected movement with respect to flexion, extension, distraction and compressive forces placed on the assembly and the connected bone screws 1. In some embodiments of a connecting member according to the invention, a sleeve and rod combination may be used at one end (or both ends) of the assembly to provide a hard, non-elastic elongate portion for attachment to an additional bone screw or screws, if needed, to provide a connecting member with both dynamic, elastic segments as well as a longer rigid inelastic segment.

Eventually, if the spine requires more rigid support, such a connecting member assembly may be removed and replaced with another longitudinal connecting member, such as a solid rod or bar, having the same width or diameter as body portions of the sleeves 304, utilizing the same receivers 10 and the same or similar closure structures 18. Alternatively, if less support is eventually required, a less rigid, more flexible assembly, for example, an assembly having spacers 316 and a bumper or bumpers 314 made of a softer more compressible material than the spacer and bumper being replaced thereby, also utilizing the same bone screws 1 and the closures 18' as well as the closure 18.

Figure 71:
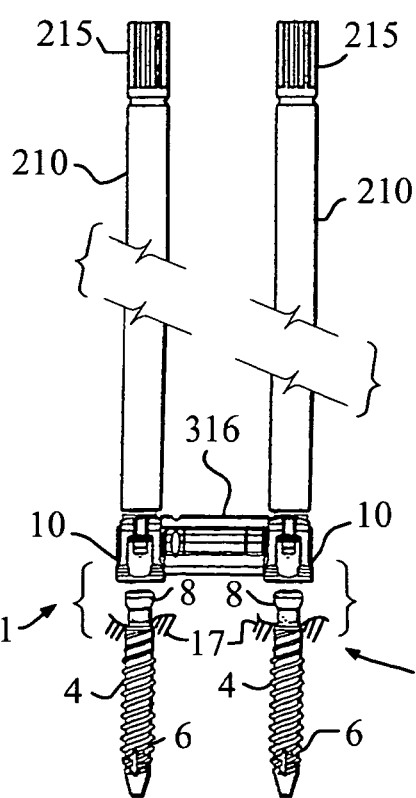
FIG. 71 is a reduced and partial front elevational view of two screw assemblies with sleeves of FIG. 60, a spacer and a pair of torque tubes, the dual assembly being shown just prior to popping onto two implanted bone screw shanks in an open manner.

FIG. 70 illustrates a portion of the bone screw assembly 1 of an embodiment of the invention prior to assembly with the shank 4 that further includes the sleeve 304A. The receiver 10 is attached to the torque tube 210 and thus the assembly portion is ready for "popping" onto a shank head 8, either before or after the shank is implanted into bone. FIG. 71 illustrates utilizing two bone screw assembly portions as shown in FIG. 70 equipped with sleeves 304A and having a cord 306 and spacer 316 already mounted therebetween prior to mounting on a pair of previously implanted shanks 4.

Figure 72:
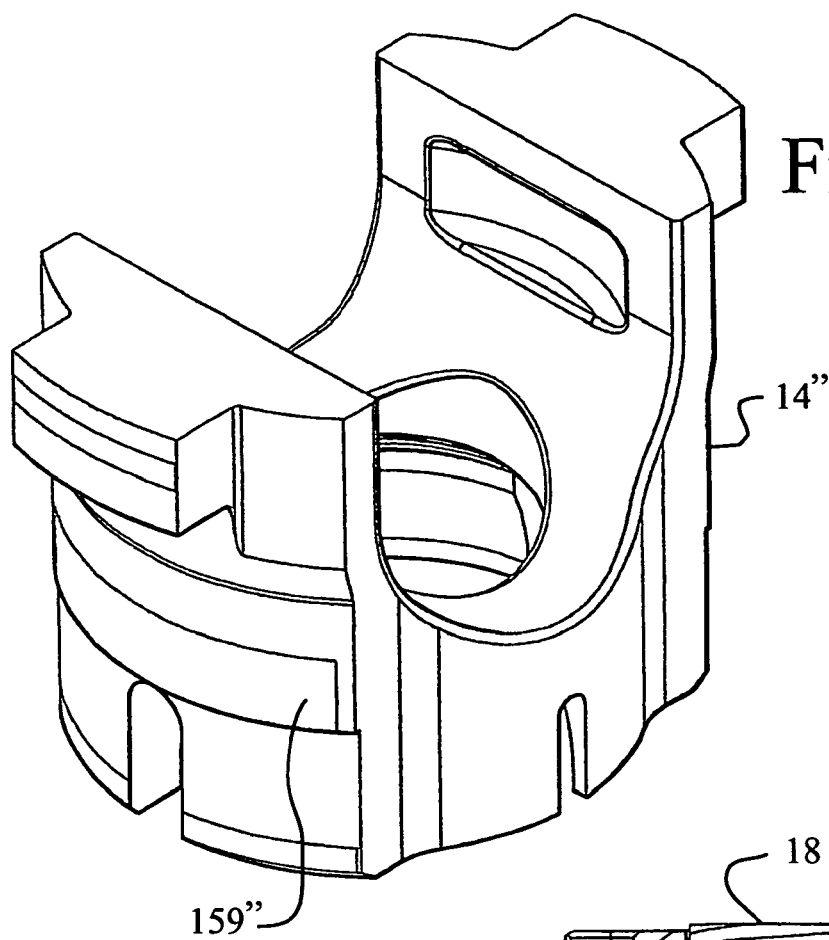
FIG. 72 is an enlarged perspective view of an alternative insert according to an embodiment of the invention.
Figure 73:
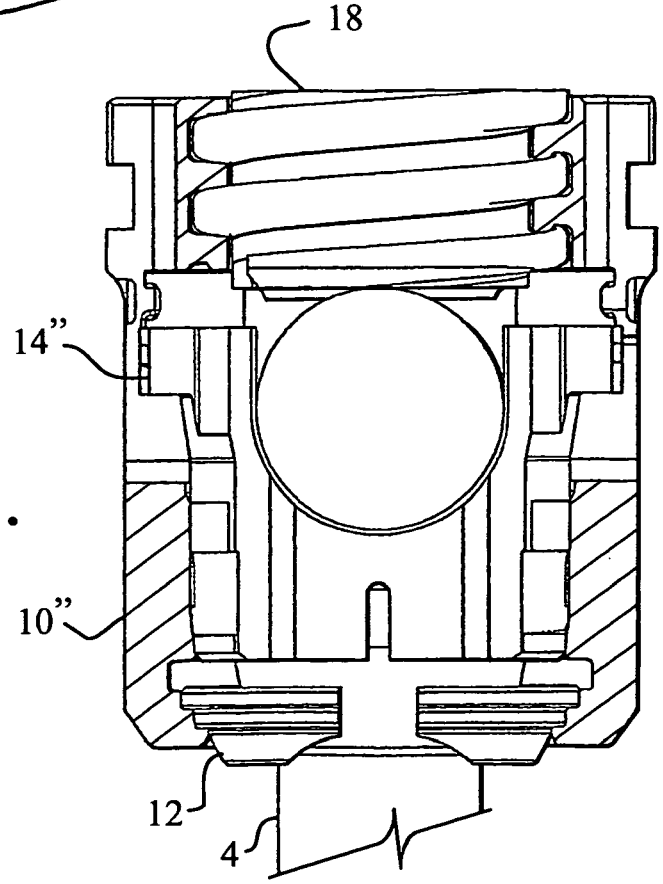
FIG. 73 is a partial front elevational view with portions broken away of the alternative insert of FIG. 72 shown assembled with an alternative receiver and the other components of the assembly shown in FIG. 1.
Figure 74:
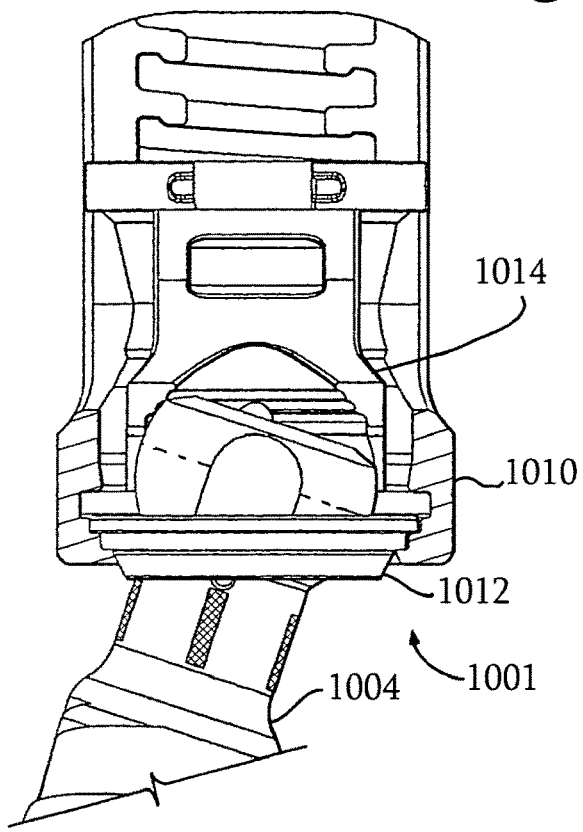
FIG. 74 is a partial front elevational view of an alternative uni-planar shank shown assembled with a uni-planar retainer according to an embodiment of the invention for use with the other components of the assembly of FIG. 1, with the exception that the receiver of FIG. 1 is modified (not shown) to include a stop that limits rotation of the alternative retainer with respect to the receiver.
Figure 75:
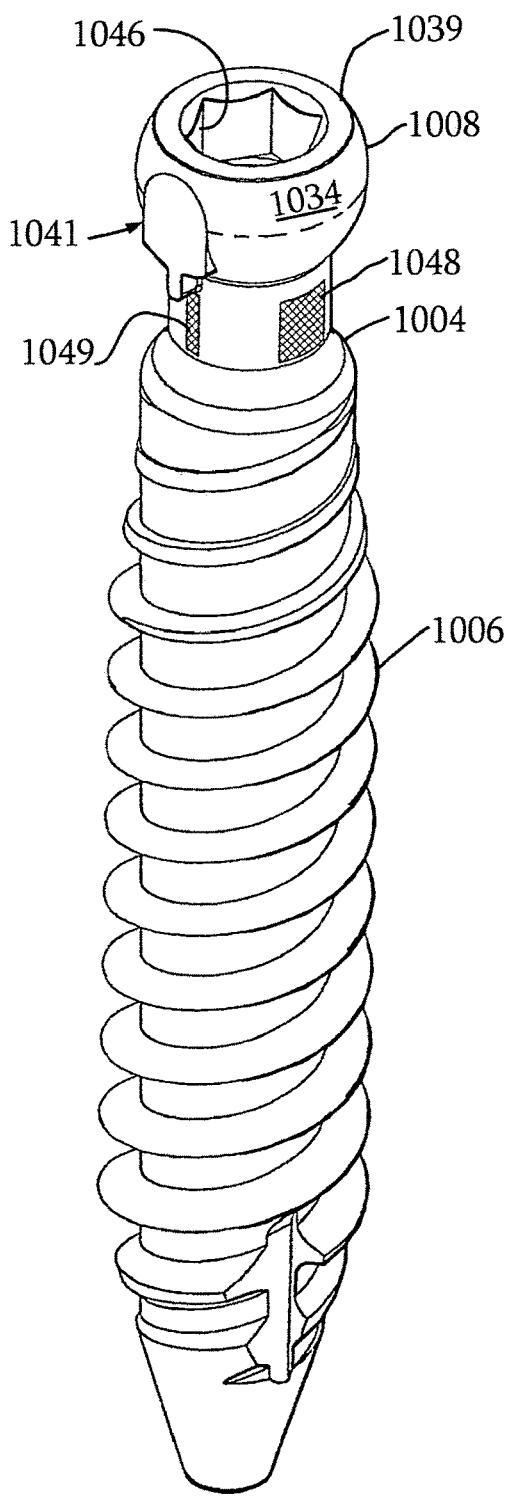
FIG. 75 is an enlarged perspective view of the uni-planar shank of FIG. 74.
Figure 76:
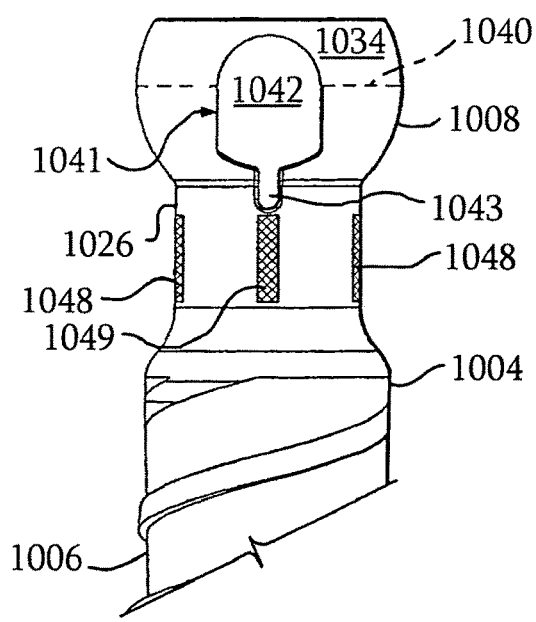
FIG. 76 is an enlarged and partial side elevational view of the shank of FIG. 75.
Figure 77:
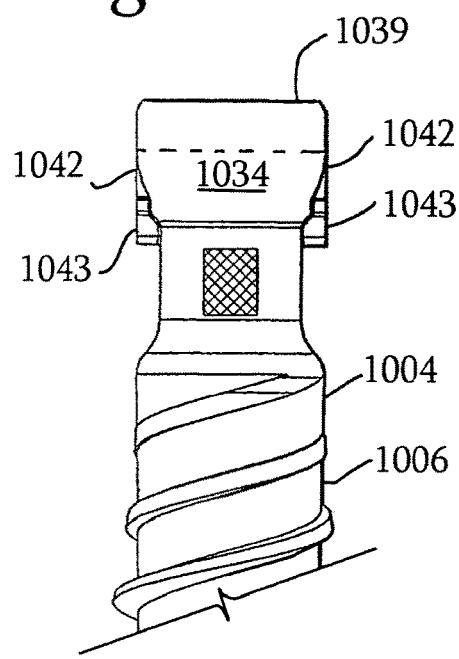
FIG. 77 is a partial front elevational view of the shank of FIG. 75.
Figure 79:
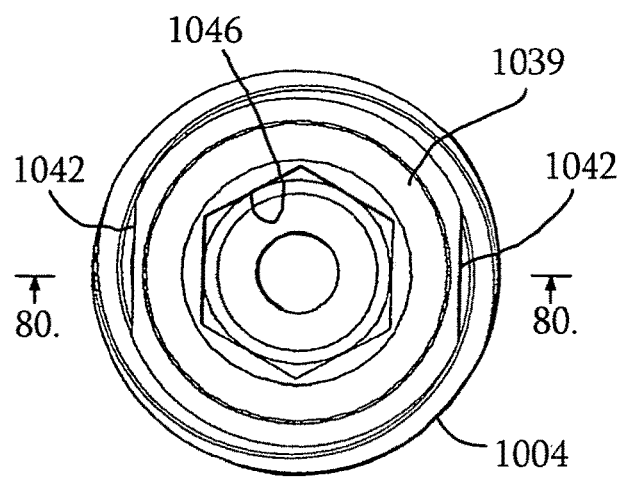
FIG. 79 is an enlarged top plan view of the shank of FIG. 75.
Figure 78:
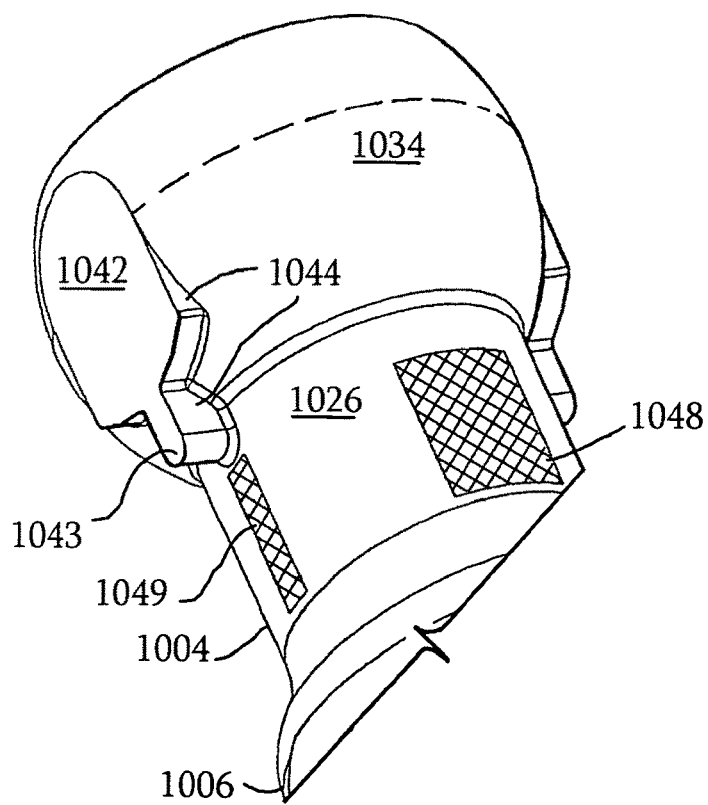
FIG. 78 is another enlarged and partial perspective view of the shank of FIG. 75.
Figure 80:
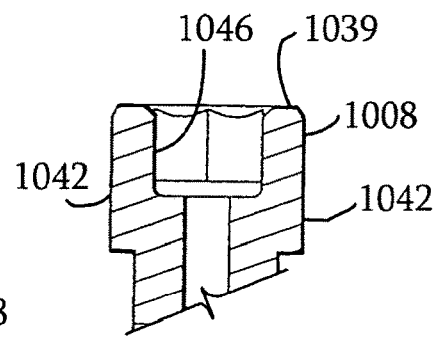
FIG. 80 is a reduced cross-sectional view taken along the line 80-80 of FIG. 79.
Figure 81:
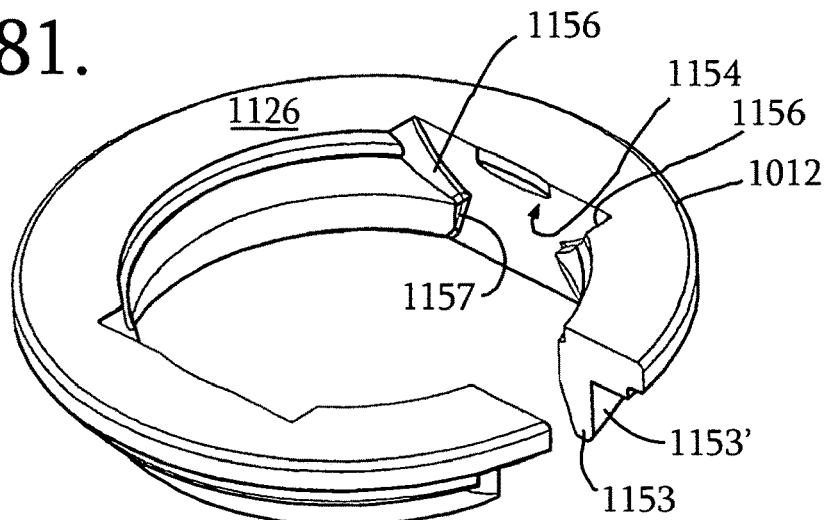
FIG. 81 is an enlarged perspective view of the alternative uni-planar retainer of FIG. 74.
Figure 82:
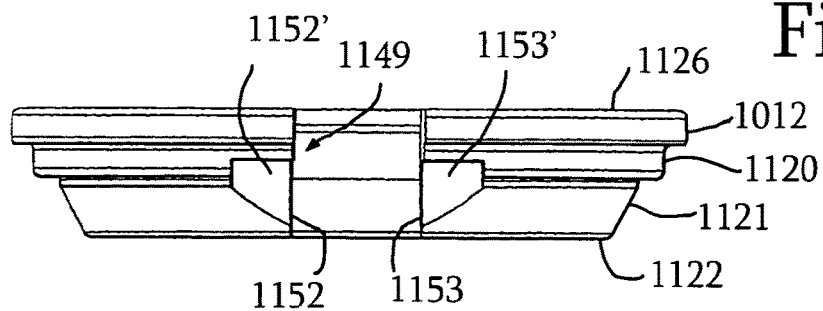
FIG. 82 is a front elevational view of the retainer of FIG. 81.
Figure 83:
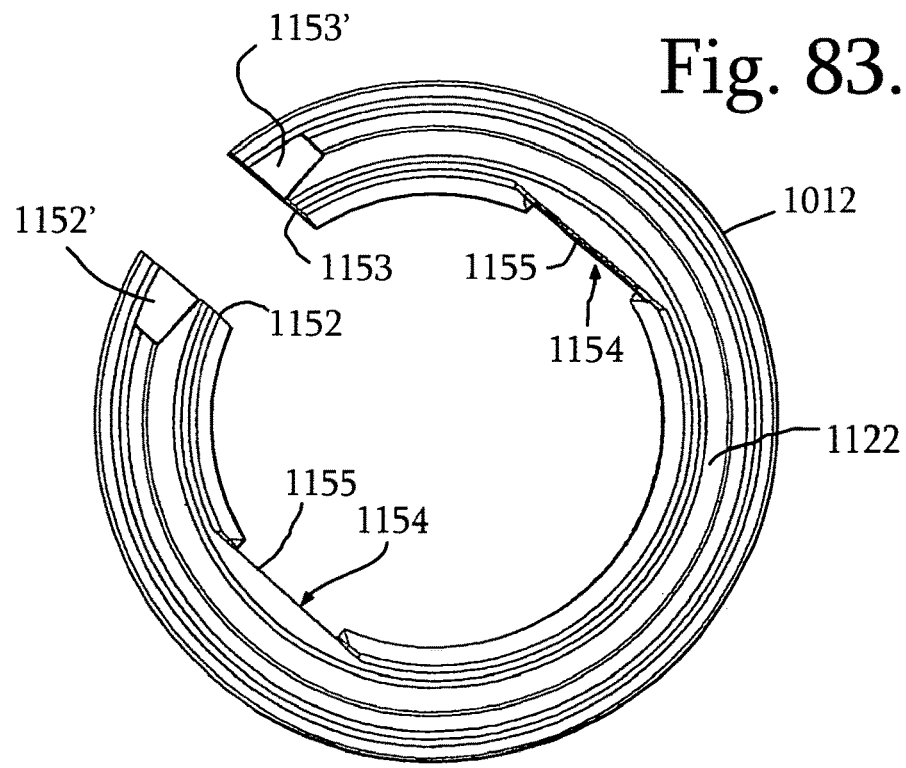
FIG. 83 is a bottom plan view of the retainer of FIG. 81.
Figure 84:
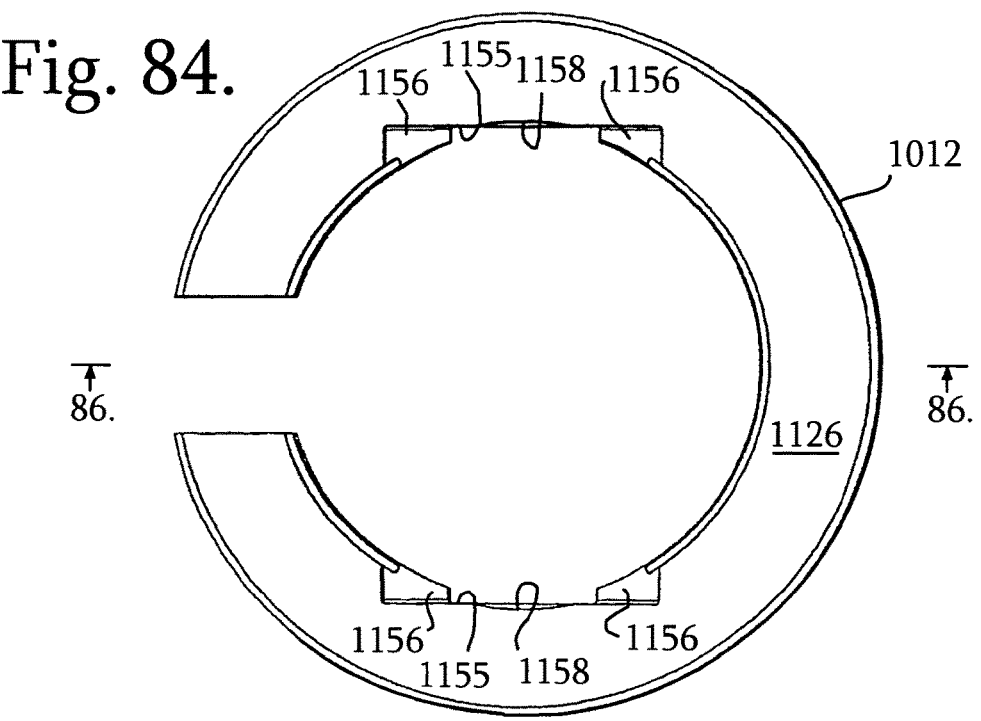
FIG. 84 is a top plan view of the retainer of FIG. 81.
Figure 85:
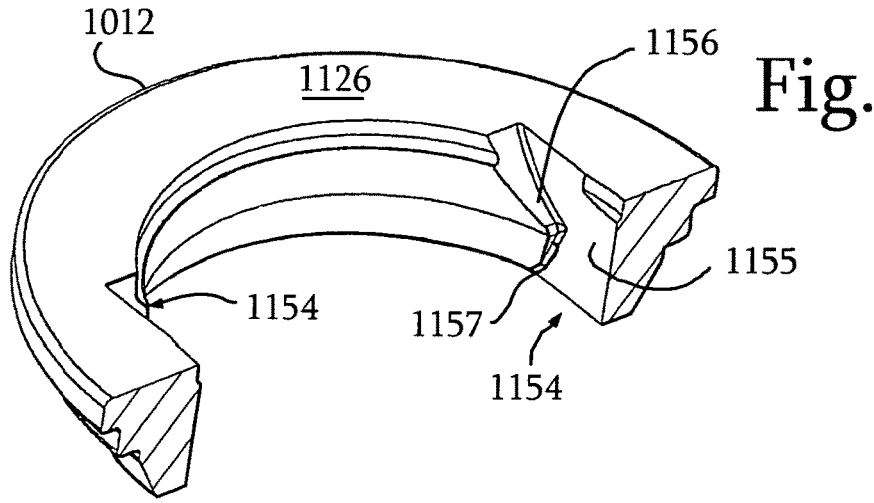
FIG. 85 is an enlarged perspective view of the retainer of FIG. 81 with portions broken away to show the detail thereof.
Figure 86:
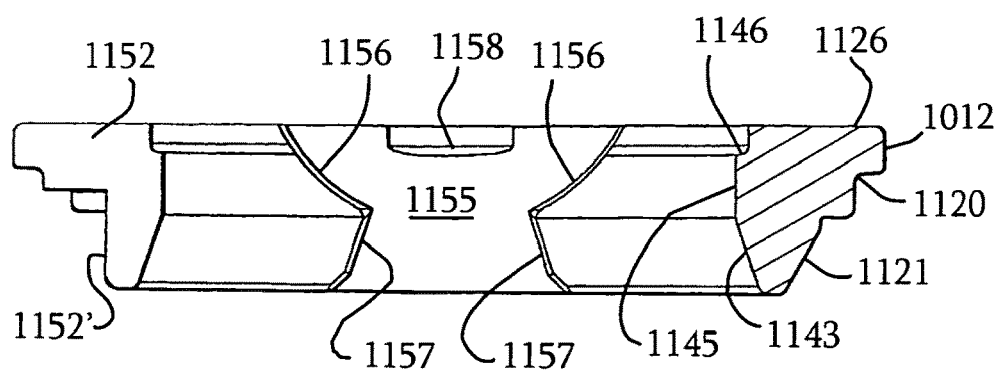
FIG. 86 is an enlarged cross-sectional view taken along the line 86-86 of FIG. 84.

FIGS. 72 and 73 illustrate an alternative insert 14" according to an embodiment of the invention. The insert 14" is substantially identical in form and function to the insert 14 previously described herein with the exception that the insert 14" has been made with a wider interference fit surface 159" and thicker, stronger insert arms. The receiver 10" has also been modified to cooperate with this thicker, stronger insert 14".

With reference to FIGS. 74-94, the reference number 1001 generally represents an alternative, uni-planar bone screw apparatus or assembly according to an embodiment of the invention. The assembly 1001 includes a shank 1004; a receiver 1010; an open tiered retainer 1012, a locking friction fit pressure insert 1014. There are many similarities between the assembly 1001 and the assembly 1. Differences between the embodiments 1 and 1001 mainly concern the shank 1004 and the retainer 1012. The receiver 1010 only differs from the receiver 10 in that the receiver 1010 includes an inwardly extending projection 1105 for holding the retainer 1012 in a desired position within the receiver, blocking any rotation of the retainer 1012 with respect to the receiver 1010. The friction fit insert 1014 is identical to the insert 14.

With particular reference to FIGS. 75-80, the uni-planar shank 1004 includes a body 1006, a substantially spherical head 1008 with an outer spherical surface 1034 that are substantially similar to the shank body 6 and head 8 previously described herein. Rather than the frusto-conical surface 39, the head 1008 has a planar annular top surface 1039. Formed in the spherical surface 1034 are opposed key portions, generally 1041 that include flat planar surfaces 1042 and a lower key extension or strip 1043 directed towards the shank body 1006. The flat surface 1042 extends downwardly along the extension 1043. Side surfaces 1044 extend between the flat surfaces 1042 and the shank spherical head 1034 and shank neck 1026. Indicator strips located on the shank neck 1026 include opposed pairs of wide strips 1048 narrow strips 1049 that allow a user to properly align and "pop" the uni-planar shank 1004 into the retainer 1012.

With reference to FIGS. 81-86, the uni-planar retainer 1012 includes all the features of the retainer 12 previously described herein and further includes inner key cut-outs generally 1154 as well as outer planar surface cuts 1152' and 1153' for cooperating with the alignment feature or projection 1105 of the receiver 1010. The inner key cut-outs 1154 are further defined by opposed flat surfaces 1155, curved surfaces 156 and curved surfaces 157 on either side of the flat 1155, the surfaces 1156 and 1157 forming a goblet-like shape for supporting the uni-planar pivoting of the shank key surfaces 1044. Small curved apertures 1158 are cut into the flat surface 1155 at the retainer top surface 1126.

Figure 87:
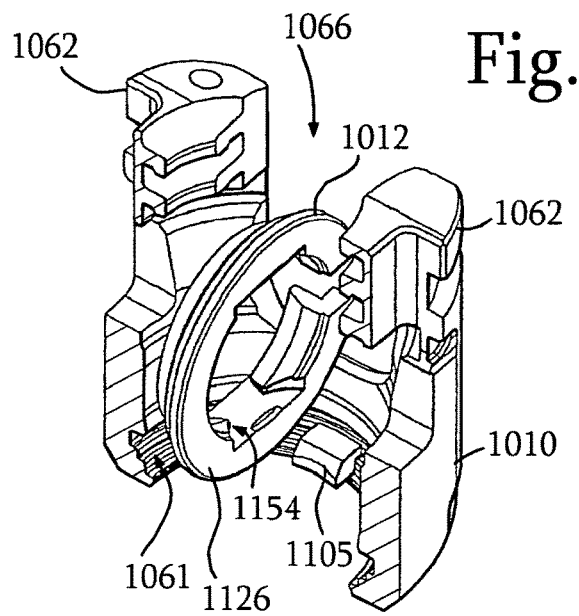
FIG. 87 is a reduced perspective view of the retainer of FIG. 81 shown being inserted into an alternative receiver embodiment of the invention, also shown in perspective view with portions broken away to show the detail thereof.
Figure 88:
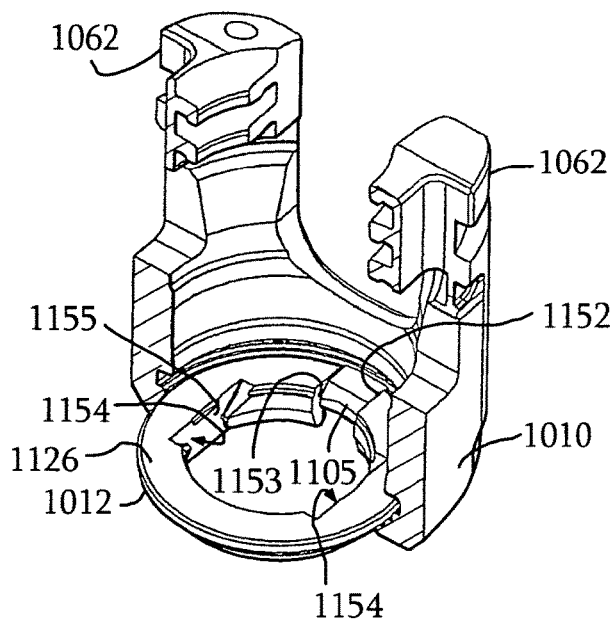
FIG. 88 is a perspective view with portions broken away, similar to FIG. 87 showing the retainer seated in the receiver with the retainer slit being fitted over a projection of the receiver, aligning the retainer to allow for a shank to pivot only in the same plane as a later inserted rod.
Figure 89:
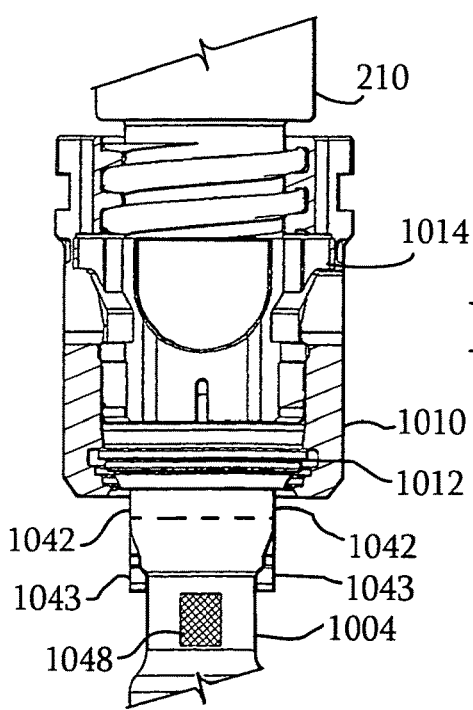
FIG. 89 is a reduced and partial front elevational view of the shank of FIG. 75 shown being inserted into an assembly made of the modified receiver of FIG. 87 and the insert and closure top of FIG. 1 along with the alternative retainer of FIG. 81 and utilizing the torque tool of FIG. 24.
Figure 90:
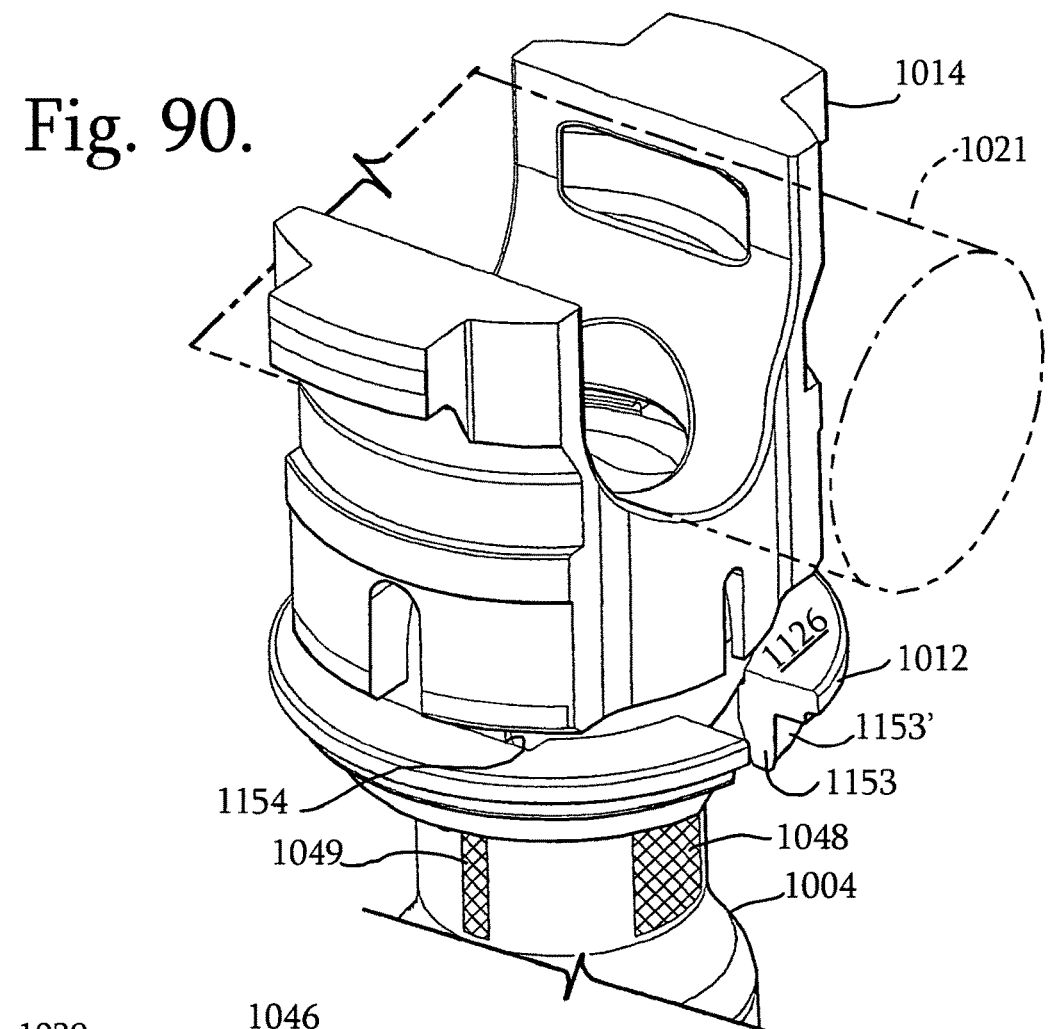
FIG. 90 is an enlarged and partial perspective view of the assembly of FIG. 89 shown with the receiver removed and a rod shown in phantom
Figure 91:
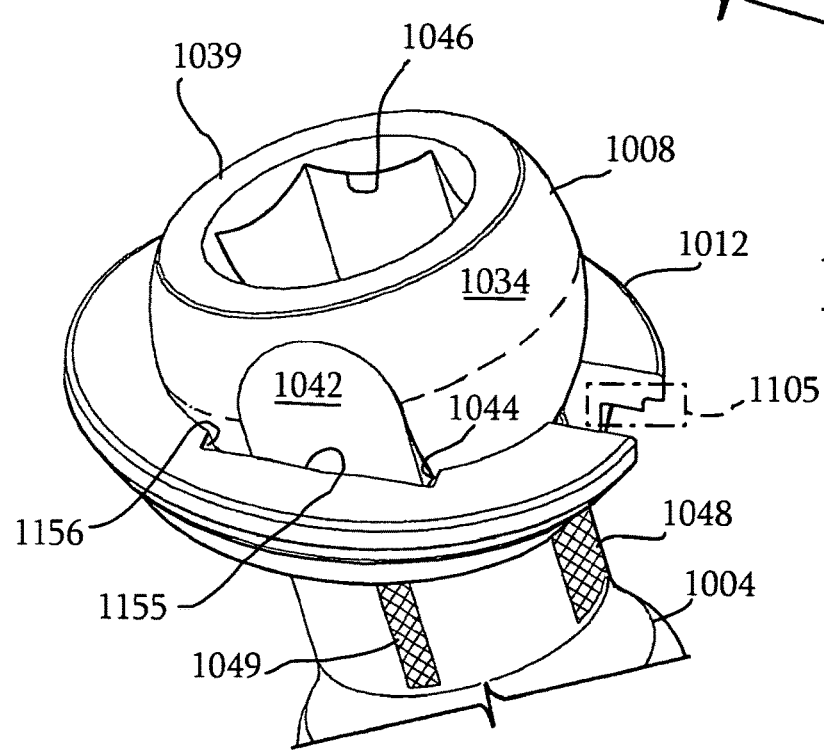
FIG. 91 is an enlarged and partial perspective view of the uni-planar retainer and the uni-planar shank (other components removed) to show the limited, single plane angulation possible due to the cooperation between the retainer (apertures) and the shank (keyed), with the rectangle in phantom indicating the projection from the receiver that fits in the gap of the open retainer and limits rotation of the retainer with respect to the receiver.
Figure 92:
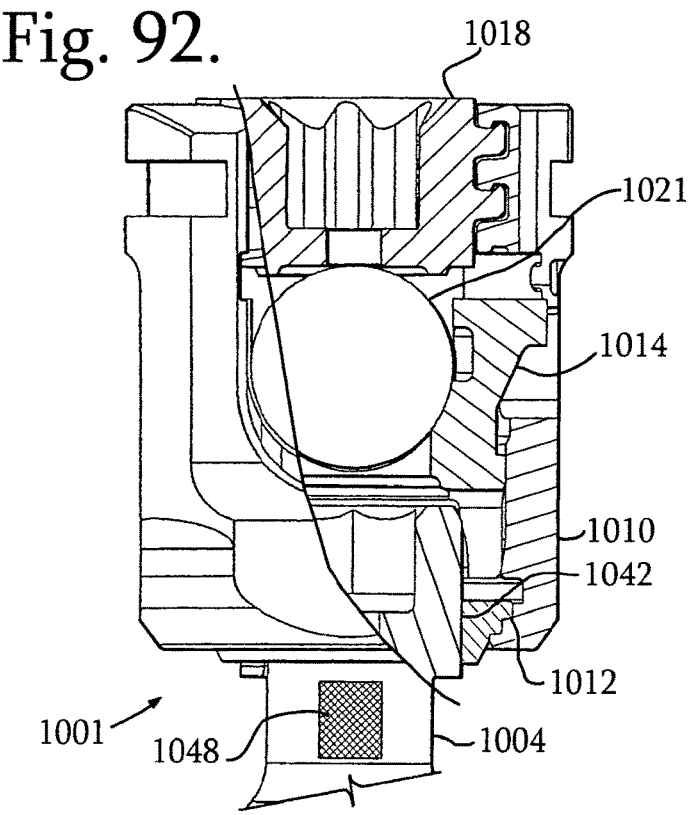
FIG. 92 is a partial perspective view with portions broken away of a fully locked bone screw assembly utilizing the uni-planar shank and retainer of FIG. 74.
Figure 93:
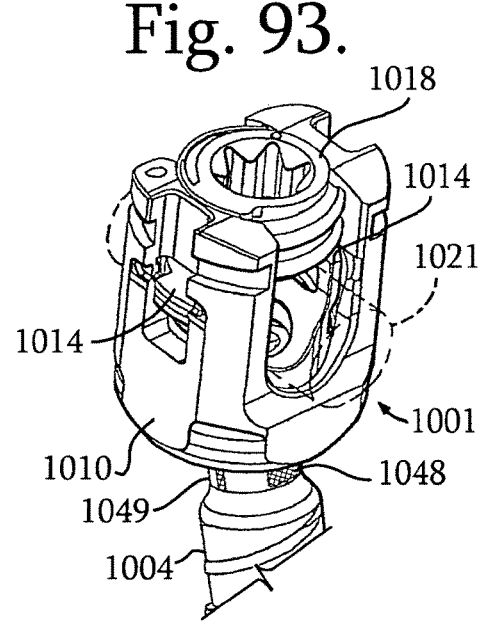
FIG. 93 is a reduced and partial perspective view of the assembly of FIG. 92 with the shank shown at an angle with respect to the receiver, a direction of angulation of the shank being in the same plane as the rod (shown in phantom).
Figure 94:
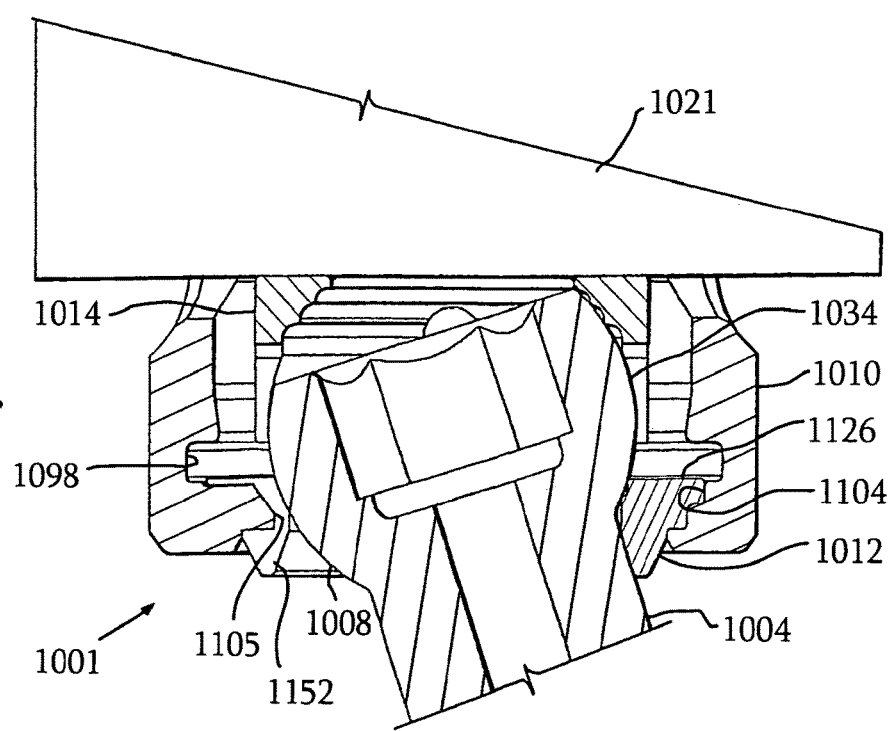
FIG. 94 is an enlarged and partial side elevational view of the assembly of FIG. 93 with portions broken away to show the detail thereof.

With reference to FIGS. 87 and 88, the retainer 1012 is loaded into the receiver 1010 in a manner similar to that described previously herein with respect to the retainer 12 and receiver 10. However, when the retainer 1012 is tilted as shown in FIG. 88, the retainer slit surfaces 1152 and 1153 must be located on either side of the receiver inner projection 1105. FIG. 89 illustrates the "popping" on of the uni-planar shank to the now mounted uni-planar retainer. With reference to both FIGS. 88 and 89, the shank must be positioned such that the shank flat surfaces 1042 slide up along the retainer flat surfaces 1155. With reference to FIG. 91, once the shank head 1008 passes through the retainer 1012 and is captured thereby, the key side surfaces 1044 are slidable along the retainer surfaces 1156, allowing for articulation of the shank 1004 with respect to the receiver 1010 in only one plane. Due to the location of the receiver projection 1105, the single plane of articulation is in direct alignment with the length of the rod 1021, shown for example, in FIG. 90. All of the other implantation and shank manipulation, friction fit and locking steps previously described herein with respect to the assembly 1 also apply to the assembly 1001. FIGS. 92-94 further illustrate the possible degrees of angular orientation between the uni-planar shank 1004 and retainer 1012. Thus, the "pop-on" uni-planar shank 1004 cooperates with the locking, friction fit insert 1014 and other components of the assembly 1001 shown in FIGS. 92-94, to provide for advantageous pre- or in-vivo shank assembly, friction fit or non-friction fit manipulation of the shank with respect to the receiver and final lock up utilizing the same tools and the same manipulation steps as previously described herein with respect to the assembly 1.

It is to be understood that while certain forms of the present invention have been illustrated and described herein, it is not to be limited to the specific forms or arrangement of parts described and shown.

What is claimed is:

1. A pivotal spinal fixation system for securing an elongate rod to a spine of a patient, the pivotal spinal fixation system comprising:
a plurality of bone anchors, each bone anchor comprising a longitudinal axis, a capture portion having a partial spherical shape with flat side surfaces and a unitary anchor portion opposite the capture portion configured for attachment to the spine;
at least one multi-planar receiver having an upper channel portion configured to receive the elongate rod and a lower base portion defining an internal cavity centered about a vertical centerline axis and having a continuous circumferential engagement surface proximate a bottom opening;
at least one uni-planar receiver having an upper channel portion configured to receive the elongate rod and a lower base portion defining an internal cavity centered about a vertical centerline axis and having a non-continuous circumferential engagement surface proximate a bottom opening; and
a plurality of retainers, each retainer configured for positioning within the internal cavity of the at least one multi-planar receiver or the at least one uni-planar receiver prior to the capture portion of the bone anchor and having a non-continuous circumferential outer surface configured for non-pivotal engagement with the continuous circumferential engagement surface of the at least one multi-planar receiver or the non-continuous circumferential engagement surface of the at least one uni-planar receiver, and an inner surface configured to expand and contract around the capture portion and flat side surfaces of one of the plurality of bone anchors so as to capture the bone anchor within the internal cavity of the at least one multi-planar receiver or the at least one uni-planar receiver upon the capture portion being uploaded through the bottom opening to form at least one multi-planar receiver assembly or at least one uni-planar receiver assembly, respectively,
wherein the at least one multi-planar receiver assembly is configured to provide for pivotal motion of the bone anchor relative to the multi-planar receiver in any of a plurality of angular directions relative to the vertical centerline axis of the multi-planar receiver, and
wherein the at least one uni-planar receiver assembly is configured to limit pivotal motion of the bone anchor relative to the uni-planar receiver to a single plane relative to the vertical centerline axis of the uni-planar receiver.

2. The pivotal spinal fixation system of claim 1, wherein each of the retainers further comprises at least one gap extending completely through a thickness of the retainer.

3. The pivotal spinal fixation system of claim 2, wherein each of the retainers is an open ring retainer.

4. The pivotal spinal fixation system of claim 2, wherein each of the retainers is identical in size and shape with the other retainers.

5. The pivotal spinal fixation system of claim 1,
wherein the non-continuous circumferential outer surface of the retainer in the at least one multi-planar receiver assembly is configured for slidable rotatable engagement with the continuous circumferential engagement surface of the multi-planar receiver so as to provide for the pivotal motion of the bone anchor relative to the multi-planar receiver in any of a plurality of planes extending through the vertical centerline axis of the multi-planar receiver.

6. The pivotal spinal fixation system of claim 1,
wherein the non-continuous circumferential outer surface of the retainer in the at least one uni-planar receiver assembly is configured for non-rotatable engagement with the non-continuous circumferential engagement surface of the uni-planar receiver to limit pivotal motion of the bone anchor relative to the uni-planar receiver in a single plane extending through the vertical centerline axis of the uni-planar receiver.

7. The pivotal spinal fixation system of claim 6, wherein the non-continuous circumferential engagement surface of the at least one uni-planar receiver further comprises an inwardly-extending projection configured to protrude into a gap formed into the outer surface of the retainer to inhibit rotation of the retainer along the non-continuous circumferential engagement surface of the at least one uni-planar receiver.

8. The pivotal spinal fixation system of claim 1,
wherein the flat side surfaces of the capture portion of each of the plurality of bone anchors further comprises a pair of opposite outward-facing planar surfaces extending parallel to the longitudinal axis of the bone anchor, and
wherein the inner surface of each of the retainers further comprises a pair of opposing inward-facing planar surfaces configured to slidably engage the pair of opposite outward-facing planar surfaces of the capture portion to limit the pivotal motion of the bone anchor relative to the retainer to a single plane.

9. The pivotal spinal fixation system of claim 1, wherein the bone anchor of the at least one multi-planar receiver assembly or the at least one uni-planar receiver assembly is pivotal with respect to the multi-planar receiver or the uni-planar receiver, respectively, prior to securing the elongate rod within the upper channel portion of the multi-planar receiver or the uni-planar receiver with a closure.

10. The pivotal spinal fixation system of claim 1, wherein the capture portion of each of the plurality of bone anchors further comprises a midsection defining a hemisphere plane perpendicular to the longitudinal axis, an upper partial spherical outer surface above the hemisphere plane, and a lower partial spherical outer surface below the hemisphere plane toward a neck portion of the bone anchor that extends between the capture portion and the anchor portion.

11. The pivotal spinal fixation system of claim 10,
wherein the capture portion further comprises an upwardly-opening drive socket configured to mate with a drive tool, an upward-facing planar top surface perpendicular to the longitudinal axis and surrounding the drive socket, and
wherein the upper partial spherical outer surface extends upward from the hemisphere plane to the upward-facing planar top surface.

12. The pivotal spinal fixation system of claim 1, further comprising an insert positionable within the upper channel portion of the at least one multi-planar receiver or the at least one uni-planar receiver, the insert having an upper surface configured to receive the elongate rod, a lower surface configured to engage the capture portion of the bone anchor to transfer a downwardly-directed force applied by a closure to lock the assembly.

13. The pivotal spinal fixation system of claim 12, wherein the insert includes a central aperture configured to provide access to the capture portion of the bone anchor for a drive tool.

14. The pivotal spinal fixation system of claim 1, wherein the bottom opening of the at least one multi-planar receiver or of the at least one uni-planar receiver includes at least one cut-out to provide for increased pivotal motion of the bone anchor relative to the multi-planar or uni-planar receiver in at least one direction.

15. The pivotal spinal fixation system of claim 1, wherein the retainer of the at least one multi-planar assembly or of the at least one uni-planar receiver assembly includes at least one cut-out to provide for increased pivotal motion of the bone anchor relative to the multi-planar or uni-planar receiver in at least one direction.

16. The pivotal spinal fixation system of claim 1, wherein the upper channel portion of the at least one multi-planar receiver or the at least one uni-planar receiver further comprises an upwardly-open channel defined by interior surfaces of a pair of upright arms extending upwardly from the lower base portion of the multi-planar or uni-planar receiver.

17. The pivotal spinal fixation system of claim 1, wherein the upper channel portion of the at least one multi-planar receiver or the at least one uni-planar receiver includes a closure mating structure.

18. The pivotal spinal fixation system of claim 17, wherein the closure mating structure further comprises a helically wound guide and advancement structure.

19. The pivotal spinal fixation system of claim 17 and further comprising the elongate rod and a plurality of closures, wherein each of the closures is configured for positioning within the upper channel portion of the at least one multi-planar receiver or the at least one uni-planar receiver above the elongate rod and in engagement with the closure mating structure to apply a downwardly-directed force towards a top of the elongate rod, so as to frictionally lock the bone anchor in a fixed position relative to the at least one multi-planar receiver or the at least one uni-planar receiver.

20. A pivotal spinal fixation system for securing an elongate rod to a spine of a patient, the pivotal spinal fixation system comprising:
  a plurality of bone anchors, each bone anchor comprising a longitudinal axis, a capture portion having a partial spherical shape with flat side surfaces and a unitary anchor portion opposite the capture portion configured for attachment to the spine;
  at least one multi-planar receiver having an upper channel portion configured to receive the elongate rod and a lower base portion defining an internal cavity centered about a vertical centerline axis and having a continuous circumferential engagement surface proximate a bottom opening;
  at least one uni-planar receiver having an upper channel portion configured to receive the elongate rod and a lower base portion defining an internal cavity centered about a vertical centerline axis and having a non-continuous circumferential engagement surface proximate a bottom opening; and
  a plurality of retainers, each retainer having a non-continuous circumferential outer surface configured for slidable rotatable engagement with the continuous circumferential engagement surface of the at least one multi-planar receiver and for non-rotatable engagement with the non-continuous circumferential engagement surface of the at least one uni-planar receiver, each retainer further including an inner surface configured to engage the capture portion and flat side surfaces of one of the plurality of bone anchors so as to capture the bone anchor within the internal cavity of the at least one multi-planar receiver or within the internal cavity of the at least one uni-planar receiver,
  wherein a retainer in engagement with the continuous circumferential engagement surface of a multi-planar receiver is configured to provide for pivotal motion of the bone anchor relative to the multi-planar receiver in any of a plurality of angular directions relative to the vertical centerline axis of the multi-planar receiver, and
  wherein a retainer in engagement with the non-continuous circumferential engagement surface of a uni-planar receiver is configured to limit pivotal motion of the bone anchor relative to the uni-planar receiver to a single plane relative to the vertical centerline axis of the uni-planar receiver.

21. The pivotal spinal fixation system of claim 20, wherein the continuous circumferential engagement surface of the at least one multi-planar receiver and the non-continuous circumferential engagement surface of the at least one uni-planar receiver includes a vertically extending surface.

22. The pivotal spinal fixation system of claim 20, wherein each of the plurality of retainers is configured to non-pivotally engage the continuous circumferential engagement surface of the at least one multi-planar receiver or the non-continuous circumferential engagement surface of the at least one uni-planar receiver.

23. The pivotal spinal fixation system of claim 20,
  wherein the flat side surfaces of the capture portion of each of the plurality of bone anchors further comprises a pair of opposite outward-facing planar surfaces extending parallel to the longitudinal axis of the bone anchor, and
  wherein the inner surface of each of the plurality of retainers further comprises a pair of opposing inward-facing planar surfaces configured to slidably engage the opposite outward-facing planar surfaces of the capture portion to limit the pivotal motion of the bone anchor relative to the retainer in a single plane.

24. The pivotal spinal fixation system of claim 20, wherein each of the plurality of retainers is an open ring retainer having a gap extending completely through a thickness of the retainer.

25. The pivotal spinal fixation system of claim 24, wherein the non-continuous circumferential engagement surface of the at least one uni-planar receiver further comprises an inwardly-extending projection configured to protrude into the gap of the retainer to inhibit rotation of the retainer along the non-continuous circumferential engagement surface of the at least one uni-planar receiver.

26. The pivotal spinal fixation system of claim 20, wherein the capture portion of each of the plurality of bone anchors is configured for uploading into the internal cavity of one of the multi-planar or uni-planar receivers through the bottom opening with the bone anchor extending downward through the bottom opening, and with the bone anchor being pivotal with respect to the multi-planar or uni-planar receiver prior to securing the elongate rod within the upper channel portion of the multi-planar or uni-planar receiver with a closure.

27. The pivotal spinal fixation system of claim 20, wherein the capture portion of each of the plurality of bone anchors further comprises a midsection defining a hemisphere plane perpendicular to the longitudinal axis, an upper partial spherical outer surface above the hemisphere plane, and a lower partial spherical outer surface below the hemisphere plane toward a neck portion of the bone anchor that extends between the capture portion and the anchor portion.

28. The pivotal spinal fixation system of claim 27,
wherein the capture portion further comprises an upwardly-opening drive socket configured to mate with a drive tool, an upward-facing planar top surface perpendicular to the longitudinal axis and surrounding the drive socket, and
wherein the upper partial spherical outer surface extends upward from the hemisphere plane to the upward-facing planar top surface.

29. The pivotal spinal fixation system of claim 20, further comprising an insert positionable within the upper channel portion of the at least one multi-planar receiver or the at least one uni-planar receiver, the insert having an upper surface configured to receive the elongate rod, a lower surface configured to engage the capture portion of the bone anchor to transfer a downwardly-directed force applied by a closure to lock an assembly of the system.

30. The pivotal spinal fixation system of claim 29, wherein the insert includes a central aperture configured to provide access to the capture portion of the bone anchor for a drive tool.

31. The pivotal spinal fixation system of claim 20, wherein the bottom opening of the at least one multi-planar receiver or of the at least one uni-planar receiver includes at least one cut-out to provide for increased pivotal motion of the bone anchor relative to the multi-planar or uni-planar receiver in at least one direction.

32. The pivotal spinal fixation system of claim 20, wherein each of the plurality of retainers includes at least one cut-out to provide for increased pivotal motion of the bone anchor relative to the at least one multi-planar receiver or the at least one uni-planar receiver in at least one direction.

33. The pivotal spinal fixation system of claim 20, wherein the upper channel portion of each of the at least one multi-planar receiver and the at least one uni-planar receiver further comprises an upwardly-open channel defined by interior surfaces of a pair of upright arms extending upwardly from the lower base portion of the multi-planar or uni-planar receiver.

34. The pivotal spinal fixation system of claim 20, wherein the upper channel portion of each of the at least one multi-planar receiver and the at least one uni-planar receiver includes a closure mating structure.

35. The pivotal spinal fixation system of claim 34, wherein the closure mating structure further comprises a helically wound guide and advancement structure.

36. The pivotal spinal fixation system of claim 35 and further comprising the elongate rod and a plurality of closures, wherein each of the plurality of closures is configured for positioning within the upper channel portion of the at least one multi-planar receiver or the at least one uni-planar receiver above the elongate rod and in engagement with the closure mating structure to apply a downwardly-directed force towards a top of the elongate rod, so as to frictionally lock the bone anchors in a fixed position relative to the at least one multi-planar receiver or the at least one uni-planar receiver.

37. The pivotal spinal fixation system of claim 20, wherein at least one of the plurality of bone anchors includes a cannulated opening centered around the longitudinal axis and extending along the entire length of the bone anchor.

* * * * *